(12) United States Patent
Sato et al.

(10) Patent No.: US 12,108,746 B2
(45) Date of Patent: Oct. 8, 2024

(54) TRANSGENIC ANIMAL HAVING CREBBP GENE INTO WHICH MUTATION HAS BEEN INTRODUCED

(71) Applicant: KURUME UNIVERSITY, Fukuoka (JP)

(72) Inventors: Takahiro Sato, Kurume (JP); Masayasu Kojima, Kurume (JP); Kanae Oishi, Kurume (JP)

(73) Assignee: KURUME UNIVERSITY, Fukuoka (JP)

(*) Notice: Subject to any disclaimer, the term of this patent is extended or adjusted under 35 U.S.C. 154(b) by 825 days.

(21) Appl. No.: 17/255,688

(22) PCT Filed: Jun. 28, 2019

(86) PCT No.: PCT/JP2019/025902
§ 371 (c)(1),
(2) Date: Dec. 23, 2020

(87) PCT Pub. No.: WO2020/004640
PCT Pub. Date: Jan. 2, 2020

(65) Prior Publication Data
US 2021/0251198 A1 Aug. 19, 2021

(30) Foreign Application Priority Data
Jun. 29, 2018 (JP) .................. 2018-124666

(51) Int. Cl.
*A01K 67/0275* (2024.01)
*C12N 9/10* (2006.01)
*C12Q 1/6883* (2018.01)

(52) U.S. Cl.
CPC ........ *A01K 67/0275* (2013.01); *C12N 9/1029* (2013.01); *C12Q 1/6883* (2013.01); *A01K 2217/05* (2013.01); *A01K 2227/105* (2013.01); *A01K 2267/0306* (2013.01); *C12Q 2600/156* (2013.01)

(58) Field of Classification Search
CPC ............ A01K 67/0275; A01K 2217/05; A01K 2227/105; A01K 2267/0306; A01K 2217/072; A01K 67/0276; C12N 9/1029; C12N 9/10; C12Q 1/6883; C12Q 2600/156
See application file for complete search history.

(56) References Cited

PUBLICATIONS

Tang et al (Molecular Brain Research 137 (2005) 213-222, doi:10.1016/j.molbrainres.2005.03.009, Available online Apr. 25, 2005) (Year: 2005).*
Tratar et al (Front. Oncol. 8:268, doi: 10.3389/fonc.2018.00268, Published: Jul. 20, 2018) (Year: 2018).*
Dawson et al (Nat Neurosci 21, 1370-1379 (2018). https://doi.org/10.1038/s41593-018-0236-8, Sep. 24, 2018) (Year: 2018).*
Myers et al (Current Protocols in Neuroscience, 89, e81. doi: 10.1002/cpns.81, Aug. 19, 2019) (Year: 2019).*
Schon et al (Journal of Allergy and Clinical Immunology vol. 147, Issue 2, Feb. 2021, pp. 439-455, https://doi.org/10.1016/j.jaci.2020.04.034) (Year: 2021).*
Guo et al., 2015 (Cell Research (2015) 25:767-768. doi:10.1038/cr.2015.64; published online Jun. 2, 2015) (Year: 2015).*
Kang et al., 2018 (Human Molecular Genetics, vol. 27, No. 2, p. 211-223, doi: 10.1093/hmg/ddx366) (Year: 2018).*
Maqbool et al (Biochem. Soc. Trans. (2015) 43, 1011-1017; doi:10.1042/BST20150135) (Year: 2015).*
Cruz et al (Methods in Molecular Biology 2017, vol. 1654, Chapter 5, pp. 55-75, ISBN 978-1-4939-7231-9, https://doi.org/10.1007/978-1-4939-7231-9_5 ) (Year: 2017).*
Yan et al (Computers in Biology and Medicine, 154 (2023): 106466, p. 1-12, https://doi.org/10.1016/j.compbiomed.2022.106446 ) (Year: 2023).*
Del Rio, Gabriel (Computation 2021, 9, 39, p. 1-11,https://doi.org/10.3390/computation9040039) (Year: 2021).*
Alari V, et al., "iPSC-derived neurons of CREBBP- and EP300-mutated Rubinstein-Taybi syndrome patients show morphological alterations and hypoexcitability", Stem Cell Research, May 30, 2018, vol. 30, pp. 130-140.
Merk D. J., et al., "Opposing Effects of CREBBP Mutations Govern the Phenotype of Rubinstein-Taybi Syndrome and Adult SHH Medulloblastoma", Developmental Cell, Mar. 26, 2018, vol. 44, Issue 6, pp. 709-724.
Menke L. A., et al., "Further delineation of an entity caused by CREBBP and EP300 mutations but not resembling Rubinstein-Taybi syndrome", American Journal of Medical Genetics Part A, Apr. 2018, vol. 176, Issue 4, pp. 862-876.
Eser M., et al., "A case with Rubinstein-Taybi syndrome: A novel frameshift mutation in the CREBBP gene", The Turkish Journal of Pediatrics, 2017, vol. 59 (5), pp. 601-603.

(Continued)

*Primary Examiner* — Shin Lin Chen
*Assistant Examiner* — Khoa Nhat Tran
(74) *Attorney, Agent, or Firm* — Wenderoth, Lind & Ponack, L.L.P.

(57) ABSTRACT

The disclosure provides a non-human transgenic animal having at least one CREBBP gene locus into which a mutation has been introduced, wherein the mutated CREBBP gene encodes a mutant CREBBP consisting of an amino acid sequence having at least 90% identity with the amino acid sequence of SEQ ID NO: 5. The disclosure also provides a method of producing the transgenic animal comprising introducing a mutation into at least one CREBBP gene locus of a non-human animal. The disclosure further provides use of the transgenic animal as a model of Rubinstein-Taybi syndrome or advanced sleep phase syndrome.

3 Claims, 21 Drawing Sheets

Specification includes a Sequence Listing.

(56) References Cited

PUBLICATIONS

Rokunohe D., et al., "Rubinstein-Taybi syndrome with multiple pilomatricomas: The first case diagnosed by CREBBP mutation analysis", Journal of Dermatological Science, Sep. 2016, vol. 83 (3), pp. 240-242.

Menke L. A., et al., "CREBBP mutations in Individuals without Rubinstein-Taybi Syndrome Phenotype", American Journal of Medical Genetics Part A, Oct. 2016, vol. 170 (10), pp. 2681-2693.

De Vries T. I., et al., "Mosaic CREBBP mutation causes overlapping clinical features of Rubinstein-Taybi and Filippi syndromes", European Journal of Human Genetics, Aug. 2016, vol. 24(9), pp. 1363-1366.

Wincent J., et al., "CREBBP and EP300 mutational spectrum and clinical presentations in a cohort of Swedish patients with Rubinstein-Taybi syndrome", Molecular Genetics & Genomic Medicine, Sep. 22, 2015, vol. 4(1), pp. 39-45.

Kamenarova K., et al., "Identification of a novel de novo mutation of CREBBP in a patient with Rubinstein-Taybi syndrome by targeted next-generation sequencing: a case report", Human Pathology, Jan. 2016, vol. 47(1), pp. 144-149.

Huh R., et al., "*Letter to the Editor:* A Novel Mutation in the CREBBP Gene of a Korean Girl with Rubinstein-Taybi syndrome", Annals of Clinical & Laboratory Science, 2015 Summer, vol. 45, No. 4, pp. 458-461.

Rusconi D., et al., "Characterization of 14 novel deletions underlying Rubinstein-Taybi syndrome: an update of the CREBBP deletion repertoire", Human Genetics, Jun. 2015, vol. 134(6), pp. 613-626.

Yoo H. J., et al., "Whole Exome Sequencing for a Patient with Rubinstein-Taybi Syndrome Reveals de Novo Variants besides an Overt CREBBP Mutation", International Journal of Molecular Sciences, Mar. 11, 2015, vol. 16(3), pp. 5697-5713.

Spena S., et al., "Insights into genotype-phenotype correlations from CREBBP point mutation screening in a cohort of 46 Rubinstein-Taybi syndrome patients", Clinical Genetics, Nov. 2015, vol. 88(5), pp. 431-440.

Kim S. R., et al., "Cryptic Microdeletion of the CREBBP Gene from t(1;16) (p36.2;p13.3) as a Novel Genetic Defect Causing Rubinstein-Taybi Syndrome", Annals of Clinical & Laboratory Science, 2013 Fall, vol. 43, No. 4, pp. 450-456.

Marzuillo P., et al., "*Novel cAMP binding protein-BP (CREBBP)* mutation in a girl with Rubinstein-Taybi syndrome, GH deficiency, Arnold Chiari malformation and pituitary hypoplasia", BMC Medical Genetics, Feb. 23, 2013, vol. 14 (28), 6 total pages.

Lai A. H., et al., "A submicroscopic deletion involving part of the CREBBP gene detected by array-CGH in a patient with Rubinstein-Taybi syndrome", Gene, May 10, 2012, vol. 499 (1), pp. 182-185.

Caglayan A. O., et al., "A boy with classical Rubinstein-Taybi syndrome but no detectable mutation in the CREBBP and EP300 genes", Genetic counseling, 2011, vol. 22, No. 4, pp. 341-346.

Li C., et al., "A Novel Mutation c.4003 G>C in the CREBBP Gene in an Adult Female with Rubinstein-Taybi Syndrome Presenting With Subtle Dysmorphic Features", American Journal of Medical Genetics Part A, Nov. 2010, vol. 152A(11), pp. 2939-2941V.

Oike Y., et al., "Mice Homozygous for a Truncated Form of CREB-Binding Protein Exhibit Defects in Hematopoiesis and vasculoangiogenesis", Blood, May 1, 1999, vol. 93, No. 9, pp. 2771-2779.

Kasper, L. H. et al., "Two transactivation mechanisms cooperate for the bulk of HIF-1-responsive gene expression", The EMBO Journal, 2005, vol. 24, pp. 3846-3858, Supplementary Information.

Bartsch, O. et al., "Molecular studies in 10 cases of Rubinstein-Taybi syndrome, including a mild variant showing a missense mutation in codon 1175 of CREBBP", J. Med. Genet., 2002, vol. 39, pp. 496-501.

Bentivegna, A. et al., "Rubinstein-Taybi Syndrome: spectrum of CREBBP mutations in Italian patients", BMC Medical Genetics, 2006, vol. 7(77), 13 total pages.

International Search Report issued Sep. 24, 2019 in International (PCT) Application No. PCT/JP2019/025902.

Translation of International Preliminary Report on Patentability and Written Opinion of the Searching Authority issued Dec. 29, 2020 in International (PCT) Application No. PCT/JP2019/025902.

\* cited by examiner

● Whole body

Dwarf    Normal

● Head

Dwarf    Normal

☐ : Normal mice (n=6), ▨ : Dwarf mice (n=6)

● Nasal dorsal length

● Intercanthal distance

☐ : Normal mice (n=6), ▨ : Dwarf mice (n=6)

Fig. 16

Mus musculus CREB binding protein (Crebbp) mRNA (7326 bp)

atggccgagaacttgctggacggacgcccaaccccaaacgagccaaactcagctcgcccggcttctccgcgaa
tgacaacacagattttggatcattgtttgacttggaaaatgaccttcctgatgagctgatccccaatggagaattaagc
cttttaaacagtgggaaccttgttccagatgctgcgtccaaacataaacaactgtcagagcttcttagaggaggcagc
ggctctagcatcaacccagggataggcaatgtgagtgccagcagccctgtgcaacagggccttggtggccaggct
caggggcagccgaacagtacaaacatggccagcttaggtgccatgggcaagagccctctgaaccaaggagact
catcaacacccaacctgcccaaacaggcagccagcacctctgggcccactcccctgcctccaagcactgaat
ccacaagcacaaaagcaagtagggctggtgaccagtagtcctgccacatcacagactggacctgggatctgcat
gaatgctaacttcaaccagacccacccaggccttctcaatagtaactctggccatagcttaatgaatcaggctcaac
aagggcaagctcaagtcatgaatggatctcttggggctgctggaagaggaagggagctggaatgccctaccctg
ctccagccatgcagggggccacaagcagtgctggcggagaccttgacacaggtttccccacaaatggctggcc
atgctggactaaatacagcacaggcaggaggcatgaccaagatgggaatgactggtaccacaagtccatttgga
caaccctttagtcaaactggagggcagcagatgggagccactggagtgaaccccagttagccagcaaacaga
gcatggtcaatagtttacctgctttcctacagatatcaagaatacttcagtcaccactgtgccaaatatgtcccagttgc
aaacatcagtgggaattgtacccacacaagcaattgcaacaggccccacagcagaccctgaaaaacgcaaact
gatacagcagcagctggttctactgcttcatgcccacaaatgtcagagacgagagcaagcaaatggaggaggttcg
agcctgttctctcccacactgtcgaaccatgaaaaacgttttgaatcacatgacacattgtcaggctgggaaagcctg
ccaagtgcccattgtgcatcttcacgacaaatcatctctcattggaagaactgcacacgacatgactgtcctgtttgcc
tcccttttgaaaaatgccagtgacaagcgaaaccaacaaaccatcctgggatctccagctagtggaattcaaaaca
caattggttctgttggtgcagggcaacagaatgccacttcctaagtaacccaaatcccatagaccccagttccatgc
agcgggcctatgctgctctaggactcccctacatgaaccagcctcagacgcagctgcagcctcaggttcctggcca
gcaaccagcacagcctccagcccaccagcagatgaggactctcaatgccctaggaaacaaccccatgagtatc
ccagcaggaggaataacaacagatcaacagccaccaaacttgatttcagaatcagctcttccaacttccttggggg
ctaccaatccactgatgaatgatggttcaaactctggtaacattggaagcctcagcacgatacctacagcagcgcct
ccttccagcactggtgttcgaaaaggctggcatgaacatgtgactcaggacctacggagtcatctagtccataaact
cgttcaagccatcttcccaactccagacccctgcagctctgaaagatgccgcatggagaacctggttgcctatgcta
agaaagtggagggagacatgtatgagtctgctaaagcaggggatgaatactatcatttattagcagagaaaatctat
aaaatacaaaaagaactagaagaaaagcggggaggtcacgtttacataagcaaggcatcctgggtaaccagccag
ctttaccagcttctggggctcagccccctgtgattccaccagcccagtctgtaagacctccaaatgggcccctgcctt
gccagtgaatgcatgcaggtttctcaaggggatgaattcatttaacccaatgtccctgggaaacgtccagttgccaca
ggcacccatgggacctcgtgcagcctcccctatgaaccactctgtgcagatgaacagcatggcctcagttcgggt
atggccatttctccttcacggatgcctcagcctccaaatatgatgggcactcatgccaacaacattatggcccaggca
cctactcagaaccagttctgccacagaaccagttccatcatccagtggggcaatgagtgtgaacagtgtgggcat
gggcaaccagcagcccaggcaggtgttcacagggtcaggtacctggagctgctctcccctaacccctctgaacatg
ctggcacccaggccagccagctgccttgccaccagtgacacagtcaccattgcaccgactccacctctgctt
ccacagctgctggcatgccctctctccaacatccaacggcaccaggaatgacccctcctcagccagcagctccca
ctcagccatctactcctgtgtcatcgggcagactcctacccaactcctggctcagtgccagcgctgcccaaaca
cagagtacccctacagtccaggcagcagcacaggctcaggtgactccacagcctcagacccccagtgcagccac
catctgtggctactcctcagtcatcacagcagcaaccaacgcctgtgcatactcagcctcctggcacaccgcttctc
aggcagcagccagcattgataatagagtccctactccctcctctgtgaccagtgctgaaaccagttccagcagcc
aggaccccgatgtcccatgctggaaatgaagacagaggtgcagacagatgatgctgagcctgaacctactgaat
ccaaggggggaaacctcggtctgagatgatggaagaggatttacaaggttcttcccaagtaaaagaagacagata
cgacagagcagaagtcagagccaatggaagtagaagaaaagaacctgaagtaaagtggaagctaaagag
gaagaagagaacagttcgaacgacacagcctcacaatcaacatctccttcccagccacgcaaaaaaatctttaa
acccgaggagctacgccaggcacttatgccaactctagaagcactctatcgacaggacccagagtctttgccttttc
gtcagcctgtagatcctcagctcctaggaatcccagattattttgatatagtgaagaatcctatggacccttctaccatca
aacgaaagctggacacagggcaatatcaagaaccctggcagtatgtggatgatgtctggcttatgttcaacaatgc
gtggctatataatcgtaaaacgtcccgtgtatataaattttgcagtaaacttgcagaggtctttgaacaagaaattgacc
ctgtcatgcagtctcttggatattgctgtggacgaaagtatgagttctcccccacagacttgtgctgttacggaaagcag

Fig. 17 ctgtgtacaattcctcgtgatgcagcctactacagctatcagaataggtatcattctgtgagaagtgtttcacagagat
ccagggcgagaatgtgaccctgggtgacgacccttcccaacctcagacgacaatttccaaggatcaatttgaaaa
gaagaaaaatgataccttagatcctgaacctttgttgactgcaaagagtgtggccggaagatgcatcagattgtgtt
ctacactatgacatcattggccttcaggttttgtgtgtgacaactgtttgaagaaaactggcagacctcggaaagaaa
acaaattcagtgctaagaggctgcagaccacacgattgggaaaccacttagaagacagagtgaataagttttttgcg
gcgccagaatcaccctgaagctggggaggttttttgtcagagtggtggccagctcagacaagactgtggaggtcaa
gccgggaatgaagtcaaggtttgtggattctggagagatgtcggaatctttcccatatcgtaccaaagcactctttgctt
ttgaggagatcgatggagtcgatgtgtgcttttttgggatgcatgtgcaagaatacggctctgattgccccccaccaaa
tacaaggcgtgtatacatatcttatcggacagtattcatttcttccggcccgctgcctcggacagctgtttaccatga
gatcctcatcggatatctcgagtatgtgaagaaattggggtatgtgacaggacatatttgggcctgtcccccaagtga
aggagatgactatatcttttcattgccaccccctgaccagaaaatccccaaaccaaaacgactacaggagtggtac
aagaagatgctggacaaggcgtttgcagagaggatcattaacgactataaggacatcttcaaacaagcgaacga
agacaggctcacgagtgccaaggagttgccctattttgaaggagattctggcctaatgtgttggaagaaagcattaa
ggaactagaacaagaagaagaagaagaaggaaaaaagaagagagtactgcagcgagtgagactcctgagggc
agtcagggtgacagcaaaaatgcgaagaaaaagaacaacaagaagaccaacaaaaacaaaagcagcatta
gccgcgccaacaagaagaagcccagcatgcccaatgttccaacgacctgtcgcagaagctgtatgccaccatg
gagaagcacaaggaggtattcttttgtgattcatctgcatgctgggcctgttatcagcactcagccccccatcgtggac
cctgatcctctgcttagctgtgacctcatggatgggcgagatgccttcctcaccctggccagagacaagcactggga
attctcttccttacgccgctccaaatggtccactctgtgcatgctgtggagctgcacacacagggccaggaccgcttt
gtttatacctgcaatgagtgcaaacaccatgtggaaacacgctggcactgcactgtgtgtgaggactatgacctttgt
atcaattgctacaacacaaagagccacacccataagatggtgaagtgggggctaggcctagatgatgagggcag
cagtcagggtgagccacagtccaagagccccaggaatcccggcgtctcagcatccagcgctgcatccagtccct
ggtgcatgcctgccagtgtcgcaatgccaactgctcactgccgtcttgccagaagatgaagcgagtcgtgcagcac
accaagggctgcaagcgcaagactaatggaggatgcccagtgtgcaagcagctcattgctctttgctgctaccacg
ccaaaacactgccaagaaaataaatgccctgtgcccttctgcctcaacatcaaacataagctccgccagcagcaga
tccagcatcgcctgcagcaggctcagctcatgcgccggcgaatggcaaccatgaacacccgcaatgtgcctcag
cagagtttgccttctcctacctcagcaccacccggactcctacacagcagcccagcacaccccaaacaccacag
ccccagcccagcctcagccttcacctgttaacatgtcaccagctggcttccctaatgtagcccggactcagccccc
aacaatagtgtctgctgggaagcctaccaaccaggtgccagctcccccaccccctgcccagcccccaccctgcagc
agtagaagcagcccggcaaattgaacgtgaggcccagcagcagcagcacctataccgagcaaacatcaacaa
tggcatgccccaggacgtgcaggtatgggaccccaggaagccaaatgactcctgtgggcctgaatgtgccccg
tcccaaccaagtcagtgggcctgtcatgtctagtatgccacctgggcagtggcagcaggcacccatccctcagcag
cagccgatgccaggcatgcccaggcctgtaatgtccatgcaggcccaggcagcagtggctgggccacggatgcc
caatgtgcagccaccaaggagcatctcgccaagtgccctgcaagacctgctacggaccctaaagtcacccagct
ctcctcagcagcagcagcaggtgctgaacatccttaaatcaaacccacagctaatggcagctttcatcaaacagcg
cacagccaagtatgtggccaatcagcctggcatgcagccccagcccggacttcaatcccagcctggtatgcagcc
ccagcctggcatgcaccagcagcctagtttgcaaaacctgaacgcaatgcaagctggtgtgccacggcctggtgtg
cctccaccacaaccagcaatgggaggcctgaatccccagggacaagctctgaacatcatgaacccaggacaca
accccaacatgacaaacatgaatccacagtaccgagaaatggtgaggagacagctgctacagcaccagcagc
agcagcagcaacagcagcagcagcagcaacaacaaaatagtgccagcttggccgggggcatggcggga
cacagccagttccagcagccacaaggacctggaggttatgccccagccatgcagcagcaacgcatgcaacagc
acctccccatccagggcagctccatggggccagatggctgctccaatgggacaacttggccagatggggcagcctg
ggctaggggcagacagcacccctaatatccagcaggccctgcagcaacggattctgcagcagcagcagatgaa
gcaacaaatttgggtcaccaggccagccgaacccccatgagccccagcagcacatgctctcaggacagccaca
ggcctcacatctccctggccagcagatcgccacatcccttagtaaccaggtgcgatctccagccccgtgcagtctc
cacggccccaatcccaacctccacattccagcccgtcaccacggatacaaccccagccttcaccacaccatgttc
accccagactggttcccctcaccctggactcgcagtcaccatggccagctcatggatcaggacacctggggaa
ccctgaacagagtgcaatgctcccccagctgaatacccccaacaggagcgcactgtccagtgaactgtccctggtt
ggtgataccacgggagacacactagaaaagtttgtggagggttttgtag

Fig. 18

Mus musculus CREB binding protein (Crebbp) protein (2441 aa)

MAEMLLDGPPNPKRAKLSSPGFSANDNTDFGSLFDLENDLPDELIPNGELSLLNSGNLVPDAASKHKQLSELLRGGSGSSINPGIGNVSA
SSPVQQGSLGGQAGQGQPNSTNMASLGAMGKSPLNQGDSSTPNLPKQAASTSGETPRASQALNPQAQKQVGLVTSSPATSQTGPGICMNANF
MQTHPGLLNSNSGHSLMNQAQGQAQVTMNGSLGAAGRGRGAGMPYPAPAMQGATSSVLAETLTQVSPQMAGHAGLMTAQAGGMTKMGMTG
TTSPFGQPFSQTGGQQMGATGVNPQLASKQSMVNSLPAFPTDIKNTSVTTVPNMSQLQTSVGIVPTQAIATGPTADPEKRKLIQQQLVLL
LHAHKCQRREQANGEVTRACSLPHCRTMKNVLNHMTHCQAGKACQVAHCASSRQIISHWKNCTRHDCPVCLPLKNASDKRNQQTILGSPAS
GIQMTIGSVGAGQQNATSLSNPMPIDPSSMQRAYAALGLPYMNQPQTQLQPQVPGQQPAQQMRTLNALGMNPMSIPAGGITTDQQ
PPNLISESALPTSLGATNPLMNDGENSGNIGSLSTIPTAAPPSSTGVRKGWHEHVTQDLRSHLVHKLVQAIFPTPDPAALHDRRMENLVA
YAKRVEGMYESANSRDEYYHLLAEKIYKIQKELEEKRRSRLHKQGILGNQEALPASGAQPPVIPPAQSVRPPMGELPLPVNRMQVSQGM
MSFNPMSLGMVQLPQAPMGPRAASPMNHSVQMNSMASVPGMAISPSRMPQPFNMMGTHANNIMAQAPTQNQFLPQMQFPSSSGAMSVNSV
GMGQPAAQAGVSQGQVPGAALPNPLNMLAPQASQLPCPPVTQSPLHPTPPPASTAAGMPSLQHPTAPGMTPFQPAAPTQPSTPVSSGQTP
TPTPGSVPSAAQTQSTPTVQAAAQAQVTPQPQTPVQPPSVATPQSSQQPTFVHTQPPGTPLSQAASIDNRVPTPSSVTSAFTSSQSTSPSQ
PRKKIFKPEELRQAIMPTIFEALYRQDPESLPFRQPVDPQLLGIPDYFDIVKNPMDLSTIRKKLDTGQEFWQYVDDVWLMFNAWLYNR
KTSRVYKFCSKLAEVFEQEIDPVMQSLGYCCGRKYEFSPQILCCYGKQLCTIPRDAAYYSQNRYHFCEKCFTEIQGENVTLGDDPSQPQ
TTISKDQFEKKRMDTLDPEPFVDCKECGRKMHQICVLHYDIIWPSGFVCDNCLKKTGRPRKENKFSAKRLQTTRLGNHLEDEVNKFLRRQ
NHPEAGEVEVRVVASSDKTVEVKPGMKSRFVDSGEMSESFPYRTKALFAFEEIDGVDVCFFGMHVQEYGSDCPPPNTRRVYISYLDSIHF
FRPKCLRTAVYHEILIGYLEYVKKLGYVTGHIWACPPSEGDDYIFHCHPPDQKIPKPKRLQEWYKKMLDKAFAERIINDYKDIFKQANED
RLTSAKELPYFEGDFWPNVLEESIKELEQEEERKKEESTAASETPEGSGDSKNAKKKNMKKTNKNKSSISRANKKKPSMPNVSNDLSQ
KLYATMEKHKEVFFVIHLHAGPVISTQPPIVDPDPLLSCDLMDGRDAFLTLARDKHWEFSSLRRSKWSTLCMLVELHTQGQDRFVYTCNE
CKHHVETRWHCTVCEDYDLICINCYNTKSHTHKMVKWGLGLDDEGSSQGPQSKSPQESRRLSTQRCIQSIVHACQCRMANCSLPSCQKMK
RVVQHTKGCKRKTENGGCPVCKQLIALCCYHAKHCQEENKCPVPFCLNIRHKLRQQQIQHRLQQAQLMRRRMATMNTRNVPQQSLPSPFSAP
PGTPTQQPSTPQTPQQPPAQPQPSPVNMSPAGPPMVARTQPPTTVSAGKPTMQVPAPPPAQPPPAAVEAARQIEREAQQQQHLYRANINN
CMPPGRAGMGTPGSQMTPVGLNVPRPNQVSGPVMSSMPPGQWQQAPIFQQQEMPGMPRPVMSMQAQAVAGPRMPNVQPPRSISPSALQD
LLRTLKSPSSPQQQQVLNILKSNPQLMAAFIKQRTAKYVANQPGMQPQPGLQSQPGMQPQPGMHQQPSLQNLNAMQAGVPRPGVPPFQP
AMGGLNPGQALNIMNPGHNPNMTAMMNPQYREMVRRQLLQHQQQQQQQQQQQQQNSASLAGGMAGHSQFQQPQPGSGYAPAMQQRMQ
QHLPIQGSSMGQMAAPMGQLGNGQPGLGADSTPNIQQAHQQRILQQQMKQQIGSPGQPNPMSPQQHMILSGQPQASHLPGQQIATSLSN
QVRSPAPVQSPRPQSQPPHSSPSPRIQPSPHPQPSPHHVSPQTGSPHPGLAVTMASSMDQGHLGNPEQSAMLPQLNTPNRSALSELSWGDTT
GDTLEKFVEGL*

Fig. 19

Homo sapience CREB binding protein (Crebbp) mRNA (7329 bp)

atggctgagaacttgctggacggaccgcccaacccaaaagagccaaactcagctcgcccggtttctcggcgaatgac
agcacagattttggatcattgtttgacttggaaaatgatcttcctgatgagctgatacccaatggaggagaattaggccttttaa
acagtgggaaccttgttccagatgctgcttccaaacataaacaactgtcggagcttctacgaggaggcagcggctctagta
tcaacccaggaataggaaatgtgagcgccagcagcccgtgcagcagggcctgggtggccaggctcaagggcagcc
gaacagtgctaacatggccagcctcagtgccatgggcaagagccctctgagccagggagattcttcagcccccagcctg
cctaaacaggcagccagcacctctgggcccaccccgctgcctcccaagcactgaatccgcaagcacaaaagcaagt
ggggctggcgactagcagccctgccacgtcacagactggacctggtatctgcatgaatgctaactttaaccagacccacc
caggcctcctcaatagtaactctggccatagcttaattaatcaggcttcacaagggcaggcgcaagtcatgaatggatctct
tggggctgctggcagaggaagggagctggaatgccgtacccactccagccatgcagggcgcctcgagcagcgtgct
ggctgagacccTaacgcaggtttccccgcaaatgactggtcacgcgggactgaacacgcacaggcaggaggcatgg
ccaagatgggaataactggaacacaagtccattggacagccctttagtcaagctggagggcagccaatgggagcca
ctggagtgaaccccagttagccagcaaacagagcatggtcaacagtttgcccaccttccctacagatatcaagaatactt
cagtcaccaacgtgccaaatatgtctcagatgcaaacatcagtgggaattgtacccacacaagcaattgcaacaggccc
cactgcagatcctgaaaaacgcaaactgatacagcagcagctggttctactgcttcatgctcataagtgtcagagacgag
agcaagcaaacgga[?]aggttcgggcctgctcgctcccgcattgtcgaaccatgaaaaacgttttgaatcacatgacgcat
tgtcaggctgggaaagcctgccaagttgccccattgtgcatcttcacgacaaatcatctctcattggaagaactgcacacgac
atgactgtcctgtttgcctcccttgaaaaatgccagtgacaagcgaaaccaacaaaccatcctgggtctccagctagtgg
aattcaaaacacaattggttctgttggcacagggcaacagaatgccacttctttaagtaacccaaatcccatagaccccag
ctccatgcagcgagcctatgctgctctcggactccctacatgaaccagccccagacgcagctgcagcctcaggttcctg
gccagcaaccagcacagcctcaaacccaccagcagatgaggactctcaaccccctgggaaataatccaatgaacattc
cagcaggaggaataacaacagatcagcagcccccaaacttgatttcagaatcagctcttccgacttccctgggggccac
aaacccactgatgaacgatggctccaactctggtaacattggaaccctcagcactataccaacagcagctcctccttctag
caccggtgtaaggaaaggctggcacgaacatgtcactcaggacctgcggagccatctagtgcataaactcgtccaagcc
atcttcccaacacctgatcccgcagctctaaaggatcgccgcatggaaaacctggtagcctatgctaagaaagtggaag
gggacatgtacgagtctgccaacagcagggatgaatattatcacttattagcagagaaaatctacaagatacaaaaaga
actagaagaaaaacggaggtcgcgtttacataaacaaggcatcttggggaaccagccagccttaccagccccgggggg
ctcagccccctgtgattccacaggcacaacctgtgagacctccaaatggacccctgtccctgccagtgaatcgcatgcaa
gtttctcaagggatgaattcattaaccccatgtccttggggaacgtccagttgccacaagcacccatgggacctcgtgcag
cctccccaatgaaccactctgtccagatgaacagcatgggctcagtgccagggatggccatttctccttcccgaatgcctca
gcctccgaacatgatgggtgcacacaccaacaacatgatggcccaggcgccgctcagagccagttctgccacagaa
ccagttcccgtcatccagcggggcgatgagtgtgggcatggggcagccgccagcccaaacaggcgtgtcacagggac
aggtgcctggtgctgctcttcctaaccctctcaacatgctggggcctcaggccagccagctacctgccctccagtgacaca
gtcaccactgcacccaacaccgcctcctgctccacggctgctggcatgccatctctccagcacacgacaccacctggga
tgactcctcccagccagcagctcccactcagccatcaactctgtgtcgtcttccgggcagactcccaccccgactcctg
gctcagtgcccagtgctacccaaacccagagcacccctacagtccaggcagcagccaggccaggtgaccccgca
gcctcaaacccagttcagccccgtctgtggctacccctcagtcatcgcagcaacagccgacgcctgtgcacgcccag
cctcctggcacaccgcttctcccaggcagcagccagcattgataacagagtccctaccccctcctggtggccagcgcag
aaaccaattcccagcagccaggacctgacgtacctgtgctggaaatgaagacggagacccaagcagaggacactga
gcccgatcctggtgaatccaaaggggagcccaggtctgagatgatggaggaggatttgcaaggagcttcccaagttaaa
gaagaaacagacatagcagagcagaaatcagaaccaatggaagtggatgaaaagaaacctgaagtgaaagtagaa
gttaagagggaagaagagagtagcagtaacggcacagcctctcagtcaacatctccttcgcagccgcgcaaaaaaatc
tttaaaccagaggagttacgccaggccctcatgccaaccctagaagcactgtatgacaggacccagagtcattacttc
cggcagcctgtagatcccagctcctcggaattccagactatttgacatgtaaagaatcccatggacctctccaccatca
agcggaagctggacacagggcaataccaagagccctggcagtacgtggacgacgtctggctcatgttcaacaatgcct
ggctctataatcgcaagacatcccgagtctataagttttgcagtaagcttgcagaggtctttgagcaggaaattgaccctgtc

Fig. 20 atgcagtcccttggatatgctgtggacgcaagtatgagttttccccacagactttgtgctgctatgggaagcagctgtgtacc
attcctcgcgatgctgcctactacagctatcagaataggtatcatttctgtgagaagtgtttcacagagatccagggcgagaa
tgtgaccctgggtgacgaccettcacagccccagacgacaattteaaaggatcagtttgaaaagaagaaaaatgatacct
tagaccccgaaccttcgttgattgcaaggagtgtggccggaagatgcatcagatttgcgttctgcactatgacatcatttggc
cttcaggttttgtgtgcgacaactgcttgaagaaaactggcagacctcgaaaagaaaacaaattcagtgctaagaggctg
cagaccacaagactgggaaaaccacttggaagaccgagtgaacaaattttttgcggcgccagaatcaccctgaagccgg
ggaggttttttgtccgagtggtggccagctcagacaagacggtggaggtcaagcccgggatgaagtcacggtttgtggattc
tggggaaatgtctgaatctttcccatatcgaaccaaagctctgtttgcttttgaggaaattgacggcgtggatgtctgcttttttgg
aatgcacgtccaagaatacggctctgattgcccccctccaaacacgaggcgtgtgtacatttcttatctggatagtattcatttc
ttccggccacgttgcctccgcacagccgtttaccatgagatccttattggatatttagagtatgtgaagaaattagggtatgtga
cagggcacatctgggcctgtcctccaagtgaaggagatgattacatcttccattgccaccccacctgatcaaaaaatacca
agccaaaacgactgcaggagtggtacaaaaagatgctggacaaggcgtttgcagagcggatcatccatgactacaag
gatattttcaaacaagcaactgaagacacggctcaccagtgccaaggaactgcccctattttgaaggtgattctggcccaatg
tgttagaagagagcattaaggaactagaacaagaagaagaggagaggaaaaaggaagagagcactgcagccagtg
aaaccactgagggcagtcagggcgacagcaagaatgccaagaagaagaacaacaagaaaaccaacaagaacaa
aagcagcatcagccgcgccaacaagaagaagcccagcatgcccaacgtgtccaatgacctgtcccagaagctgtatg
ccaccatggagaagcacaaggaggtcttcttcgtgatccacctgcacgctgggcctgtcatcaacaccctgccccccatc
gtcgaccccgaccccctgctcagctgtgacctcatgatgggcgcgacgcctcctcacctcgccagagacaagcact
gggagttctcctccttgcgccgctccaagtggtccacgctctgcatgctggtggagctgcacacccagggccaggacgct
ttgtctacacctgcaacgagtgcaagcaccacgtggagacgcgctggcactgcactgtgtgcgaggactacgacctctgc
atcaactgctataacacgaagagccatgcccataagatggtgaagtggggctgggcctggatgacgacggcagcagc
cagggcgagccacagtcaaagagccccaggagtcacgccggctgagcatccagcgctgcatccagtcgctggtgca
cgcgtgccagtgccgcaacgccaactgctcgctgccatcctgccagaagatgaagcgggtggtgcagcacaccaagg
gctgcaaacgcaagaccaacgggggctgcccggtgtgcaagcagctcatcgccctctgctgctaccacgccaagcact
gccaagaaaacaaatgcccgtgcccttctgcctcaacatcaaacacaagctccgccagcagcagatccagcaccgc
ctgcagcaggcccagctcatgcgccggcggatggccaccatgaacacccgcaacgtgcctcagcagagtctgccttctc
ctacctcagcaccgccgggaccccccacacagcagcccagcacacccagacgccgcagccccctgcccagcccc
aaccctcacccgtgagcatgtcaccagctggcttccccagcgtggcccggactcagccccccaccacggtgtccacagg
gaagcctaccagccaggtgccggccccccaccccggcccagcccctcctgcagcggtggaagcggctcggcag
atcgagcgtgaggcccagcagcagcagcacctgtaccgggtgaacatcaacaacagcatgccccaggacgcacgg
gcatggggaccccggggagccagatggccccgtgagcctgaatgtgccccgacccaaccaggtgagcgggccgtc
atgcccagcatgcctccgggcagtggcagcaggcgccccttccccagcagcagcccatgccaggcttgcccaggcct
gtgatatccatgcaggccaggcggccgtggctgggccccggatgcccagcgtgcagccacccaggagcatctcaccc
agcgctctgcaagacctgctgcggaccctgaagtgcccagctccctcagcagcaacagcaggtgctgaacattctca
aatcaaacccgcagctaatggcagctttcatcaaacagcgcacagccaagtacgtggccaatcagcccggcatgcagc
cccagcctggcctccagtcccagcccggcatgcaaccccagcctggcatgcaccagcagcccagcctgcagaacctg
aatgccatgcaggctggcgtgcgcggccccggtgtgcctccacagcagcaggcgatgggaggcctgaaccccagggg
ccaggccttgaacatcatgaacccaggacacaaccccaacatggcgagtatgaatccacagtaccgagaaatgttacg
gaggcagctgctgcagcagcagcagcaacagcagcagcaacaacagcagcaacagcagcagcagcaagggagt
gccggcatggctggggcatggcgggcacggccagttccagcagcctcaaggaccggaggctacccaccggcca
tgcagcagcagcagcgcatgcagcagcatctcccctccagggcagctccatgggccagatggcggctcagatggga
cagcttggccagatgggcagccgggctggggcagacagcaccccaacatccagcaagccctgcagcagcgg
attctgcagcaacagcagatgaagcagcagattgggtcccaggccagccgaaccccatgagccccagcaacacat
gctctcaggacagccacaggcctcgcatctccctggccagcagatgccacgtcccttagtaaccaggtgcggtctccag
cccctgtccagtctccacggccccagtcccagcctccacattccagccgtcaccacggatacagcccagccttcgcca
caccacgtctcacccagactggttccccccaccccggactcgcagtcaccatggccagctccatagatcagggacactt
ggggaaccccgaacagagtgcaatgctcccccagctgaacaccccagcaggagtgcgctgtccagcgaactgtccct
ggtcggggacaccacggggacacgctagagaagtttgtggagggcttgtag

Fig. 21

Homo sapience CREB binding protein (Crebbp) protein (2442 aa)

MAENLLDGPPNPKRAKLSSPGFSANDSTDFGSLFDLENDLPDELPNGGELGLLNSGNLVPDAASKHKQLSELLRGGSGSSINPGIGNVSASSPVQQGLGG
QAGGQPNSANMASLSAMGKSPLSQGDSSAPSLPKQAASTSGPTPAASQALNPQAQKQVGLATSSPATSQTGPCICMNANFNQTHPGLLNSNSGHSLI
NQASQGQAQVMNGSLGAAGRGRGAGMPYPTPAMQGASSVLAETLTQVSPQMTGHAGLNTAQAGGMAKMGITGNTSPFGQPFSQAGGQPMGA
TGVNPQLASKQSMVNSLPTFPTFDIKNTSVTNVPNMSQMQTSVGIVPTQAIATGPTADFEKRKLIQQQLVLLLHAHKCQRREQANGEVRACSLPHCRTMK
NVLNHMTHCQAGKACQVAHCASSRQIISHWKNCTRHDCPVCLPLKNASDKRNQQTILGSPASGIQNTIGSVGTGQQNATSLSNPNPIDPSSMQRAYAA
LGLPYMNQFQTQLQPQVPGQPQTHQQMRTLNPLGNNPMNIPAGGITTDCQPPMLISESALPTSLGATNPLMNDGSNSGNIGTLSTPTAAPPSS
TGVRKGWHEHVTQDLRSHLVHKLVQAIFPTDPAALKDRRMENLVAYAKKVEGDMYESANSRDEYYHLLAEKIYKIQKELEEKRRSRLHKQGILGNQPALP
APGAQPPVIPQAQPVRPPNGPLSLPVNRMQVSCGMNSFNPMSLGNVQLPQAPMGPRAASPMNHSVQMNSMGSVPGMAISPSRMPQPPNMMG
AHTNNMMAQAPAQSQFLPQNQFPSSSGAMSVGMGQPPAQTGVSQGQVPGAALPNPLNMLGPQASQLPCPPVTQSPLHPTPPPASTAAGMPSLQH
TTPPGMTPPQPAAPTQPSTPVSSSGQTPTPTPGSVPSATQTQSTPTVQAAAQAQVTPQPQTPVQPPSVATPQSSQQPTPVHAQPPGTPLSQAAASID
NRVPTPSSVASAETNSQQPGPQVPVLEMKTETQAEDTEPDPGESKGEPRSEMMEEDLQGASQVKEETDIAEQKSEPMEVDEKKPEVKVEKEEESSSN
GTASQSTSPSQPRKKIFKPEELRQALMPTLEALYRQDPESLPFRQPVDPQLLGIPDYFDIVKNPMDLSTIKRKLDTGQYQEPWQYVDDVWLMFNNAWLY
NRKTSRVYKFCSKLAEVFEQEIDPVMQSLGYCCGRKYEFSPQTLCCYGKRYHFCEKCFTEIQGENVTLGDDPSQPQTTISKDQFEK
KKNDTLDPEPFVDCKECGRKMHQICVLHYDIIWPSGFVCDNCLKKTGRPRKENKFSAKRLQTTRLGNHLEDRVNKFLRRQNHPLAGEVFVRVVASSDKTV
EVKPGMKSRFVDSGEMSESFPYRTKALFAFEEIDGVDVCFFGMHVQEYGSDCPPPNTRRVVYISYLDSIHFFRPRQLRTAVYHEILIGYLEYVKKLGYTGHIW
ACPPSEGDDYIFHCHPPDQKIPKPKRLQEWYKKMLDKAFAERIIHDYKDIFKQATEDRLTSAKELPYFEGDFWPNVLEESIKELQEEEERKKEESTAASETTE
GSQGDSKNAKKKNKKTNKNKSSISRANKKKPSMPNVSNDLSQKLYATMEKHKEVFFVIHLHAGPVINTLPPIVDPDPLLSCDLMDGRDAFLTLARDKH
WEFSSLRRSKWSTLCMLVELHTQGQDRFVYTCNECKHHVETRWHCTVCEDYDLCINCYNTKSHAHKMVKWGLGLDDEGSSQGEPQSKSPQESRRLSIQ
RCIQSLVHACQCRNANCSLPSCQRMKRVVQHTKGCKRKTNGGCPVCKQLIALCCYHAKHCQENKCPVPFCLNIKHKLRQQQJQHRLQQAQLMRRRMA
TMNTRNVPQQSLPSPTSAPPGTPTQQPSTPQTPQPPAQPQPSPVSMSPAGFPSVARTQPFTTVSTGKPTSQVPAPPPAQPPPAAVEAARQJREAQQ
QQHLYRVNINSMPPGRTGMGTPGSQMAPVSLNVPRPNQVSGPVMPSMPPGQWQQAPLPQQQPMPGLPRPVISMQAQAAVAGPRMPSVQPPR
SISPSALODLLRTLKSPSSPQQQQQVLNILKSNPQLMAAFIKQRTAKYVANQPGMQPQGLQSQPGMQPQPGMHQQPSLQNILNAMQAGVPRPGVP
PQQQAMGGLNPQGQALNIMNFGHNPNMRASMNPQYREMLRRQLLQQQQQQQQQQQQQQQQGSAGMAGGMAGHGQFQQPQGGYP
PAMQQQRMQQHLPLQGSSMGQMAAQMGQLGQMGQPGLGADSTPNIQQALQQRILQQQQMKQQIGSPGQPNPMSPQQHMLSGQPQASHL
PGQQIATSLSNQVRSPAPVQSPRPQSQPPHSSPSPRIQPQPSPHHVSPQTIGSPHPGLAVTMASSIDQGHLGNPEQSAMLPQLNTPSRSALSSELSLVGDT
TGDTLEKFVEGL*

Fig. 22

Mus musculus CREB binding protein (Crebbp) mutant protein (386 aa)

MAENLLDGPPNPKRAKLSSPGFSANDNTDFGSLFDLENDLPDELIPNGELSLLNSGNLV
PDAASKHKQLSELLRGGSGSSINPGIGNVSASSPVQQGLGGQAQGQPNSTNMASLGAMG
KSPLNQGDSTPNLPKQAASTSGPTPASQALNPQAQKQVGLVTSSPATSQTGPGICMN
ANFNQTHPGLLNSNSGHSLMNQAQQGQAQVMNGSLGAAGRGRGAGMPYPAPAMQGATSS
VLAETLTQVSPQMAGHAGLNTAQAGGMTKMGMTGTTSPFGQPFSQTGGQMGATGVNPQ
LASKQSMVNSLPAFPTDIKNTSVTTVPNMSQLQTSVGIVPTQAIATGPTADPEKRKLIQ
QQLVLLHAHKCQRREQANGRFEPVLSHTVEP*

Homo sapience CREB binding protein (Crebbp) mutant protein (387 aa)

MAENLLDGPPNPKRAKLSSPGFSANDSTDFGSLFDLENDLPDELIPNGGELGLLNSNGL
VPDAASKHKQLSELLRGGSGSSINPGIGNVSASSPVQQGLGGOAQGQPNSANMASLSAM
GKSPLSQGDSSAPSLPKQAASTSGPTPAASQALNPQAQKQVGLATSSPATSQTGPGICM
NANFNQTHPGLLNSNSGHSLINQASQGQAQVMNGSLGAAGRGRGAGMPYPTPAMQGASS
SVLAETLTQVSPQMTGHAGLNTAQAGGMAKMGITGNTSPFGQPFSQAGGQPMGATGVNP
QLASKQSMVNSLPTFPTDIKNTSVTNVPNMSQMQTSVGIVPTQAIATGPTADPEKRKLI
QQQLVLLHAHKCQRREQANGRFGPARSRIVEP*

Fig. 23

Alignment of mouse Crebbp mRNA

```
              1081                                                1123
               |                                                   |
crebbpwt       CTTCATGCCACAAATGTCAGAGACGAGAGCAAGCAAATGGAGAGGTTCGAGCCTGTTCT
crebbpmutant   CTTCATGCCACAAATGTCAGAGACGAGAGCAAGCAAATGGA-AGGTTCGAGCCTGTTCT
               ****************************************  *****************
                                                       ↑
                                                   single base deletion
```

Alignment of mouse Crebbp protein

```
              361         374
               |           |
crebbpwt       LHAHKCQRREQANGEVRACSLPHQRTMKNVLNHMTHCQAGKACQVAHCASSRQIISHWKN
crebbpmutant   LHAHKCQRREQANGRFEPVLSHTVEP...
               **************
```

Fig. 24

Alignment of human Crebbp mRNA

```
                  1081                                                              1126
                  |                                                                 |
crebbpwt          CTGCTTCATGCTCATAAGTGTCAGAGAGAGAGCAAGCAAACGGAGAGGTTCGGGCCTGC
crebbpmutant      CTGCTTCATGCTCATAAGTGTCAGAGAGAGAGCAAGCAAACGGA-AGGTTCGGGCCTGC
                  ************************************************ **********
                                                                  ↑
                                                           single base deletion
```

Alignment of human Crebbp protein

```
                  361                                                375
                  |                                                  |
crebbpwt          LLHAHKCQRREQANGEVRACSLPHQRTMKMVLNHMTHCQAGKACQVAHCASSRQIISHWK
crebbpmutant      LLHAHKCQRREQANGRFGPARSRIVEP..:
                  ***************
```

TRANSGENIC ANIMAL HAVING CREBBP GENE INTO WHICH MUTATION HAS BEEN INTRODUCED

TECHNICAL FIELD

This application claims the benefit of priority of Japanese Patent Application No. 2018-124666, the entire contents of which are incorporated herein by reference.

The disclosure relates to a transgenic animal having the CREBBP gene into which a mutation has been introduced, a method of producing the same, use thereof as a disease model, or a method of determining a disease on the basis of the presence or absence of the mutation.

BACKGROUND

Rubinstein-Taybi syndrome is a multiple malformation syndrome characterized by features such as psychomotor retardation, specific facial characteristics, and broad thumb-hallux. The CREB-binding protein (CBP or CREBBP) gene located at 16p13.3 was identified as the disease gene and most cases are sporadic (Non-Patent Literature 1-18). CREBBP is a histone acetyltransferase and Rubinstein-Taybi syndrome is considered to be a disorder of histone acetylation. No radical treatment is currently available and complications are treated at an early stage to improve long-term prognosis.

A mouse in which a wide region of the CREBBP gene is artificially knocked out is known as a model animal of Rubinstein-Taybi syndrome (Non-Patent Literature 19). The causative site in the gene has not been identified in this model. It is not known whether this model reflects a mutation that occurs in nature.

REFERENCES

Non-Patent Literature

[Non-Patent Literature 1] Alari V, et al., "iPSC-derived neurons of CREBBP- and EP300-mutated Rubinstein-Taybi syndrome patients show morphological alterations and hypoexcitability" Stem Cell Research, 2018 May 30; 30:130-140

[Non-Patent Literature 2] Merk D J, et al., "Opposing Effects of CREBBP Mutations Govern the Phenotype of Rubinstein-Taybi Syndrome and Adult SHH Medulloblastoma" Developmental Cell, 2018 Mar. 26; 44(6):709-724.e6

[Non-Patent Literature 3] Menke L A, et al., "Further delineation of an entity caused by CREBBP and EP300 mutations but not resembling Rubinstein-Taybi syndrome" American Journal of Medical Genetics Part A, 2018 April; 176(4):862-876

[Non-Patent Literature 4] Eser M, et al., "A case with Rubinstein-Taybi syndrome: A novel frameshift mutation in the CREBBP gene" The Turkish Journal of Pediatrics, 2017; 59(5):601-603

[(Non-Patent Literature 5] Rokunohe D, et al., "Rubinstein-Taybi syndrome with multiple pilomatricomas: The first case diagnosed by CREBBP mutation analysis" Journal of Dermatological Science, 2016 September; 83(3):240-2

[Non-Patent Literature 6] Menke L A, et al., "CREBBP mutations in individuals without Rubinstein-Taybi syndrome phenotype" American Journal of Medical Genetics Part A, 2016 October; 170(10):2681-93

[Non-Patent Literature 7] de Vries T I, et al., "Mosaic CREBBP mutation causes overlapping clinical features of Rubinstein-Taybi and Filippi syndromes" European Journal of Human Genetics, 2016 August; 24 (9):1363-6

[Non-Patent Literature 8] Wincent J, et al., "CREBBP and EP300 mutational spectrum and clinical presentations in a cohort of Swedish patients with Rubinstein-Taybi syndrome" Molecular Genetics & Genomic Medicine, 2015 Sep. 22; 4(1):39-45

[Non-Patent Literature 9] Kamenarova K, et al., "Identification of a novel de novo mutation of CREBBP in a patient with Rubinstein-Taybi syndrome by targeted next-generation sequencing: a case report" Human Pathology, 2016 January; 47(1):144-9

[Non-Patent Literature 10] Huh R, et al., "Letter to the Editor: A Novel Mutation in the CREBBP Gene of a Korean Girl with Rubinstein-Taybi syndrome" Annals of Clinical & Laboratory Science, 2015 Summer; 45(4):458-61

[Non-Patent Literature 11] Rusconi D, et al., "Characterization of 14 novel deletions underlying Rubinstein-Taybi syndrome: an update of the CREBBP deletion repertoire" Human Genetics, 2015 June; 134(6):613-26

[Non-Patent Literature 12] Yoo H J, et al., "Whole exome sequencing for a patient with Rubinstein-Taybi syndrome reveals de novo variants besides an overt CREBBP mutation" International Journal of Molecular Sciences, 2015 Mar. 11; 16(3):5697-713

[Non-Patent Literature 13] Spena S, et al., "Insights into genotype-phenotype correlations from CREBBP point mutation screening in a cohort of 46 Rubinstein-Taybi syndrome patients" Clinical Genetics, 2015 November; 88(5):431-40

[Non-Patent Literature 14] Kim S R, et al., "Cryptic microdeletion of the CREBBP gene from t(1; 16) (p36.2; p13.3) as a novel genetic defect causing Rubinstein-Taybi syndrome" Annals of Clinical & Laboratory Science, 2013 Fall; 43(4):450-6

[Non-Patent Literature 15] Marzuillo P, et al., "Novel cAMP binding protein-BP (CREBBP) mutation in a girl with Rubinstein-Taybi syndrome, GH deficiency, Arnold Chiari malformation and pituitary hypoplasia" BMC Medical Genetics, 2013 Feb. 23; 14:28

[Non-Patent Literature 16] Lai A H, et al., "A submicroscopic deletion involving part of the CREBBP gene detected by array-CGH in a patient with Rubinstein-Taybi syndrome" Gene, 2012 May 10; 499(1):182-5

[Non-Patent Literature 17] Caglayan A O, et al., "A boy with classical Rubinstein-Taybi syndrome but no detectable mutation in the CREBBP and EP300 genes" Genetic counseling, 2011; 22(4):341-6

[Non-Patent Literature 18] Li C, Szybowska M. "A novel mutation c.4003 G>C in the CREBBP gene in an adult female with Rubinstein-Taybi syndrome presenting with subtle dysmorphic features" American Journal of Medical Genetics Part A, 2010 November; 152A(11):2939-41

[Non-Patent Literature 19] Oike Y, et al., "Mice homozygous for a truncated form of CREB-binding protein exhibit defects in hematopoiesis and vasculo-angiogenesis" Blood, 1999 May 1; 93(9):2771-9

SUMMARY

An object of the disclosure relates to a transgenic animal having the CREBBP gene into which a mutation has been introduced. A further object of the disclosure relates to a method of determining a disease on the basis of the presence or absence of the mutation.

The inventors found that small mice spontaneously generated during breeding exhibited symptoms of Rubinstein-Taybi syndrome and advanced sleep phase syndrome, and had a specific single nucleotide deletion in the CREBBP gene. Furthermore, when the single nucleotide deletion was introduced into the genomes of mice, the mice exhibited similar symptoms.

Accordingly, an aspect of the disclosure provides a non-human transgenic animal having at least one CREBBP gene locus into which a mutation has been introduced, wherein the mutated CREBBP gene encodes a mutant CREBBP consisting of an amino acid sequence having at least 90% identity with the amino acid sequence of SEQ ID NO: 5.

An aspect of the disclosure provides a method of producing the transgenic animal comprising introducing a mutation into at least one CREBBP gene locus of a non-human animal.

An aspect of the disclosure provides use of the transgenic animal as a model of Rubinstein-Taybi syndrome or a model of advanced sleep phase syndrome.

An aspect of the disclosure provides a peptide consisting of an amino acid sequence having at least 90% identity with the amino acid sequence of SEQ ID NO: 5 or a polynucleotide encoding the peptide.

An aspect of the disclosure provides a method of determining Rubinstein-Taybi syndrome, comprising:
(1) determining a nucleotide sequence of the CREBBP gene in a nucleic acid sample obtained from a subject;
(2) determining the amino acid sequence encoded by the nucleotide sequence; and
(3) determining that the subject is suffering or will suffer from Rubinstein-Taybi syndrome when the amino acid sequence has at least 90% identity with the amino acid sequence of SEQ ID NO: 5 or 6.

An aspect of the disclosure provides a method of determining Rubinstein-Taybi syndrome, comprising:
(1) determining whether the CREBBP gene in a nucleic acid sample obtained from a subject lacks a nucleotide corresponding to position 1123 of SEQ ID NO: 1 or position 1126 of SEQ ID NO: 3; and
(2) determining that the subject is suffering or will suffer from Rubinstein-Taybi syndrome when the CREBBP gene lacks the nucleotide.

The transgenic animal having the mutation as disclosed herein is useful as a model of Rubinstein-Taybi syndrome or advanced sleep phase syndrome. Furthermore, Rubinstein-Taybi syndrome or advanced sleep phase syndrome of a subject may be determined on the basis of the presence or absence of the mutation.

BRIEF DESCRIPTION OF DRAWINGS

FIG. 16 shows the nucleotide sequence of the wild-type mouse CREBBP gene. The guanine nucleotide at position 1123, which is absent in the mutant CREBBP gene, is indicated in the square.
FIG. 17 shows the nucleotide sequence of the wild-type mouse CREBBP gene, following to FIG. 16.
FIG. 18 shows the amino acid sequence of the wild-type mouse CREBBP.
FIG. 19 shows the nucleotide sequence of the wild-type human CREBBP gene. The guanine nucleotide at position 1126, which corresponds to the guanine nucleotide at position 1123 absent in the mutant mouse CREBBP gene, is indicated in the square.
FIG. 20 shows the nucleotide sequence of the wild-type human CREBBP gene, following to FIG. 19.
FIG. 21 shows the amino acid sequence of the wild-type human CREBBP.
FIG. 22 shows the amino acid sequences of the mutant mouse CREBBP and the mutant human CREBBP. The asterisks indicate the positions of the stop codons.
FIG. 23 shows a part of the alignments of the nucleotide and amino acid sequences of the wild-type mouse CREBBP and the mutant mouse CREBBP. The sequence frameshifted due to the single base deletion is indicated in the square.
FIG. 24 shows a part of the alignments of the nucleotide and amino acid sequences of the wild-type human CREBBP and the mutant human CREBBP. The sequence frameshifted due to the single base deletion is indicated in the square.

DETAILED DESCRIPTION

Figure 1:
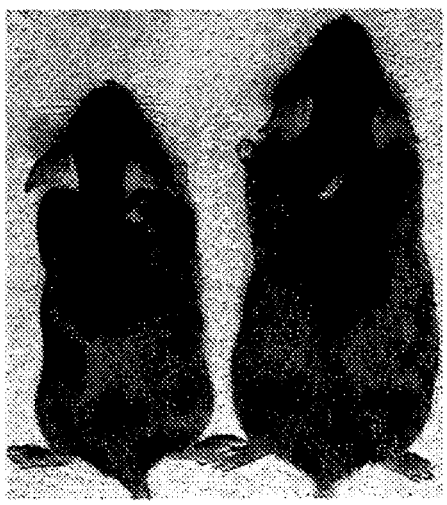
FIG. 1 shows a representative appearance of the dwarf mice.
Figure 1:
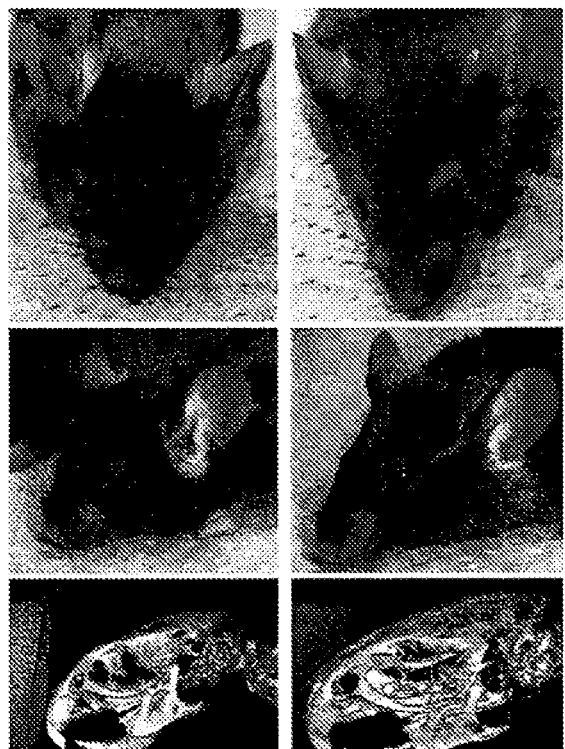

When a numerical value is accompanied with the term "about", the value is intended to represent any value in the range of −10% of the value to +10% of the value. For example, "about 20" means "a value from 18 to 22." A range defined with values of the lower and upper limits covers all values from the lower limit to the upper limit, including the values of the both limits. When a range is accompanied with the term "about", the both limits are read as accompanied with the term. For example, "about 20 to 30" is read as "18 to 33."

Unless otherwise defined, the terms used herein are read as generally understood by a skilled person in the technical fields such as organic chemistry, medical sciences, pharmaceutical sciences, molecular biology, and microbiology. Several terms used herein are defined as described below. The definitions herein take precedence over the general understanding.

CREBBP is a transcriptional coactivator present in almost all cells, activating transcription through a protein-protein interaction without directly binding to DNA. CREBBP is activated by binding to phosphorylated CREB via the KIX domain. The activated CREBBP promotes transcription through interaction with RNA polymerase via TFIIB, a general transcription factor of the transcription complex. Besides the phosphorylated CREB, CREBBP is a transcriptional coactivator common to many transcription factors such as nuclear hormone receptors, Myb, Fos, Jun, and STST 1α. In addition, CREBBP has HAT activity, being responsible for histone acetylation and the resulting chromatin structure control to activate transcription.

"CREBBP" and "CREBBP gene" as disclosed herein may be of any species, typically a mammal, e.g., mouse, rat, hamster, rabbit, cat, dog, cow, sheep, monkey, or human, particularly a rodent such as a mouse or a primate such as a human. A typical nucleotide sequence of the mouse wild-type CREBBP gene is represented by SEQ ID NO: 1. The gene encodes the wild-type CREBBP having the amino acid sequence of SEQ ID NO: 2 consisting of 2441 amino acids. The mouse CREBBP gene is located in 16qA1. A typical nucleotide sequence of the human wild-type CREBBP gene is represented by SEQ ID NO: 3. The gene encodes the wild-type CREBBP having the amino acid sequence of SEQ ID NO: 4 consisting of 2442 amino acids. The human CREBBP gene is located in 16p13.3.

The CREBBP gene may have a nucleotide sequence that hybridizes to a polynucleotide having the nucleotide sequence complement to the nucleotide sequence of SEQ ID NO: 1 or 3 under a stringent condition. Regarding "hybridize under a stringent condition", the hybridization can be carried out according to any conventional method, for example, those described in Molecular Cloning, T. Maniatis et al., CSH Laboratory (1983). The stringent condition may be a condition where the hybridization is conducted in a solution containing 6×SSC and 50% formamide at 45° C., wherein 10×SSC is a solution containing 1.5 M NaCl and 0.15 M trisodium citrate, followed by washing in 2×SSC at 50° C. (Molecular Biology, John Wiley & Sons, N. Y. (1989), 6.3.1-6.3.6) or a condition that provides an equivalent stringency. The CREBBP gene may have a nucleotide sequence having at least 70%, 80%, 85%, 90%, 95%, 96%, 97%, 98%, or 99% sequence identity with the nucleotide sequence of SEQ ID NO: 1 or 3.

The mutant CREBBP as disclosed herein has an amino acid sequence having at least 70%, 80%, 85%, 90%, 95%, 96%, 97%, 98%, or 99% identity with the amino acid sequence of SEQ ID NO: 5 consisting of 386 amino acids or the amino acid sequence of SEQ ID NO: 6 consisting of 387 amino acids. The mutant CREBBP of SEQ ID NO: 5 is a protein consisting of the amino acids of positions 1 to 374 of the mouse wild-type CREBBP of SEQ ID NO: 2 and additional 12 amino acids. The mutant CREBBP of SEQ ID NO: 6 is a protein consisting of the amino acids of positions 1 to 375 of the human wild-type CREBBP of SEQ ID NO: 4 and additional 12 amino acids. In an embodiment, the mutant CREBBP consists of an amino acid sequence having at least 90% identity with the amino acid sequence of SEQ ID NO: 5 or 6. In an embodiment, the mutant CREBBP comprises the amino acid sequence of SEQ ID NO: 5 or 6. In an embodiment, the mutant CREBBP consists of the amino acid sequence of SEQ ID NO: 5 or 6. The mutant CREBBP having any one of these amino acid sequences is substantially deficient in the transcriptional activation function of CREBBP.

The mutant CREBBP is encoded by a mutant CREBBP gene. The mutant CREBBP gene may have any mutation as long as it encodes the mutant CREBBP. In an embodiment, the mutant CREBBP gene comprises a nucleotide sequence having at least 90% identity with the nucleotide sequence of the mouse wild-type CREBBP gene of SEQ ID NO: 1 and lacking the nucleotide corresponding to position 1123 of SEQ ID NO: 1. In an embodiment, the mutant CREBBP gene comprises the nucleotide sequence of SEQ ID NO: 1 which lacks the nucleotide of position 1123 (SEQ ID NO: 7). In an embodiment, the mutant CREBBP gene consists of the nucleotide sequence of SEQ ID NO: 7. In an embodiment, the mutant CREBBP gene comprises a nucleotide sequence having at least 90% identity with the nucleotide sequence of the human wild-type CREBBP gene of SEQ ID NO: 3 and lacking the nucleotide corresponding to position 1126 of SEQ ID NO: 3. In an embodiment, the mutant CREBBP gene comprises the nucleotide sequence of SEQ ID NO: 3 which lacks the nucleotide of position 1126 (SEQ ID NO: 8). In an embodiment, the mutant CREBBP gene consists of the nucleotide sequence of SEQ ID NO: 8.

The term "nucleotide corresponding to position 1123 of SEQ ID NO: 1" means the nucleotide in a mutant CREBBP gene that matches the guanine nucleotide at position 1123 of SEQ ID NO: 1 when the nucleotide sequence of the mutant CREBBP gene and the nucleotide sequence of SEQ ID NO: 1 are optimally aligned. The term "optimally aligned" means two sequences are aligned so that the number of matched nucleotides is maximized. The term "nucleotide corresponding to position 1126 of SEQ ID NO: 3" is similarly defined.

In the disclosure the term "identity" of amino acid or nucleotide sequences means the degree of similarity in sequences of proteins or oligonucleotides. Identity is determined by comparing two sequences that are optimally aligned with each other over the regions to be compared. The term "optimally aligned" means two sequences are aligned so that the number of matched amino acids or nucleotides is maximized. The percentage (% of sequence identity is calculated by identifying amino acids or nucleotides matched in both sequences, determining the number of matched amino acids or nucleotides, dividing the number by the total number of the amino acids or nucleotides in the regions to be compared, and multiplying the derived value by 100. For making an optimal alignment and calculating sequence identity, any algorithm that is commonly available to those skilled in the art, e.g., BLAST algorithm or FASTA algorithm, may be used. Sequence identity may be determined using a software for sequence analysis such as BLAST or FASTA.

<Transgenic Animal>

The transgenic animal may be of any species other than human, typically a mammal, e.g., mouse, rat, hamster, rabbit, cat, dog, cow, sheep, or monkey. In an embodiment, the transgenic animal is a rodent, particularly a mouse.

The transgenic animal can be produced by introducing a mutation into at least one CREBBP locus of a non-human animal by a known gene modification technique for modifying a target gene. Examples of the known gene modification techniques include CRISPR system, methods using Transcription Activator-Like Effector Nucleases (TALEN), methods using zinc finger nucleases, and homologous recombination methods. Especially, the CRISPR system, which can modify a gene selectively and site-specifically, may be used. The CRISPR/Cas system is described in detail, for example in Wang, H. et al., Cell, 153, 910-918 (2013) and U.S. Pat. No. 8,697,359, the entire contents of which are incorporated herein by reference.

When the CRISPR system is used for producing the transgenic animal, Cas9 protein and guide RNA (gRNA) is introduced into a fertilized egg derived from a non-human animal. For the introduction, any known method may be used, including calcium phosphate transfection, electroporation, lipofection, aggregation method, microinjection, particle gun method, and DEAE-Dextran method.

The wild-type Cas9 protein has two functional nuclease domains, RuvC and HNH. Each domain cleaves different strand of a double-stranded DNA. The term "Cas9 protein" as used herein means a protein capable of binding to DNA in a gRNA dependent manner, which may have both RuvC and HNH nuclease activities or lack either or both nuclease activities. Cas9 protein may be derived from bacteria having a CRISPR system. Examples of the bacteria having a CRISPR system include *Streptococcus pyogenes, Neisseria meningitides, Streptococcus thermophiles*, and *Treponema denticola*. A nucleic acid encoding Cas9 protein or a vector comprising the nucleic acid may be used in place of Cas9 protein. Any Cas9 protein, nucleic acid encoding Cas9 protein, or vector comprising the nucleic acid known in the art may be used without limitation.

The term "guide RNA" or "gRNA" as used herein means a synthetic single-stranded RNA comprising a fusion of crRNA and tracrRNA. A linker sequence may be present between the crRNA and tracrRNA regions. Cas9 protein can bind to genomic DNA in the presence of gRNA in a target-specific manner. In place of gRNA, separate RNA molecules of crRNA and tracrRNA may be used in combination.

Sequence specificity of gRNA depends on crRNA, which is derived from an endogenous bacterial RNA. In the disclosure crRNA comprises the same nucleotide sequence as a target sequence present in genomic DNA. The target sequence is selected so that a PAM sequence is located immediately downstream of the target sequence in genomic DNA. The target sequence may be present in either strand of genomic DNA. Many tools for selecting the target sequence and/or designing gRNA and lists of candidate target sequences predicted by bioinformatics for various genes of various species are available. Examples include Feng Zhang lab's Target Finder, Michael Boutros lab's Target Finder (E-CRISP), RGEN Tools: Cas-OFFinder, CasFinder: Flexible algorithm for identifying specific Cas9 targets in genomes, and CRISPR Optimal Target Finder, the entire contents of which are incorporated herein by reference. In an embodiment, the target sequence is a nucleotide sequence having at least 90% identity with the nucleotide sequence of SEQ ID NO: 9. In an embodiment, the target sequence is a nucleotide sequence that is different from the nucleotide sequence of SEQ ID NO: 9 in that one to three nucleotides are added, deleted, and/or substituted in the nucleotide sequence of SEQ ID NO: 9. In an embodiment, the target sequence is the nucleotide sequence of SEQ ID NO: 9.

Cas9 protein can bind to a DNA sequence that has a PAM sequence immediately downstream of the target sequence. The PAM sequence is present immediately downstream of the target sequence in genomic DNA, whereas not present immediately downstream of the target sequence in gRNA. The PAM sequence varies depending on the bacterial species from which the Cas9 protein is derived. The most widely used Cas9 protein is derived from *Streptococcus pyogenes* and the corresponding PAM sequence is NGG present immediately downstream of the 3' end of the target sequence. Some combinations of bacterial species and the corresponding PAM sequence are known, for example, *Neisseria meningitides*: NNNNGATT, *Streptococcus thermophiles*: NNAGAA, *Treponema denticola*: NAAAAC, wherein N represents any one of A, T, G, and C.

On the other hand, tracrRNA hybridizes to a part of crRNA to form a hairpin structure. The structure is recognized by Cas9 protein and crRNA, tracrRNA, and Cas9 protein together form a complex. Thus tracrRNA is responsible for the ability of gRNA to bind to Cas9 protein. The sequence of tracrRNA is based on an endogenous bacterial RNA and varies depending on the bacterial species. In the disclosure tracrRNA may be derived from one of the bacterial species having a CRISPR system as listed above. Preferably, tracrRNA and Cas9 protein used for genome editing is derived from the same bacterial species.

To obtain gRNA, DNA encoding a desired gRNA sequence may be cloned into a vector suitable for in vitro transcription and transcribed in vitro. Suitable in vitro transcription vectors are known to those skilled in the art. In vitro transcription vectors that comprise a nucleotide sequence of gRNA having no target sequence are also known in the art. By synthesizing an oligonucleotide of a target sequence, inserting the oligonucleotide into such a vector, and performing in vitro transcription, gRNA may be obtained. Methods of in vitro transcription are known to those skilled in the art.

A gRNA/Cas9 protein complex is recruited to a target sequence in genomic DNA through complementary binding between the gRNA and the target sequence. Cas9 protein is localized to the target sequence through binding of the gRNA/Cas9 protein complex to the target sequence. Cas9 protein cleaves both strands of the genomic DNA, resulting in a double strand break (DSB). The DSB may be repaired through non-homologous end joining (NHEJ) DNA repair pathway or homology directed repair (HDR) pathway. The NHEJ repair pathway frequently leads to insertion/deletion of base(s) at the DSB site, which may cause a frameshift and/or a stop codon to disrupt the open reading frame of the targeted gene. The HDR pathway requires a repair template for repairing the DSB. Since the sequence of the repair template is precisely copied to the cleaved genomic DNA, a desired mutation can be introduced to the targeted gene by using the repair template and the HDR.

In order to modify a nucleotide in genomic DNA by the HDR, a DNA repair template containing a desired sequence has to be present during the HDR. In an embodiment, the DNA repair template is a single-stranded oligodeoxynucleotide (ssODN). The ssODN has high homology to the sequences upstream and downstream of the DSB. The length and position of each homology region depends on the size of the modification to be introduced. In the presence of a suitable template, the HDR can modify a desired nucleotide at the site of the DSB made by Cas9 protein. The ssODN is designed so that the modified gene is not cleaved by Cas9 protein. This means that the ssODN is designed so that it does not contain the PAM sequence immediately downstream of the target sequence, for example, by replacing the PAM sequence in the ssODN with a different sequence. Details for designing an ssODN are described in, for example, Yang, H. et al., Cell, 154(6), 1370-9 (2013), the entire contents of which are incorporated herein by reference. In general, ssODN is introduced into a cell together with gRNA and Cas9 protein.

The transgenic animal may be obtained by implanting an fertilized egg to which Cas9 protein and gRNA were introduced to the uterus or fallopian tube of a corresponding non-human animal and allowing the development. Whether the transgenic animal has been successfully obtained may be confirmed by various methods known in the art, for example, by observing the phenotype or sequencing the genomic DNA comprising the target sequence. In the case of HDR, a restriction enzyme site may be incorporated to ssODN and the restriction fragment length polymorphism (RFLP) may be detected. These methods are well known in the art.

The transgenic animal may be heterozygous, i.e., either allele in the genome is modified, or homozygous, i.e., both alleles in the genome are modified. The transgenic animal is preferably heterozygous. A homozygous transgenic animal may be generated by mating heterozygous transgenic animals.

As shown in the Examples below, the disclosed transgenic animal exhibits at least one symptom of Rubinstein-Taybi syndrome. Examples of the symptoms include psychomotor retardation, small body size, low body weight, short body length, hypertelorism, short dorsal nasal, cryptorchidism, micropenis, low blood pressure, and low body temperature. Accordingly, the disclosed transgenic animal may be used as a model animal of Rubinstein-Taybi syndrome. Furthermore, the disclosed transgenic animal has a tendency of advanced circadian rhythm, thus may be used as a model animal of Rubinstein-Taybi syndrome associated with advanced sleep phase syndrome or a model animal of advanced sleep phase syndrome. Such model animals are useful for elucidating causes of the diseases or developing methods of prevention and treatment.

<Method of Screening for Medicament>

For example, the disclosed transgenic animal may be used as a model animal of Rubinstein-Taybi syndrome or advanced sleep phase syndrome or screening for a medicament.

Accordingly, an aspect of the disclosure provides a method of screening for a medicament for treating Rubinstein-Taybi syndrome comprising:
 (a) administering at least a candidate substance to the disclosed transgenic animal; and
 (b) selecting the candidate substance as a medicament for treating Rubinstein-Taybi syndrome when a symptom of Rubinstein-Taybi syndrome is more ameliorated in the transgenic animal to which the candidate substance was administered than in the transgenic animal to which the candidate substance was not administered.

Another aspect of the disclosure provides a method of screening for a medicament for treating advanced sleep phase syndrome comprising:
 (a) administering at least a candidate substance to the disclosed transgenic animal; and
 (b) selecting the candidate substance as a medicament for treating advanced sleep phase syndrome when a symptom of advanced sleep phase syndrome is more ameliorated in the transgenic animal to which the candidate substance was administered than in the transgenic animal to which the candidate substance was not administered.

The term "treatment" of a disease as used herein means that the disease onset is prevented, possibility of the disease onset is decreased, a cause of the disease is reduced or removed, progression of the disease is delayed or stopped, and/or a symptom of the disease is reduced, alleviated, ameliorated, or removed.

The term "candidate substance" includes any substance, for example, proteins, amino acids, nucleic acids, lipids, carbohydrates, and small molecules. The candidate substance is typically a purified or isolated substance, but may be provided in an unpurified or unisolated crude material. The candidate substance may be provided in a library, such as compound libraries, nucleic acid libraries, or random peptide libraries, or may be provided in a natural material. The introduction of the candidate substance into a cell may be performed by a known method, depending on the type of the candidate substance. A single candidate substance or a combination of two or more candidate substances may be administered.

The dosage and the number of doses of the candidate substance may be appropriately adjusted in view of factors such as the age, sex, body weight, and symptom of the transgenic animal, as well as the employed administration route. Administration routes of the candidate substance include oral and parenteral routes and are not particularly limited. For example, the parenteral administration may be systemic or local administration, more specifically, intratracheal, intraspinal, intrathecal, intracranial, intravenous, intraarterial, intraportal, intradermal, subcutaneous, transcutaneous, intramuscular, intraperitoneal, intranasal, or intraoral administration. The transgenic animal may be a fetus or a postnatal animal. When the transgenic animal is a fetus, the candidate substance may be administered to the fetus or mother.

For screening for a medicament for treating Rubinstein-Taybi syndrome, amelioration of a symptom of Rubinstein-Taybi syndrome may be determined by observing a symptom such as small body size, low body weight, short body length, hypertelorism, short dorsal nasal, low blood pressure, or low body temperature. For example, a candidate substance may be selected as the medicament when a value related to a symptom in the transgenic animal to which the candidate substance was administered is, e.g., at least about 10%, preferably at least about 20%, more preferably at least about 30%, even more preferably at least about 50%, higher than the value in the transgenic animal to which the candidate substance was not administered.

For screening for a medicament for treating advanced sleep phase syndrome, amelioration of a symptom of advanced sleep phase syndrome may be determined by observing the circadian rhythm. For example, a candidate substance may be selected as the medicament when activity cycle under constant dark condition in the transgenic animal to which the candidate substance was administered is ameliorated by, e.g., at least about 10%, preferably at least about 20%, more preferably at least about 30%, even more preferably at least about 50%, higher than in the transgenic animal to which the candidate substance was not administered.

<Marker for Determination>

Another aspect of the disclosure provides a peptide consisting of an amino acid sequence having at least 90% identity with the amino acid sequence of SEQ ID NO: 5 or 6. The peptide may be used as a marker for determining Rubinstein-Taybi syndrome or advanced sleep phase syndrome. Another aspect of the disclosure provides a polynucleotide encoding a peptide consisting of an amino acid sequence having at least 90% identity with the amino acid sequence of SEQ ID NO: 5 or 6. The polynucleotide may be used as a marker for determining Rubinstein-Taybi syndrome or advanced sleep phase syndrome.

When the CREBBP gene has a mutation and encodes a peptide consisting of an amino acid sequence having at least 90% identity with the amino acid sequence of SEQ ID NO: 5 or 6, for example, the CREBBP gene lacks a nucleotide corresponding to position 1123 of SEQ ID NO: 1 or position 1126 of SEQ ID NO: 3, the CREBBP gene may cause Rubinstein-Taybi syndrome or advanced sleep phase syndrome. Accordingly, Rubinstein-Taybi syndrome or advanced sleep phase syndrome may be determined by determining the presence or absence of the mutation in the CREBBP or CREBBP gene. The peptide or polypeptide comprising the mutation is useful as a marker for determining Rubinstein-Taybi syndrome or advanced sleep phase syndrome. Examples of the polynucleotides include DNAs, cDNAs, RNAs, mRNAs, DNA analogues, and RNA analogues.

<Method of Determination>

Another aspect of the disclosure provides a method of determining Rubinstein-Taybi syndrome or advanced sleep phase syndrome by using the marker described above. The diseases may be determined by determining the presence or absence of the mutation described above in a sample obtained from a subject. The term "determining a disease" as used herein means determining whether a subject is suffering from the disease or whether a subject has a possibility to suffer from the disease.

The subject may be of any species, typically a mammal, e.g., human, mouse, rat, hamster, rabbit, cat, dog, cow, sheep, or monkey. In an embodiment, the subject is a rodent, particularly a mouse. In an embodiment, the subject is a primate, particularly a human. The subject may be a fetus.

The sample may be obtained from the subject by any conventional method. The sample may be taken from body fluid such as blood, spinal fluid, or saliva, or a tissue such as oral mucosa or hair. When the subject is a fetus, the sample may be collected by amniocentesis or chorionic villus sampling.

When the marker is a peptide, the presence or absence of the mutation in a sample obtained from the subject is determined by using an agent that recognizes the peptide such as an antibody. Methods for detecting a mutation are well known to those skilled in the art and are not limited. It is preferred to use an agent that specifically recognizes the mutant peptide. When an agent that recognizes both of the wild-type and mutant peptides is used, the mutation may be detected on the basis of the difference in the molecular weights of the peptides.

When the marker is a polynucleotide, nucleic acids may be isolated from a sample obtained from the subject. Methods for isolating nucleic acids are well known to those skilled in the art and are not limited. For example, a commercially available kit for collecting DNAs or RNAs may be used. The nucleic acids as used herein are DNAs or RNAs, including fragments obtained by amplifying the target region, e.g., the full-length CREBBP gene or a part thereof, by polymerase chain reaction (PCR) or other methods using DNAs or RNAs as a template.

The presence or absence of the mutation in the nucleic acids is then determined. Methods for detecting a mutation are well known to those skilled in the art and are not limited. Typical methods comprise determining the nucleotide sequence of the CREBBP gene, determining the amino acid sequence encoded by the nucleotide sequence, and determining whether the amino acid sequence has at least 90% identity with the amino acid sequence of SEQ ID NO: 5 or 6.

Alternatively, a deletion of the nucleotide corresponding to position 1123 of SEQ ID NO: 1 or position 1126 of SEQ ID NO: 3 in the CREBBP gene may be detected. Examples of the detection methods include PCR, allele-specific PCR, PCR-SSP, PCR-RFLP, PCR-SSCP, direct sequencing, ASO hybridization, DGGE, RNaseA cleavage method, chemical cleavage method, DOL, Invader assay, TaqMan (registered trade mark)-PCR, MALDI-TOF/MS, TDI, molecular beacon technology, dynamic allele-specific hybridization, and Padlock Probe technology.

When the sample obtained from the subject has the mutation described above, the subject is determined to be suffering or will suffer from Rubinstein-Taybi syndrome or advanced sleep phase syndrome. Alternatively, when the sample obtained from the subject has the mutation described above, the possibility that the subject is suffering or will suffer from Rubinstein-Taybi syndrome or advanced sleep phase syndrome is determined to be high.

<Kit for Determination>

Another aspect of the disclosure provides a kit for determining Rubinstein-Taybi syndrome or advanced sleep phase syndrome. The kit comprises a means for determining whether the CREBBP gene has a mutation that produces a peptide consisting of an amino acid sequence having at least 90% identity with the amino acid sequence of SEQ ID NO: 5 or 6, for example, a deletion of the nucleotide corresponding to position 1123 of SEQ ID NO: 1 or position 1126 of SEQ ID NO: 3.

The means for determining the presence or absence of the mutation in the CREBBP gene is not limited. For example, the means may be a means used for detecting the mutation in the determination method described above, e.g., primers that can amplify a region containing the mutation or probes that can bind to such a region. In an embodiment, the means for determining the presence or absence of the mutation is a primer for allele-specific PCR, e.g., the primers having the nucleotide sequence of SEQ ID NOs: 13 and 14 when the subject is a mouse. The kit may also comprise other components as needed. The other components may include, for example, but are not limited to, a tool for collecting a sample, e.g., a syringe, a positive control sample, and a negative control sample. The kit may comprise something to show the procedures for performing the method described above, such as a written description.

For example, the disclosure provides the following embodiments.

[1] A non-human transgenic animal having at least one CREBBP gene locus into which a mutation has been introduced, wherein the mutated CREBBP gene encodes a mutant CREBBP consisting of an amino acid sequence having at least 90% identity with the amino acid sequence of SEQ ID NO: 5.

[2] The transgenic animal according to item 1, wherein the mutant CREBBP comprises the amino acid sequence of SEQ ID NO: 5.

[3] The transgenic animal according to item 1 or 2, wherein the mutant CREBBP comprises the amino acid sequence of SEQ ID NO: 5.

[4] The transgenic animal according to any one of items 1 to 3, wherein the mutant CREBBP is substantially deficient in a transcriptional activation function.

[5] The transgenic animal according to any one of items 1 to 4, wherein the CREBBP gene comprises a nucleotide sequence that has at least 90% identity with the nucleotide sequence of SEQ ID NO: 1 and lacks a nucleotide corresponding to position 1123 of SEQ ID NO: 1.

[6] The transgenic animal according to any one of items 1 to 5, wherein the CREBBP gene comprises the nucleotide sequence of SEQ ID NO: 7.

[7] The transgenic animal according to any one of items 1 to 6, wherein the CREBBP gene consists of the nucleotide sequence of SEQ ID NO: 7.
[8] The transgenic animal according to any one of items 1 to 7, wherein the transgenic animal is a rodent.
[9] The transgenic animal according to any one of items 1 to 8, wherein the transgenic animal is a mouse.
[10] The transgenic animal according to any one of items 1 to 9, wherein the transgenic animal is a model of Rubinstein-Taybi syndrome.
[11] The transgenic animal according to item 10, wherein the Rubinstein-Taybi syndrome is associated with advanced sleep phase syndrome.
[12] The transgenic animal according to any one of items 1 to 9, wherein the transgenic animal is a model of advanced sleep phase syndrome.
[13] A method of producing the transgenic animal according to any one of items 1 to 12, comprising introducing a mutation into at least one CREBBP gene locus of a non-human animal.
[14] The method according to item 13, wherein the mutation is introduced by genome editing.
[15] The method according to item 14, wherein the target sequence of the genome editing is a nucleotide sequence having at least 90% identity with the nucleotide sequence of SEQ ID NO: 9.
[16] The method according to item 14, wherein the target sequence of the genome editing is a nucleotide sequence that is different from the nucleotide sequence of SEQ ID NO: 9 in that one to three nucleotides are added, deleted, and/or substituted in the nucleotide sequence of SEQ ID NO: 9.
[17] The method according to item 15 or 16, wherein the target sequence is the nucleotide sequence of SEQ ID NO: 9.
[18] The method according to any one of items 14 to 17, wherein an ssODN capable of producing the desired mutation is further used.
[19] A transgenic animal produced by the method according to any one of items 13 to 18.
[20] Use of the transgenic animal according to any one of items 1 to 12 and 19 as a model of Rubinstein-Taybi syndrome.
[21] The use according to item 20, wherein the Rubinstein-Taybi syndrome is associated with advanced sleep phase syndrome.
[22] Use of the transgenic animal according to any one of items 1 to 12 and 19 as a model of advanced sleep phase syndrome.
[23] A peptide consisting of an amino acid sequence having at least 90% identity with the amino acid sequence of SEQ ID NO: 5 or 6.
[24] The peptide according to item 23, comprising the amino acid sequence of SEQ ID NO: 5 or 6.
[25] The peptide according to item 23 or 24, consisting of the amino acid sequence of SEQ ID NO: 5 or 6.
[26] A polynucleotide encoding the peptide according to any one of items 23 to 25.
[27] The polynucleotide according to item 26, comprising a nucleotide sequence that has at least 90% identity with the nucleotide sequence of SEQ ID NO: 1 and lacks a nucleotide corresponding to position 1123 of SEQ ID NO: 1, or a nucleotide sequence that has at least 90% identity with the nucleotide sequence of SEQ ID NO: 3 and lacks a nucleotide corresponding to position 1126 of SEQ ID NO: 3.
[28] The polynucleotide according to item 26 or 27, comprising the nucleotide sequence of SEQ ID NO: 7 or B.
[29] The polynucleotide according to any one of items 26 to 28, consisting of the nucleotide sequence of SEQ ID NO: 7 or 8.
[30] Use of the peptide according to any one of items 23 to 25 as a marker for determining Rubinstein-Taybi syndrome.
[31] Use of the polynucleotide according to any one of items 26 to 29 as a marker for determining Rubinstein-Taybi syndrome.
[32] A method of determining Rubinstein-Taybi syndrome, comprising:
  (1) testing whether a sample obtained from a subject comprises the marker according to item 30 or 31; and
  (2) determining that the subject is suffering or will suffer from Rubinstein-Taybi syndrome when the sample is determined to comprise the marker.
[33] Use of the peptide according to any one of items 23 to 25 as a marker for determining advanced sleep phase syndrome.
[34] Use of the polynucleotide according to any one of items 26 to 29 as a marker for determining advanced sleep phase syndrome.
[35] A method of determining advanced sleep phase syndrome, comprising:
  (1) testing whether a sample obtained from a subject comprises the marker according to item 33 or 34; and
  (2) determining that the subject is suffering or will suffer from advanced sleep phase syndrome when the sample is determined to comprise the marker.
[36] A method of determining Rubinstein-Taybi syndrome, comprising:
  (1) determining a nucleotide sequence of the CREBBP gene in a nucleic acid sample obtained from a subject;
  (2) determining the amino acid sequence encoded by the nucleotide sequence; and
  (3) determining that the subject is suffering or will suffer from Rubinstein-Taybi syndrome when the amino acid sequence has at least 90% identity with the amino acid sequence of SEQ ID NO: 5 or 6.
[37] A method of determining Rubinstein-Taybi syndrome, comprising:
  (1) determining whether the CREBBP gene in a nucleic acid sample obtained from a subject lacks a nucleotide corresponding to position 1123 of SEQ ID NO: 1 or position 1126 of SEQ ID NO: 3; and
  (2) determining that the subject is suffering or will suffer from Rubinstein-Taybi syndrome when the CREBBP gene lacks the nucleotide.
[38] A method of determining advanced sleep phase syndrome, comprising:
  (1) determining a nucleotide sequence of the CREBBP gene in a nucleic acid sample obtained from a subject;
  (2) determining the amino acid sequence encoded by the nucleotide sequence; and
  (3) determining that the subject is suffering or will suffer from advanced sleep phase syndrome when the amino acid sequence has at least 90% identity with the amino acid sequence of SEQ ID NO: 5 or 6.
[39] A method of determining advanced sleep phase syndrome, comprising:
  (1) determining whether the CREBBP gene in a nucleic acid sample obtained from a subject lacks a nucleotide corresponding to position 1123 of SEQ ID NO: 1 or position 1126 of SEQ ID NO: 3; and (2) determining that the subject is suffering or will suffer from advanced sleep phase syndrome when the CRE-BBP gene lacks the nucleotide.

[40] The method according to any one of items 32 and 35 to 39, wherein the subject is a fetus.

[41] A kit for determining Rubinstein-Taybi syndrome, comprising a means for determining whether the CRE-BBP gene has a mutation that produces a peptide consisting of an amino acid sequence having at least 90% identity with the amino acid sequence of SEQ ID NO: 5 or 6.

[42] A kit for determining advanced sleep phase syndrome, comprising a means for determining whether the CRE-BBP gene has a mutation that produces a peptide consisting of an amino acid sequence having at least 90% identity with the amino acid sequence of SEQ ID NO: 5 or 6.

[43] The kit according to item 41 or 42, wherein the means is a primer for allele-specific PCR.

[44] The kit according to item 43, wherein the means is primers consisting of the nucleotide sequences of SEQ ID NOs: 13 and 14.

The entire contents of the documents cited herein are incorporated herein by reference.

The embodiments described above are non-limiting and may be modified without deviating from the scope of the invention as defined by the appended claims. The following non-limitative examples are provided for illustrative purposes only.

EXAMPLES

Test 1: Analysis of Spontaneously Generated Dwarf Mouse (1) Emergence and Maintenance of Dwarf Mouse During keeping the strain of ghrelin-deficient (ghrl$^{+/-}$) mice described in Sato T, Kurokawa M, Nakashima Y, Ida T, Takahashi T, Fukue Y, Ikawa M, Okabe M, Kangawa K, Kojima M. Regul Pept. 2008 Jan. 10; 145(1-3):7-11, a mouse having characteristic appearances, e.g., small body size, specific facial characteristics, and low walking posture, emerged spontaneously (hereinafter referred to as "dwarf mouse"). The first generation was obtained by crossing the dwarf mouse (male) with a C57BL/6J mouse (female). Backcrossing (10 generations) was performed by crossing a dwarf mouse (male) with a C57BL/6J mouse (female) for nine generations and crossing a dwarf mouse (female) with a C57BL/6J mouse (male) for one generation. As a result, the characteristic appearances of the dwarf mouse were maintained, suggesting the dwarf phenotype emerged due to a genetic mutation.

(2) Emergence Ratio of Dwarf Mice

The emergence ratio of normal mice to dwarf mice was 277:138 in crossing dwarf mice (male) with C57BL/6J mice (female). Crossing dwarf mice with C57BL/6J mice produced dwarf mice regardless of the sex of the parent dwarf mice, and crossing dwarf mice with C57BL/6J mice produced both normal and dwarf mice. The results suggest the dwarf trait is inherited by autosomal dominant inheritance. The reason why the birth ratio is different from the ratio of the Mendelian autosomal dominant inheritance may be dwarf offspring were killed by cannibalism or the homozygous mutants are embryonic lethal.

(3) Appearances of Dwarf Mice

FIG. 1 shows a representative appearance of the dwarf mice. The dwarf mice were characterized by smaller body size, longer intercanthal distance, and shorter nasal dorsal compared to normal mice of the same sex.

(4) Body Measurement

Figure 2:
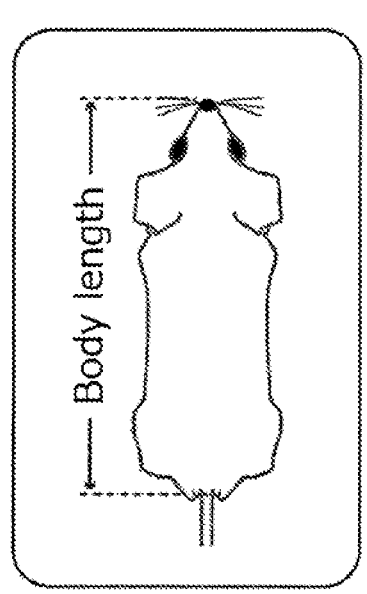
FIG. 2 shows the body length, body weight, and BMI of the normal and dwarf mice.
Figure 2:
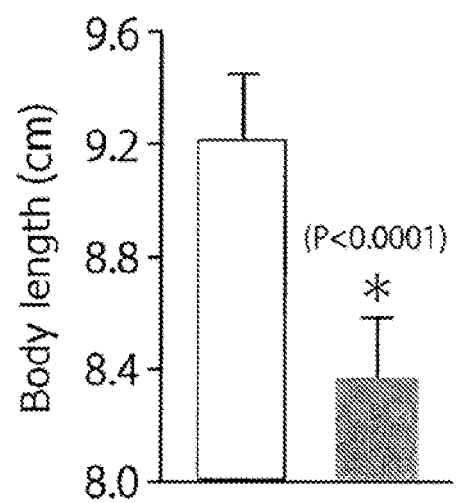
Figure 2:
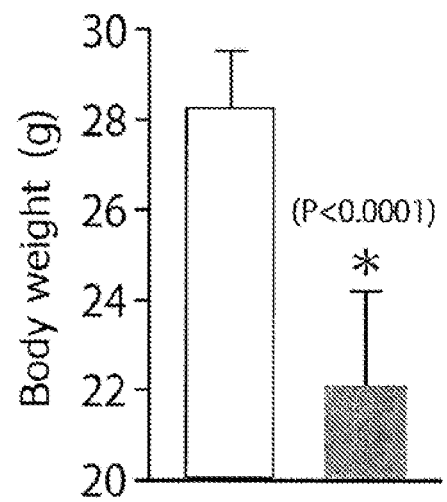
Figure 2:
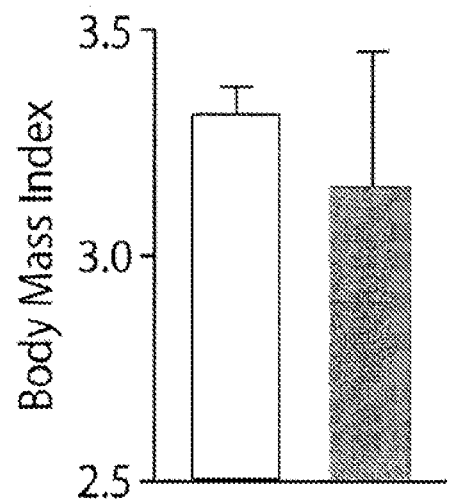

Male mice were used in the following studies unless otherwise indicated. The body length and body weight were measured and the BMI was calculated for the normal and dwarf mice. The results are shown in FIG. 2. The dwarf mice had shorter body length and lighter body weight than the normal mice, but no significant difference was found in the BMI.

Figure 3:
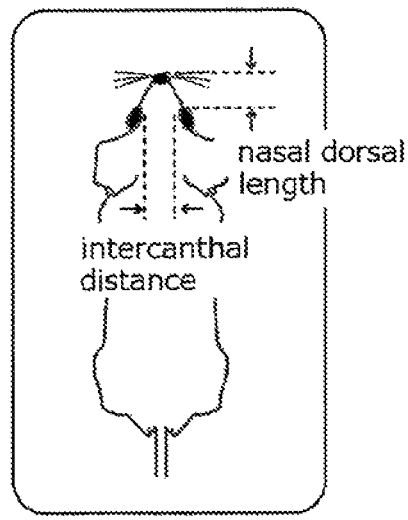
FIG. 3 shows the nasal dorsal length and intercanthal distance of the normal and dwarf mice.
Figure 3:
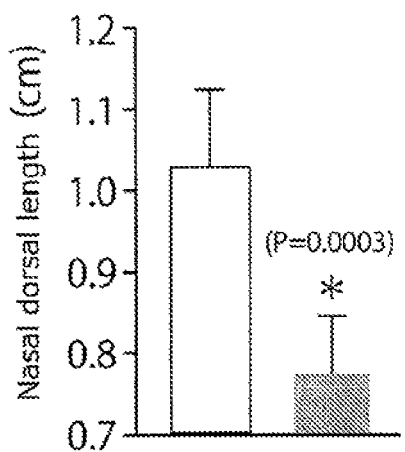
Figure 3:
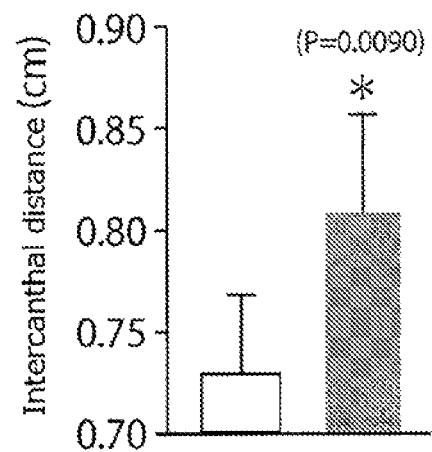

The nasal dorsal length and intercanthal distance of the normal and dwarf mice were measured. The results are shown in FIG. 3. The dwarf mice had significantly shorter nasal dorsal and significantly longer intercanthal distance than the normal mice.

(5) Blood Pressure and Body Temperature Under Standard Conditions

Figure 4:
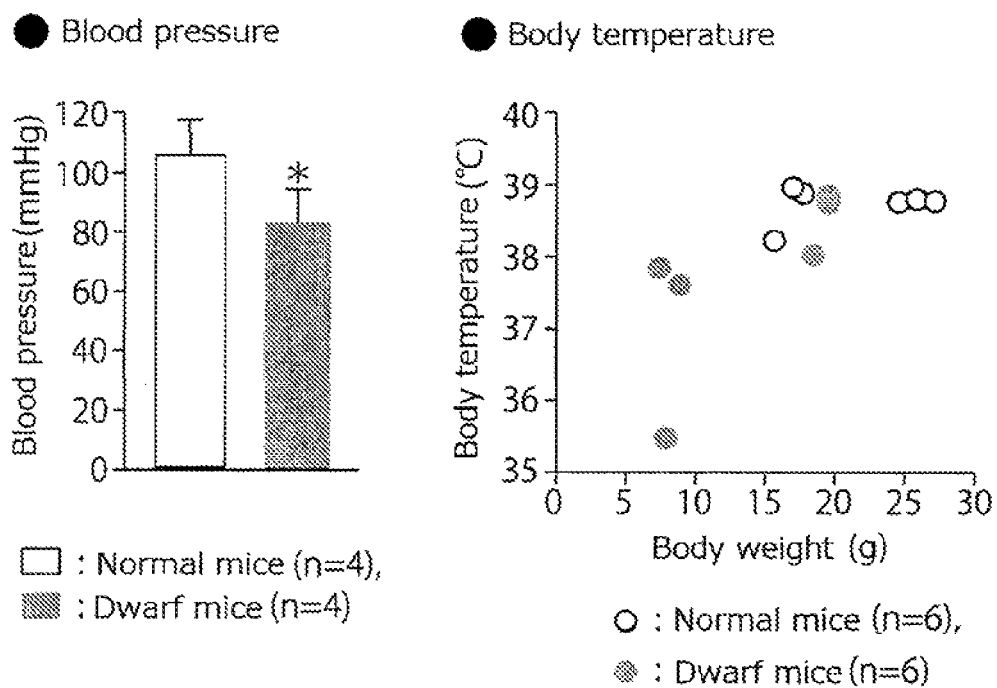
FIG. 4 shows the blood pressure and body temperature of the normal and dwarf mice.

The blood pressure and body temperature of the normal and dwarf mice were measured. The results are shown in FIG. 4. The dwarf mice had a tendency of low blood pressure and low body temperature. The body temperature of the dwarf mice had a tendency to correlate with the body weight.

(6) Blood Biochemical Analysis

Blood samples of the normal and dwarf mice were measured by VetScan (CENTRAL SCIENTIFIC COMMERCE, INC.). The results are shown in the table below. The dwarf mice had higher levels of alkaline phosphatase, calcium, and inorganic phosphate, and lower glucose levels.

TABLE 1

|  | Normal mice (n = 8) | Dwarf mice (n = 8) |  |
| --- | --- | --- | --- |
| Albumin (g/dL) | 3.8 ± 0.2 | 3.8 ± 0.2 |  |
| Alkaline phosphatase (IU/L) | 80.9 ± 12.6 | 96.8 ± 9.0 | p = 0.0116 |
| Alanine aminotransferase (IU/L) | 45.3 ± 8.5 | 49.3 ± 8.4 |  |
| Amylase (IU/L) | 939.0 ± 83.7 | 902.5 ± 106.9 |  |
| Bilirubin (mg/dl) | 0.3 ± 0.0 | 0.4 ± 0,1 |  |
| Urea nitrogen (mg/dL) | 24.1 ± 1.4 | 26.1 ± 3.9 |  |
| Calcium (mg/dL) | 9.4 ± 0.2 | 9.8 ± 0.3 | p = 0.0138 |
| Inorganic phosphorus (mg/dL) | 6.9 ± 0.5 | 8.7 ± 1.0 | p = 0.0006 |
| Creatinine (mg/dL) | (Below detection limit) | (Below detection limit) |  |
| Glucose (mg/dL) | 158.1 ± 9.2 | 122.9 ± 12.7 | p < 0.0001 |
| Sodium (mmol/L) | 151.9 ± 1.1 | 150.6 ± 2.8 |  |
| Potassium (mmol/L) | (Above detection limit) | (Above detection limit) |  |
| Total protein (g/dL) | 5.6 ± 0.1 | 5.6 ± 0.3 |  |
| Globulin (g/dL) | 1.8 ± 0.2 | 1.8 ± 0.2 |  |

(7) Time Course of Body Weight

Figure 5:
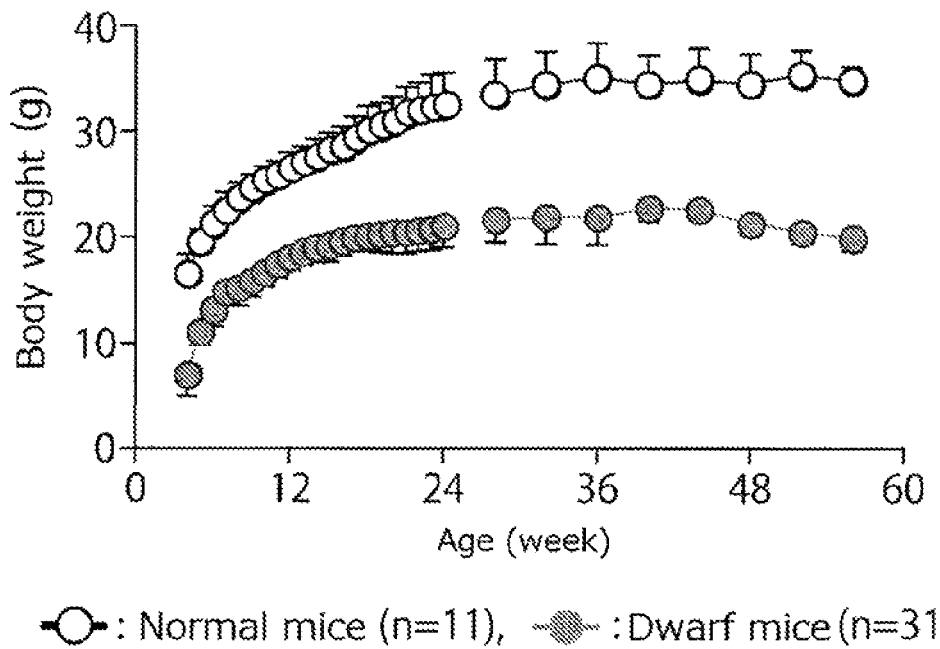
FIG. 5 shows the time course of the body weight of the normal and dwarf mice.

Time course of the body weight was observed for the normal and dwarf mice. The results are shown in FIG. 5. Growth curve of the dwarf mice was similar to that of the normal mice.

(8) Food Intake Under Standard Conditions

Figure 6:
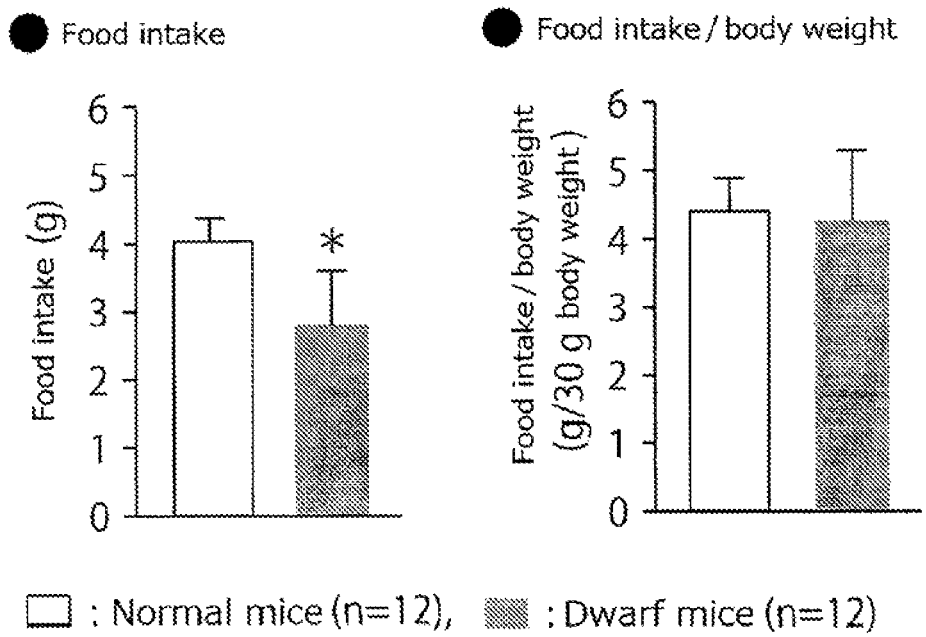
FIG. 6 shows the food intake and the food intake relative to the body weight of the normal and dwarf mice under standard conditions.

Food intake for 24 hours was measured for the normal and dwarf mice under standard conditions. The results are shown in FIG. 6. Although the food intake was less in the dwarf mice than in the normal mice, no difference was found in the food intake relative to the body weight.

(9) Body Weight and Food Intake after Fasting

Figure 7:
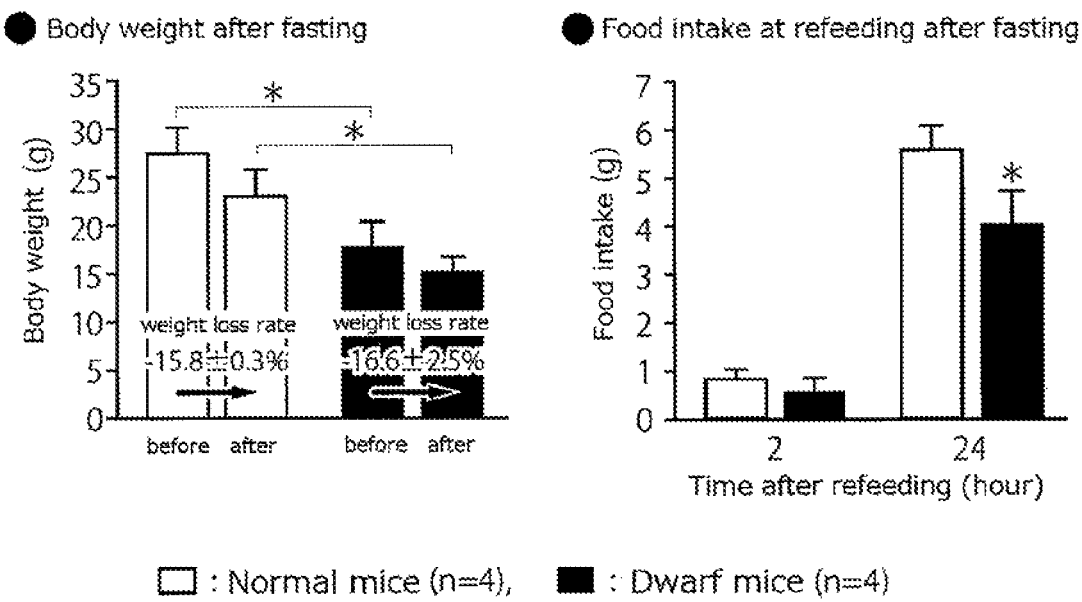
FIG. 7 shows the body weight and food intake of the normal and dwarf mice after fasting.

The normal and dwarf mice were fasted for 24 hours. The body weight after fasting and the food intake at refeeding after fasting were weighed. The results are shown in FIG. 7. No difference was found in the rate of weight loss between the dwarf and normal mice after 24 hours of fasting.

(10) GH and IGF-I Levels Under Standard Conditions

Figure 8:
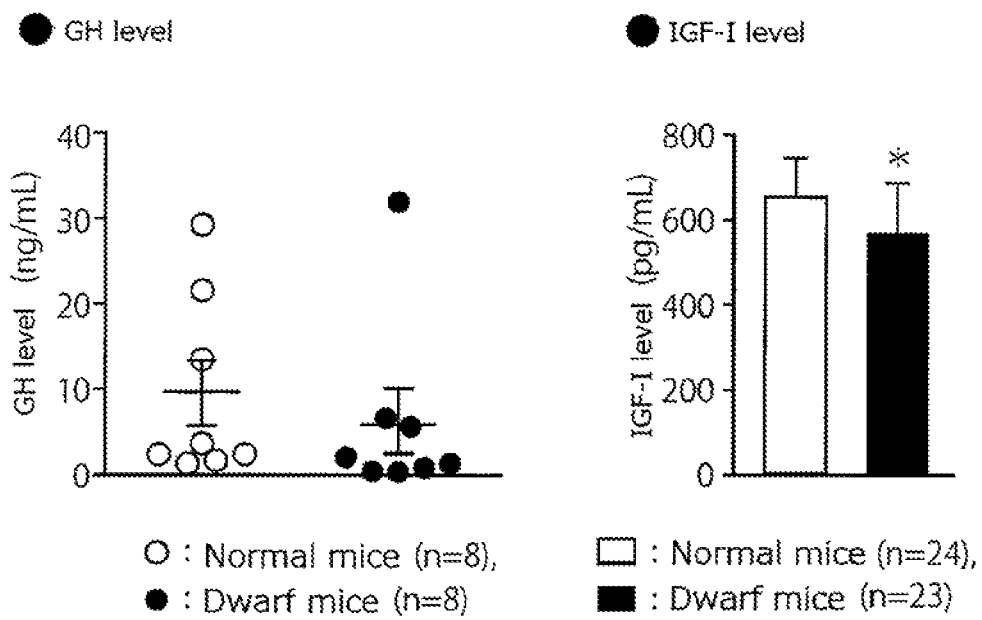
FIG. 8 shows the blood levels of growth hormone and insulin-like growth factor-I in the normal and dwarf mice.

The blood levels of growth hormone (GH) and insulin-like growth factor-I (IGF-I) in the normal and dwarf mice were measured. The results are shown in FIG. 8. No difference was found in the GH level between the dwarf mice and normal mice. The IGF-I level was significantly lower in the dwarf mice than in the normal mice.

(11) Time Course of Blood Glucose Level in Glucose Tolerance Test

Figure 9:
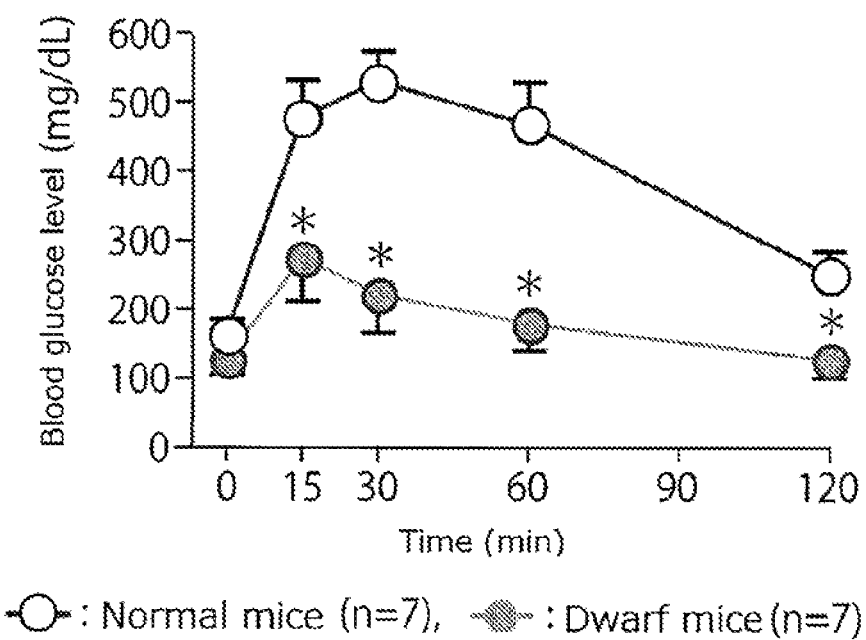
FIG. 9 shows the time course of the blood glucose level in the normal and dwarf mice in the glucose tolerance test.

The normal and dwarf mice were fasted for 2 hours and glucose (2 g/kg) was intraperitoneally administered. The results are shown in FIG. 9. The dwarf mice had significantly better glucose tolerance than the normal mice.

(12) Time Course of Insulin Level in Glucose Tolerance Test

Figure 10:
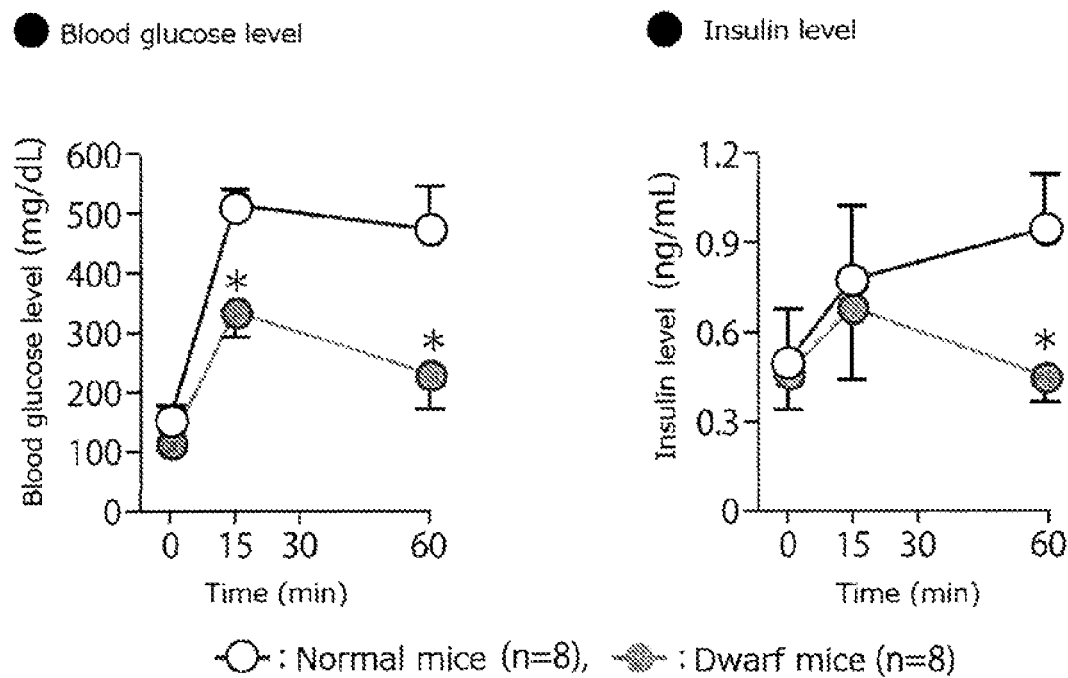
FIG. 10 shows the time courses of the blood glucose level and insulin level in the normal and dwarf mice in the glucose tolerance test.

The normal and dwarf mice were fasted for 2 hours and glucose (2 g/kg) was intraperitoneally administered. The results are shown in FIG. 10. The insulin level decreased earlier in the dwarf mice than in the normal mice.

(13) Activity Rhythm

Figure 11:
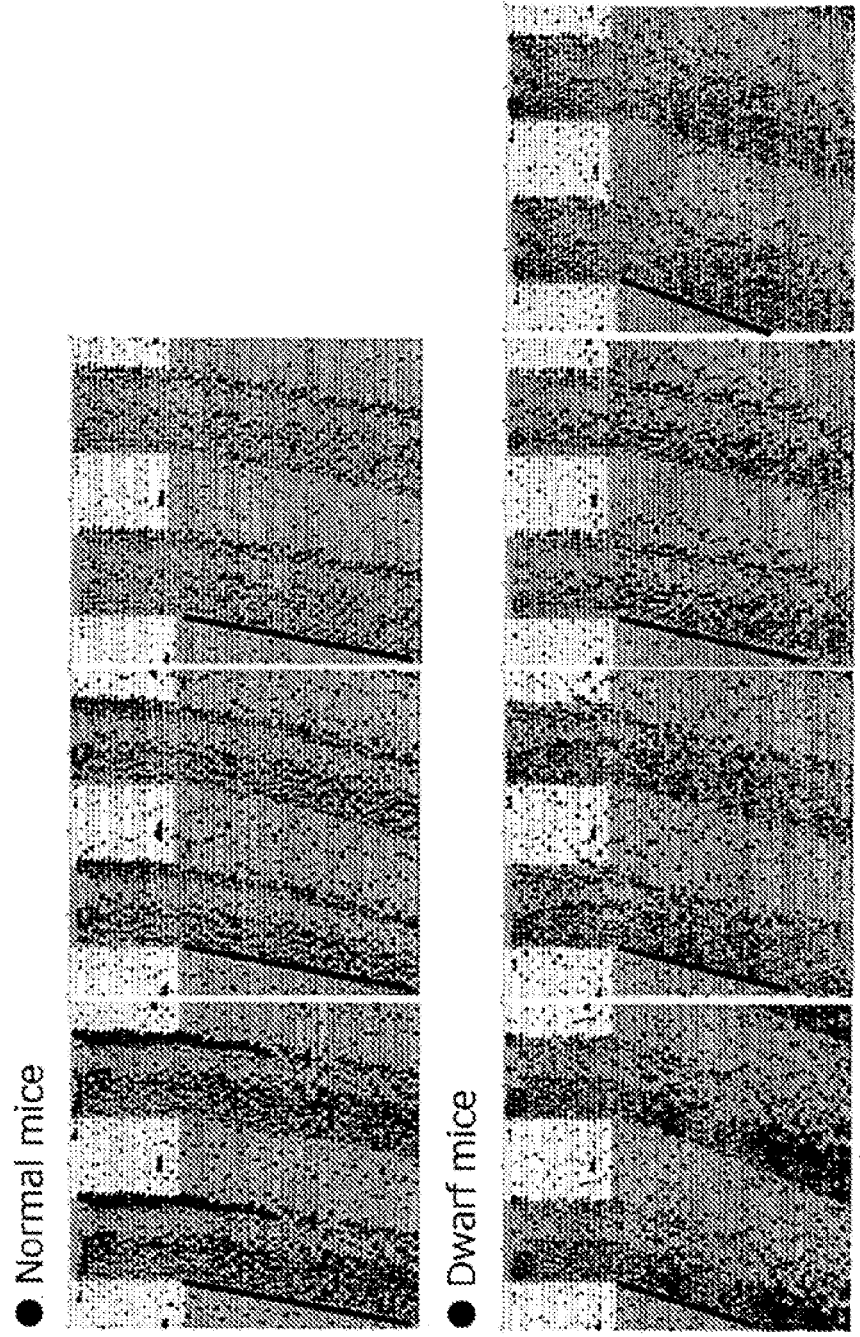
FIG. 11 shows the actograms showing the activity rhythms of the normal and dwarf mice under the light/dark and constant darkness conditions.

Three normal and four dwarf mice were placed under light/dark and constant darkness conditions and the activity records were double plotted. The actograms of the mice are individually shown in FIG. 11. Under the light/dark conditions (top of each panel), the activity cycle of the dwarf mice was similar to that of the normal mice. Under the constant darkness conditions (bottom of each panel) the slope of the line drawn along the activity onsets was smaller in the dwarf mice, suggesting that the activity cycle of the dwarf mice is shorter than that of the normal mice. Because activity cycles under constant darkness conditions reflect endogenous circadian rhythms, the results indicate that the dwarf mice can be used as a model of advanced sleep phase syndrome.

(14) Footprint Test (Gait Analysis)

Figure 12:
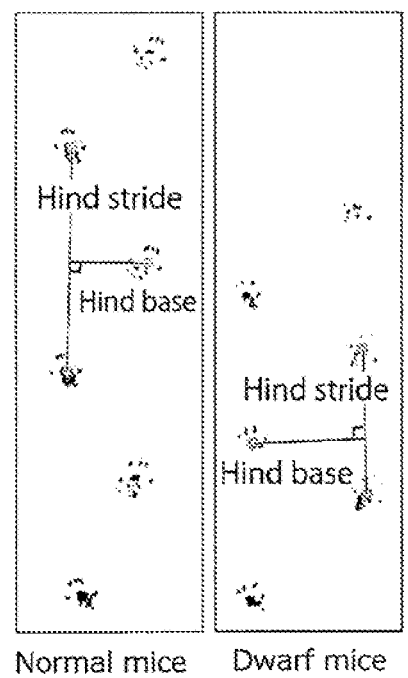
FIG. 12 shows the results of the footprint test for the normal and dwarf mice.
Figure 12:
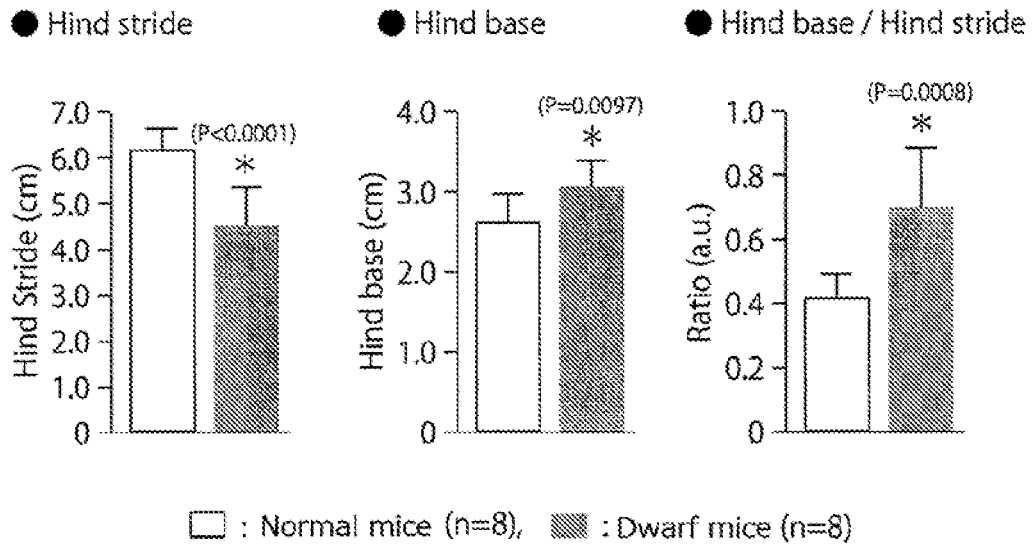

The hind paws of the normal and dwarf mice were painted with ink and the mice were allowed to walk on papers. The hind stride and hind base of the footprints were measured. The results are shown in FIG. 12. The hind base was wider and the hind stride was narrower in the dwarf mice than in the normal mice.

(15) Grip Strength Measurement

Figure 13:
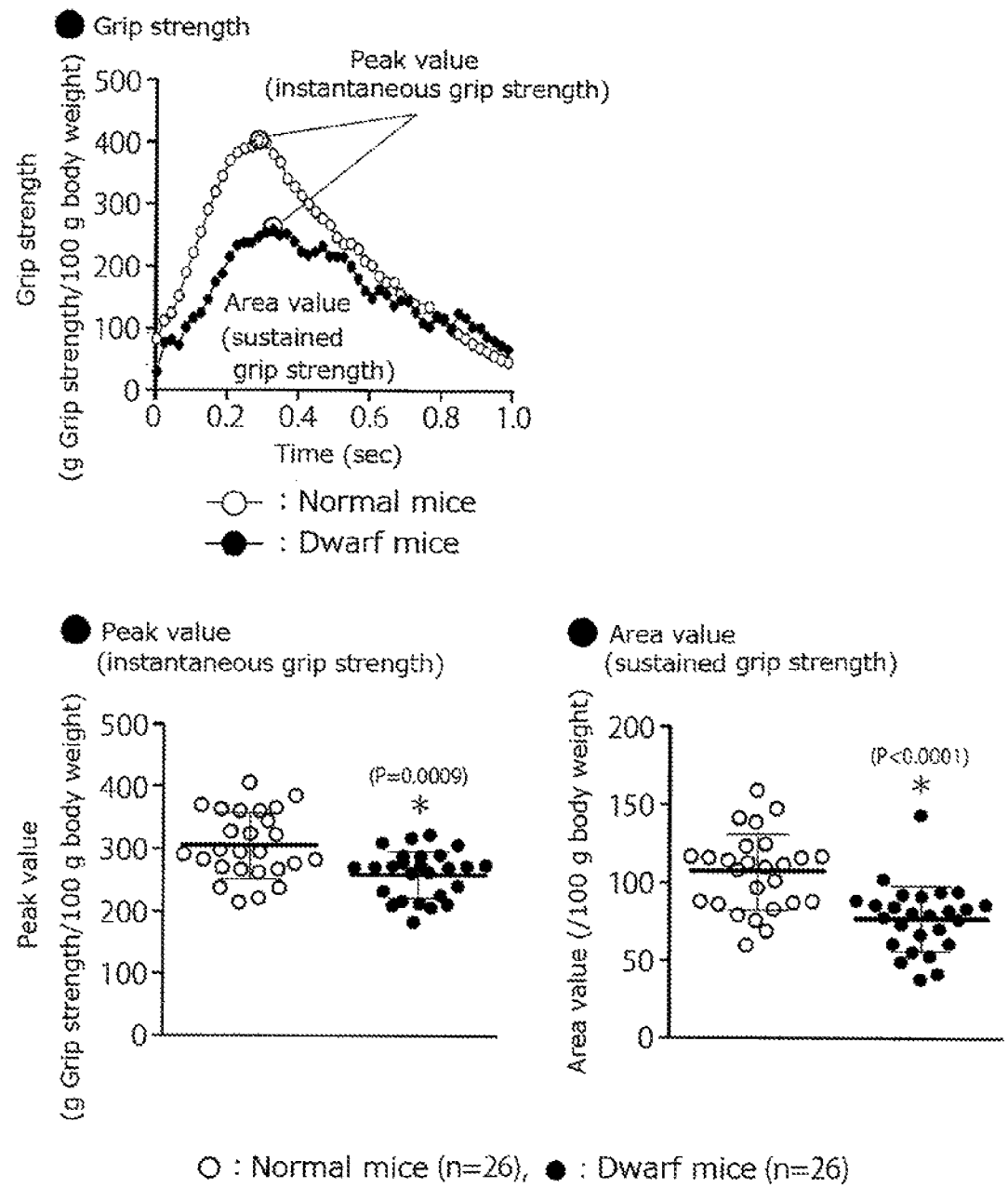
FIG. 13 shows the grip strength of the normal and dwarf mice.

Grip strength of the limbs of the normal and dwarf mice was measured by a device for measuring muscle relaxation of small animals (traction meter, #BS-TM-RM, Brain Science idea). The results are shown in FIG. 13. The instantaneous grip strength and sustained grip strength of the limbs of the dwarf mice were weaker than those of the normal mice.

(16) Anxiety Tendency Determined with Elevated Plus Maze

Figure 14:
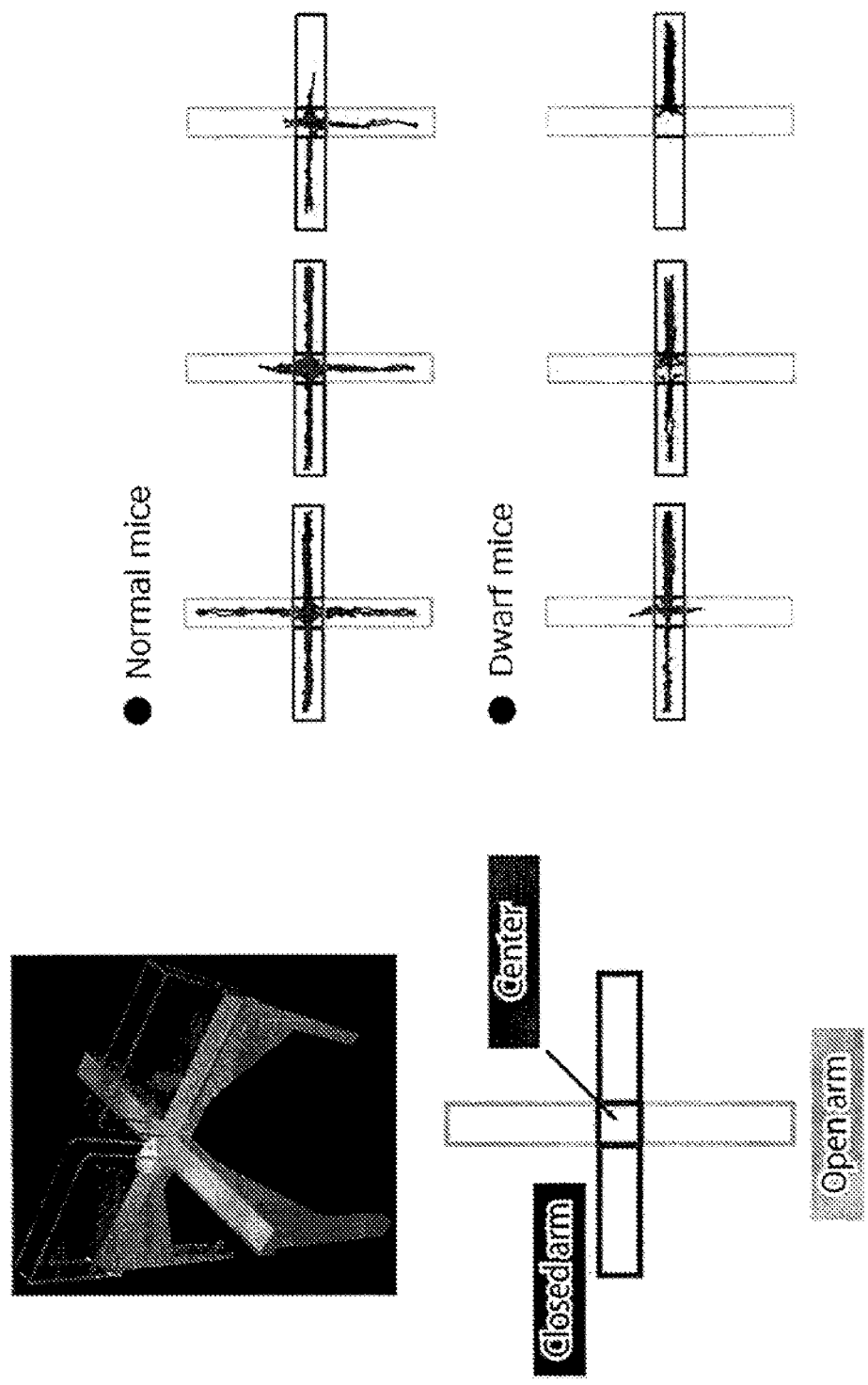
FIG. 14 is a schematic drawing of the method for determining anxiety tendency using an elevated plus maze. The mice were placed at the center of the elevated plus maze and their behavioral trajectories were measured for 10 minutes.
Figure 15:
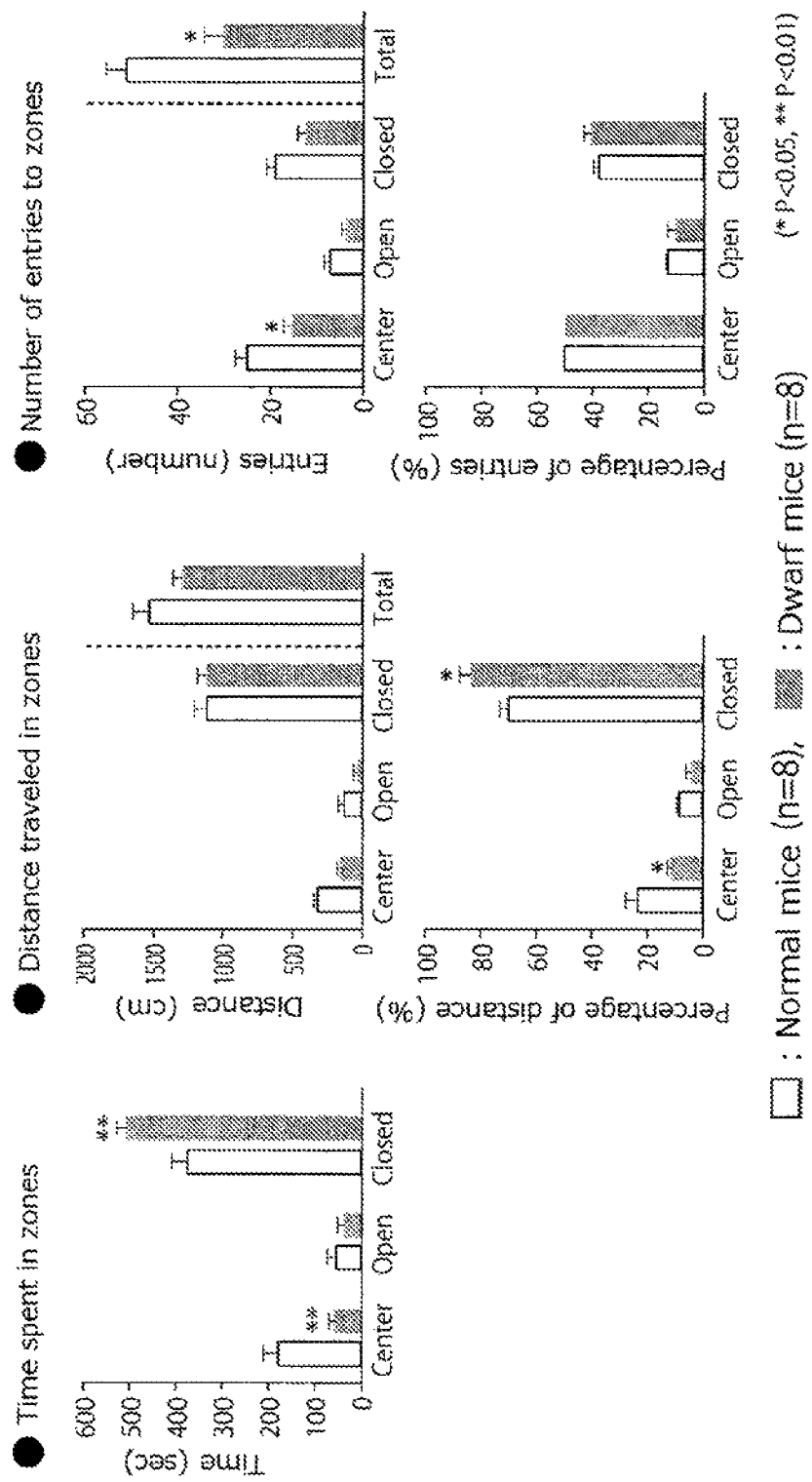
FIG. 15 shows the anxiety tendency of the normal and dwarf mice determined by using the elevated plus maze.

The normal and dwarf mice were placed at the center of an elevated plus maze and their behavioral trajectories were recorded for 10 min (FIG. 14). The results are shown in FIG. 15. There is a possibility that the dwarf mice have higher anxiety levels or less curiosity than the normal mice.

Test 2: Determination of Candidate Disease Gene for Dwarf Mice

Quantitative trait locus (QTL) mapping based on linkage analysis revealed that the gene responsible for the dwarf mouse is located upstream of 38,931,238 bp of chromosome 16. Gene mapping using probes that allow more detailed mapping revealed that the gene responsible for the dwarf mouse is located upstream of 21,678,473 bp of chromosome 16.

Next-generation sequencing was performed within the region identified by the gene mapping to determine the nucleotide sequences. A mutation from CG to C was found at Chr16:4,138,835, which caused frameshift. The result was consistent with the results of sequencing by Sanger method performed in many mice.

SEQ ID NO: 2 and FIGS. 16 and 17 show the nucleotide sequence of the wild-type mouse CREBBP gene. The mutant CREBBP gene found in the dwarf mice lacks the guanine nucleotide corresponding to position 1123 of SEQ ID NO: 1, which is indicated in the square in FIG. 16, and has the nucleotide sequence of SEQ ID NO: 3. FIGS. 18 and 22 show the amino acid sequences of the wild-type CREBBP and mutant CREBBP. The wild-type CREBBP consists of 2441 amino acids, whereas the mutant CREBBP consists of 386 amino acids due to the frameshift. This means the dwarf mice have C-terminus deletion of CREBBP. FIG. 23 shows a part of alignments of the nucleotide and amino acid sequences.

It is known that the CREBBP gene is one of the disease genes of Rubinstein-Taybi syndrome and inherited by autosomal dominant inheritance. Some known complications of Rubinstein-Taybi syndrome, such as short body height, broad nasal crest, and nasal septum extending below the nasal wings, are consistent with features of the dwarf mice. The results indicate that the dwarf mice can be used as a model of Rubinstein-Taybi syndrome.

Test 3: Production of Mice Having the Mutant CREBBP Gene

Genome editing was performed to introduce a point mutation into the following nucleotide sequence of the mouse genome. Exon 4 ENSMUSE00000295066 241 nt

```
                                        (SEQ ID NO: 10)
TCCCAGTTGCAAACATCAGTGGGAATTGTACCCACACAAGCAATTGCAA

CAGGCCCCACAGCAGACCCTGAAAAACGCAAACTGATACAGCAGCAGCT

GGTTCTACTGCTTCATGCCCACAAATGTCAGAGACGAGAGCAAGCAAAT

GGAGAGGTTCGAGCCTGTTCTCTCCCACACTGTCGAACCATGAAAAACG

TTTTGAATCACATGACACATTGTCAGGCTGGGAAAGCCTGCCAAG
```

A sgRNA targeting the nucleotide sequence of ACGAGAGCAAGCAAATGGAG (SEQ ID NO: 9), which is the nucleotide sequence underlined in SEQ ID NO: 10, was used.

In order to introduce the mutation into only one allele of the homologous chromosome and keep another allele intact, two oligonucleotides for knock-in having the following nucleotide sequences were used.

```
                                        (SEQ ID NO: 11)
(1) ssODN for point mutation
TGAAAAACGCAAACTGATACAGCAGCAGCTGGTTCTACTGCTTCATGCC
CACAAATGTCAGAGACGAGAGCAAGCAAATGG-GAGGTTCGAGCCTGTT
CTCTCCCACACTGTCGAACCATGAAAAACGTTTTGAATCACATGACACA
TTGTCAGGCTGGGAA (2) ssODN for silent mutation
                                        (SEQ ID NO: 12)
TGAAAAACGCAAACTGATACAGCAGCAGCTGGTTCTACTGCTTCATGCC
CACAAATGTCAGAGACGAGAGCAAGCAAACGGCGAAGTTCGAGCCTGTT
CTCTCCCACACTGTCGAACCATGAAAAACGTTTTGAATCACATGACACA
TTGTCAGGCTGGGAA
```

To 119 fertilized eggs of B6NJcl, 100 ng/ul of Cas9 protein, 100 ng/ul of sgRNA, and 50 ng/ul each of ssODN (1) and (2) were introduced by electroporation. The next day 110 normally developed embryos were transplanted into four pseudopregnant mice. The four mice spontaneously delivered offspring. Total 31 offspring (10 males and 21 females) were obtained. Genotyping revealed that 10 of 31 offspring were edited, two of which were founder candidates. The founder candidate mice were crossed with B6NJcl mice. The CREBBP gene of the offspring was sequenced and found to have the desired point mutation. Similarly to the spontaneously generated mutant mice, the artificially generated mutant mice had small body size, head deformities, i.e., hypertelorism and short dorsal nasal, and gait abnormalities. The results indicate that the artificially generated mutant mice, as well as the spontaneously generated mutant mice, can be used as a model of Rubinstein-Taybi syndrome.

Test 4: Mutation Detection by Allele-Specific PCR

The following primers and reaction solutions were used to amplify mouse genomic DNA by PCR under the following reaction conditions. The primers were designed to generate an amplification product of 207 bp when the mouse genome has the point mutation identified in Test 2.

Forward primer: 5'-GACGAGAGCAAGCAAATCGG-3' (SEQ ID NO: 13)
Reverse primer: 5'-TAGGCAGTGCAGGATTCCAA-3' (SEQ ID NO: 14)

TABLE 2

Composition of reaction solution

| Component | Amount (µl) |
| --- | --- |
| water | 10 |
| 10x buffer (Agilent) | 2 |
| dNTP (TakaRa) (2.5 mM) | 1.6 |
| Forward primer (10 µM) | 0.4 |
| Reverse primer (10 µM) | 0.4 |
| Genomic DNA | 0.4 |
| Paq5000 polymerase (Agilent) | 0.2 |
| Total | 15 |

TABLE 3

Reaction condition

| Cycle No. | Temperature (° C.) | Time (mm:ss) |
| --- | --- | --- |
| 1 | 95 | 2:00 |
| 35 | 94 | 0:30 |
|  | 63 | 0:30 |
|  | 72 | 1:00 |
| 1 | 72 | 7:00 |
|  | 10 | ∞ |

When genomic DNA of a wild-type mouse was used, no nucleic acid was amplified. When genomic DNA of a spontaneously generated mutant mouse was used, the nucleic acid was amplified. Thus, this system can be used to detect the mutation.

INDUSTRIAL APPLICABILITY

The pathogenesis of Rubinstein-Taybi syndrome is still unknown and no therapeutic method has been established. The disclosed transgenic animal is expected to be used as a research tool. In addition, the disclosure may contribute to the genetic diagnosis of Rubinstein-Taybi syndrome.

What is claimed is:

1. A transgenic mouse having at least one cAMP response element-binding protein-binding protein (CREBBP) gene locus into which a mutation has been introduced and having small body size, hypertelorism, short dorsal nasal, and a gait abnormality, wherein the mutated CREBBP gene encodes a mutant CREBBP consisting of the amino acid sequence of SEQ ID NO: 5.

2. The transgenic mouse according to claim 1, wherein the CREBBP gene comprises a nucleotide sequence that has at least 90% identity with the nucleotide sequence of SEQ ID NO: 1 and lacks a nucleotide corresponding to position 1123 of SEQ ID NO: 1.

3. The transgenic mouse according to claim 1, wherein the CREBBP gene comprises the nucleotide sequence of SEQ ID NO: 7.

* * * * *

SEQUENCE LISTING

<160> NUMBER OF SEQ ID NOS: 14

<210> SEQ ID NO 1
<211> LENGTH: 7326
<212> TYPE: DNA
<213> ORGANISM: Mus musculus

<400> SEQUENCE: 1

```
atggccgaga acttgctgga cggaccgccc aaccccaaac gagccaaact cagctcgccc        60
ggcttctccg cgaatgacaa cacagatttt ggatcattgt ttgacttgga aaatgacctt       120
cctgatgagc tgatccccaa tggagaatta agcctttttaa acagtgggaa ccttgttcca      180
gatgctgcgt ccaaacataa acaactgtca gagcttctta gaggaggcag cggctctagc       240
atcaacccag ggataggcaa tgtgagtgcc agcagccctg tgcaacaggg ccttggtggc       300
caggctcagg ggcagccgaa cagtacaaac atggccagct taggtgccat gggcaagagc       360
cctctgaacc aaggagactc atcaacaccc aacctgccca aacaggcagc cagcacctct       420
gggcccactc ccctgcctc ccaagcactg aatccacaag cacaaaagca agtagggctg       480
gtgaccagta gtcctgccac atcacagact ggacctggga tctgcatgaa tgctaacttc       540
aaccagaccc acccaggcct tctcaatagt aactctggcc atagcttaat gaatcaggct       600
caacaagggc aagctcaagt catgaatgga tctcttgggg ctgctggaag aggaagggga       660
gctggaatgc cctaccctgc tccagccatg caggggggcca caagcagtgt gctggcggag       720
```

```
accttgacac aggttttcccc acaaatggct ggccatgctg gactaaatac agcacaggca      780
ggaggcatga ccaagatggg aatgactggt accacaagtc catttggaca acccctttagt     840 caaactggag ggcagcagat gggagccact ggagtgaacc cccagttagc cagcaaacag      900
agcatggtca atagtttacc tgcttttcct acagatatca agaatacttc agtcaccact      960
gtgccaaata tgtcccagtt gcaaacatca gtgggaattg tacccacaca agcaattgca     1020
acaggcccca cagcagaccc tgaaaaacgc aaactgatac agcagcagct ggttctactg     1080
cttcatgccc acaaatgtca gagacgagag caagcaaatg gagaggttcg agcctgttct     1140
ctcccacact gtcgaaccat gaaaaacgtt ttgaatcaca tgacacattg tcaggctggg     1200
aaagcctgcc aagttgccca ttgtgcatct tcacgacaaa tcatctctca ttggaagaac     1260
tgcacacgac atgactgtcc tgtttgcctc ccttttgaaaa atgccagtga caagcgaaac     1320
caacaaacca tcctgggatc tccagctagt ggaattcaaa acacaattgg ttctgttggt     1380
gcagggcaac agaatgccac ttccttaagt aacccaaatc ccatagaccc cagttccatg     1440
cagcgggcct atgctgctct aggactcccc tacatgaacc agcctcagac gcagctgcag     1500
cctcaggttc ctggccagca accagcacag cctccagccc accagcagat gaggactctc     1560
aatgccctag gaaacaaccc catgagtatc ccagcaggag gaataacaac agatcaacag     1620
ccaccaaact tgatttcaga atcagctctt ccaacttcct tgggggctac caatccactg     1680
atgaatgatg gttcaaactc tggtaacatt ggaagcctca gcacgatacc tacagcagcg     1740
cctccttcca gcactggtgt tcgaaaaggc tggcatgaac atgtgactca ggacctacgg     1800
agtcatctag tccataaact cgttcaagcc atcttcccaa ctccagaccc tgcagctctg     1860
aaagatcgcc gcatggagaa cctggttgcc tatgctaaga agtggaggg agacatgtat     1920 gagtctgcta atagcaggga tgaatactat catttattag cagagaaaat ctataaaata     1980
caaaaagaac tagaagaaaa gcggaggtca cgtttacata agcaaggcat cctgggtaac     2040
cagccagctt taccagcttc tggggctcag cccctgtga ttccaccagc ccagtctgta     2100
agacctccaa atgggcccct gccttttgcca gtgaatcgca tgcaggtttc tcaagggatg     2160
aattcattta acccaatgtc cctgggaaac gtccagttgc cacaggcacc catgggacct     2220
cgtgcagcct cccctatgaa ccactctgtg cagatgaaca gcatggcctc agttccgggt     2280
atggccattt ctccttcacg gatgcctcag cctccaaata tgatgggcac tcatgccaac     2340
aacattatgg cccaggcacc tactcagaac cagtttctgc cacagaacca gtttccatca     2400
tccagtgggg caatgagtgt gaacagtgtg ggcatgggc aaccagcagc ccaggcaggt     2460
gtttcacagg gtcaggtacc tggagctgct ctccctaacc ctctgaacat gctggcaccc     2520
caggccagcc agctgccttg cccaccagtg acacagtcac cattgcaccc gactccacct     2580
cctgcttcca cagctgctgg catgccctct ctccaacatc caacggcacc aggaatgacc     2640
cctcctcagc cagcagctcc cactcagcca tctactcctg tgtcatctgg gcagactcct     2700
accccaactc ctggctcagt gcccagcgct gcccaaacac agagtacccc cacagtccag     2760
gcagcagcac aggctcaggt gactccacag cctcagaccc cagtgcagcc accatctgtg     2820
gctactcctc agtcatcaca gcagcaacca acgcctgtgc atactcagcc tcctggcaca     2880
ccgctttctc aggcagcagc cagcattgat aatagagtcc ctactccctc ctctgtgacc     2940
agtgctgaaa ccagttccca gcagccagga cccgatgtgc ccatgctgga aatgaagaca     3000
gaggtgcaga cagatgatgc tgagcctgaa cctactgaat ccaaggggga acctcggtct     3060
```

```
gagatgatgg aagaggattt acaaggttct tcccaagtaa agaagagac agatacgaca      3120
gagcagaagt cagagccaat ggaagtagaa gaaaagaaac ctgaagtaaa agtggaagct      3180
aaagaggaag aagagaacag ttcgaacgac acagcctcac aatcaacatc tccttcccag      3240
ccacgcaaaa aaatctttaa acccgaggag ctacgccagg cacttatgcc aactctagaa      3300
gcactctatc gacaggaccc agagtctttg ccttttcgtc agcctgtaga tcctcagctc      3360
ctaggaatcc cagattattt tgatatagtg aagaatccta tggaccttc taccatcaaa      3420
cgaaagctgg acacagggca atatcaagaa ccctggcagt atgtggatga tgtctggctt      3480
atgttcaaca atgcgtggct atataatcgt aaaacgtccc gtgtatataa attttgcagt      3540
aaacttgcag aggtctttga caagaaatt gaccctgtca tgcagtctct tggatattgc      3600
tgtggacgaa agtatgagtt ctccccacag actttgtgct gttacggaaa gcagctgtgt      3660
acaattcctc gtgatgcagc ctactacagc tatcagaata ggtatcattt ctgtgagaag      3720
tgtttcacag agatccaggg cgagaatgtg accctgggtg acgacccttc ccaacctcag      3780
acgacaattt ccaaggatca atttgaaaag aagaaaaatg ataccttaga tcctgaacct      3840
tttgttgact gcaaagagtg tggccggaag atgcatcaga tttgtgttct acactatgac      3900
atcatttggc cttcaggttt tgtgtgtgac aactgtttga agaaaactgg cagacctcgg      3960
aaagaaaaca aattcagtgc taagaggctg cagaccacac gattgggaaa ccacttagaa      4020
gacagagtga ataagttttt gcggcgccag aatcaccctg aagctgggga ggtttttgtc      4080
agagtggtgg ccagctcaga caagactgtg gaggtcaagc cgggaatgaa gtcaaggttt      4140
gtggattctg gagagatgtc ggaatctttc ccatatcgta ccaaagcact ctttgctttt      4200
gaggagatcg atggagtcga tgtgtgcttt ttgggatgc atgtgcaaga atacggctct      4260
gattgccccc caccaaatac aaggcgtgta tacatatctt atctggacag tattcattc      4320
ttccggcccc gctgcctccg acagctgtt taccatgaga tcctcatcgg atatctcgag      4380
tatgtgaaga aattggggta tgtgacagga catatttggg cctgtccccc aagtgaagga      4440
gatgactata tctttcattg ccaccccct gaccagaaaa tccccaaacc aaaacgacta      4500
caggagtggt acaagaagat gctggacaag gcgtttgcag agaggatcat taacgactat      4560
aaggacatct tcaaacaagc gaacgaagac aggctcacga gtgccaagga gttgccctat      4620
tttgaaggag atttctggcc taatgtgttg gaagaaagca ttaaggaact agaacaagaa      4680
gaagaagaaa ggaaaaaaga agagagtact gcagcgagtg agactcctga gggcagtcag      4740
ggtgacagca aaaatgcgaa gaaaagaac aacaagaaga ccaacaaaaa caaaagcagc      4800
attagccgcg ccaacaagaa gaagcccagc atgcccaatg tttccaacga cctgtcgcag      4860
aagctgtatg ccaccatgga gaagcacaag gaggtattct ttgtgattca tctgcatgct      4920
gggcctgtta tcagcactca gcccccatc gtggaccctg atcctctgct tagctgtgac      4980
ctcatggatg ggcgagatgc cttcctcacc ctggccagag acaagcactg ggaattctct      5040
tccttacgcc gctccaaatg gtccactctg tgcatgctgg tggagctgca cacacagggc      5100
caggaccgct ttgtttatac ctgcaatgag tgcaaacacc atgtggaaac acgctggcac      5160
tgcactgtgt gtgaggacta tgacctttgt atcaattgct acaacacaaa gagccacacc      5220
cataagatgg tgaagtgggg gctaggccta gatgatgagg gcagcagtca gggtgagcca      5280
cagtccaaga gccccaggga atcccggcgt ctcagcatcc agcgctgcat ccagtccctg      5340
gtgcatgcct gccagtgtcg caatgccaac tgctcactgc cgtcttgcca gagatgaag      5400
cgagtcgtgc agcacaccaa gggctgcaag cgcaagacta atggaggatg cccagtgtgc      5460
```

-continued

```
aagcagctca ttgctctttg ctgctaccac gccaaacact gccaagaaaa taaatgccct    5520
gtgcccttct gcctcaacat caaacataag ctccgccagc agcagatcca gcatcgcctg    5580
cagcaggctc agctcatgcg ccggcgaatg gcaaccatga acacccgcaa tgtgcctcag    5640
cagagtttgc cttctcctac ctcagcacca cccgggactc ctacacagca gcccagcaca    5700
ccccaaacac cacagccccc agcccagcct cagccttcac ctgttaacat gtcaccagct    5760
ggcttcccta atgtagcccg gactcagccc ccaacaatag tgtctgctgg gaagcctacc    5820
aaccaggtgc cagctccccc accccctgcc cagcccccac ctgcagcagt agaagcagcc    5880
cggcaaattg aacgtgaggc ccagcagcag cagcacctat accgagcaaa catcaacaat    5940
ggcatgcccc caggacgtgc aggtatgggg accccaggaa gccaaatgac tcctgtgggc    6000
ctgaatgtgc cccgtcccaa ccaagtcagt gggcctgtca tgtctagtat gccacctggg    6060
cagtggcagc aggcacccat ccctcagcag cagccgatgc aggcatgcc caggcctgta    6120
atgtccatgc aggcccaggc agcagtggct gggccacgga tgcccaatgt gcagccacca    6180
aggagcatct cgccaagtgc cctgcaagac ctgctacgga ccctaaagtc acccagctct    6240
cctcagcagc agcagcaggt gctgaacatc cttaaatcaa acccacagct aatggcagct    6300
ttcatcaaac agcgcacagc caagtatgtg ccaatcagc ctggcatgca gccccagccc    6360
ggacttcaat cccagcctgg tatgcagccc agcctggca tgcaccagca gcctagtttg    6420
caaaacctga acgcaatgca agctggtgtg ccacggcctg gtgtgcctcc accacaacca    6480
gcaatgggag gcctgaatcc ccagggacaa gctctgaaca tcatgaaccc aggacacaac    6540
cccaacatga caaacatgaa tccacagtac cgagaaatgg tgaggagaca gctgctacag    6600
caccagcagc agcagcagca acagcagcag cagcagcagc aacaacaaaa tagtgccagc    6660
ttggccgggg gcatggcggg acacagccag ttccagcagc acaaggacc tggaggttat    6720
gccccagcca tgcagcagca acgcatgcaa cagcacctcc ccatccaggg cagctccatg    6780
ggccagatgg ctgctccaat gggacaactt ggccagatgg ggcagcctgg gctaggggca    6840
gacagcaccc ctaatatcca gcaggccctg cagcaacgga ttctgcagca gcagcagatg    6900
aagcaacaaa ttgggtcacc aggccagccg aaccccatga gccccagca gcacatgctc    6960
tcaggacagc cacaggcctc acatctccct ggccagcaga tcgccacatc ccttagtaac    7020
caggtgcgat ctccagcccc tgtgcagtct ccacggcccc aatcccaacc tccacattcc    7080
agcccgtcac cacggataca accccagcct tcaccacacc atgtttcacc ccagactggt    7140
tcccctcacc ctggactcgc agtcaccatg gccagctcca tggatcaggg cacctgggg    7200
aaccctgaac agagtgcaat gctcccccag ctgaataccc ccaacaggag cgcactgtcc    7260
agtgaactgt ccctggttgg tgataccacg ggagacacac tagaaaagtt tgtggagggt    7320
ttgtag                                                               7326
```

<210> SEQ ID NO 2
<211> LENGTH: 2441
<212> TYPE: PRT
<213> ORGANISM: Mus musculus

<400> SEQUENCE: 2

```
Met Ala Glu Asn Leu Leu Asp Gly Pro Pro Asn Pro Lys Arg Ala Lys
1               5                   10                  15

Leu Ser Ser Pro Gly Phe Ser Ala Asn Asp Asn Thr Asp Phe Gly Ser
            20                  25                  30
```

-continued

```
Leu Phe Asp Leu Glu Asn Asp Leu Pro Asp Glu Leu Ile Pro Asn Gly
         35                  40                  45

Glu Leu Ser Leu Leu Asn Ser Gly Asn Leu Val Pro Asp Ala Ala Ser
 50                  55                  60

Lys His Lys Gln Leu Ser Glu Leu Leu Arg Gly Gly Ser Gly Ser Ser
 65                  70                  75                  80

Ile Asn Pro Gly Ile Gly Asn Val Ser Ala Ser Ser Pro Val Gln Gln
                 85                  90                  95

Gly Leu Gly Gly Gln Ala Gln Gly Gln Pro Asn Ser Thr Asn Met Ala
            100                 105                 110

Ser Leu Gly Ala Met Gly Lys Ser Pro Leu Asn Gln Gly Asp Ser Ser
        115                 120                 125

Thr Pro Asn Leu Pro Lys Gln Ala Ala Ser Thr Ser Gly Pro Thr Pro
    130                 135                 140

Pro Ala Ser Gln Ala Leu Asn Pro Gln Ala Gln Lys Gln Val Gly Leu
145                 150                 155                 160

Val Thr Ser Ser Pro Ala Thr Ser Gln Thr Gly Pro Gly Ile Cys Met
                165                 170                 175

Asn Ala Asn Phe Asn Gln Thr His Pro Gly Leu Leu Asn Ser Asn Ser
            180                 185                 190

Gly His Ser Leu Met Asn Gln Ala Gln Gln Gly Gln Ala Gln Val Met
        195                 200                 205

Asn Gly Ser Leu Gly Ala Ala Gly Arg Gly Arg Gly Ala Gly Met Pro
    210                 215                 220

Tyr Pro Ala Pro Ala Met Gln Gly Ala Thr Ser Ser Val Leu Ala Glu
225                 230                 235                 240

Thr Leu Thr Gln Val Ser Pro Gln Met Ala Gly His Ala Gly Leu Asn
                245                 250                 255

Thr Ala Gln Ala Gly Gly Met Thr Lys Met Gly Met Thr Gly Thr Thr
            260                 265                 270

Ser Pro Phe Gly Gln Pro Phe Ser Gln Thr Gly Gly Gln Gln Met Gly
        275                 280                 285

Ala Thr Gly Val Asn Pro Gln Leu Ala Ser Lys Gln Ser Met Val Asn
    290                 295                 300

Ser Leu Pro Ala Phe Pro Thr Asp Ile Lys Asn Thr Ser Val Thr Thr
305                 310                 315                 320

Val Pro Asn Met Ser Gln Leu Gln Thr Ser Val Gly Ile Val Pro Thr
                325                 330                 335

Gln Ala Ile Ala Thr Gly Pro Thr Ala Asp Pro Glu Lys Arg Lys Leu
            340                 345                 350

Ile Gln Gln Gln Leu Val Leu Leu Leu His Ala His Lys Cys Gln Arg
        355                 360                 365

Arg Glu Gln Ala Asn Gly Glu Val Arg Ala Cys Ser Leu Pro His Cys
    370                 375                 380

Arg Thr Met Lys Asn Val Leu Asn His Met Thr His Cys Gln Ala Gly
385                 390                 395                 400

Lys Ala Cys Gln Val Ala His Cys Ala Ser Ser Arg Gln Ile Ile Ser
                405                 410                 415

His Trp Lys Asn Cys Thr Arg His Asp Cys Pro Val Cys Leu Pro Leu
            420                 425                 430

Lys Asn Ala Ser Asp Lys Arg Asn Gln Gln Thr Ile Leu Gly Ser Pro
        435                 440                 445

Ala Ser Gly Ile Gln Asn Thr Ile Gly Ser Val Gly Ala Gly Gln Gln
```

```
              450               455               460
Asn Ala Thr Ser Leu Ser Asn Pro Asn Pro Ile Asp Pro Ser Ser Met
465                 470                 475                 480

Gln Arg Ala Tyr Ala Ala Leu Gly Leu Pro Tyr Met Asn Gln Pro Gln
                485                 490                 495

Thr Gln Leu Gln Pro Gln Val Pro Gly Gln Pro Ala Gln Pro Pro
            500                 505                 510

Ala His Gln Gln Met Arg Thr Leu Asn Ala Leu Gly Asn Asn Pro Met
            515                 520                 525

Ser Ile Pro Ala Gly Gly Ile Thr Thr Asp Gln Gln Pro Pro Asn Leu
            530                 535                 540

Ile Ser Glu Ser Ala Leu Pro Thr Ser Leu Gly Ala Thr Asn Pro Leu
545                 550                 555                 560

Met Asn Asp Gly Ser Asn Ser Gly Asn Ile Gly Ser Leu Ser Thr Ile
                565                 570                 575

Pro Thr Ala Ala Pro Ser Ser Thr Gly Val Arg Lys Gly Trp His
                580                 585                 590

Glu His Val Thr Gln Asp Leu Arg Ser His Leu Val His Lys Leu Val
            595                 600                 605

Gln Ala Ile Phe Pro Thr Pro Asp Pro Ala Ala Leu Lys Asp Arg Arg
            610                 615                 620

Met Glu Asn Leu Val Ala Tyr Ala Lys Lys Val Glu Gly Asp Met Tyr
625                 630                 635                 640

Glu Ser Ala Asn Ser Arg Asp Glu Tyr Tyr His Leu Leu Ala Glu Lys
                645                 650                 655

Ile Tyr Lys Ile Gln Lys Glu Leu Glu Glu Lys Arg Arg Ser Arg Leu
                660                 665                 670

His Lys Gln Gly Ile Leu Gly Asn Gln Pro Ala Leu Pro Ala Ser Gly
            675                 680                 685

Ala Gln Pro Pro Val Ile Pro Pro Ala Gln Ser Val Arg Pro Pro Asn
690                 695                 700

Gly Pro Leu Pro Leu Pro Val Asn Arg Met Gln Val Ser Gln Gly Met
705                 710                 715                 720

Asn Ser Phe Asn Pro Met Ser Leu Gly Asn Val Gln Leu Pro Gln Ala
                725                 730                 735

Pro Met Gly Pro Arg Ala Ala Ser Pro Met Asn His Ser Val Gln Met
            740                 745                 750

Asn Ser Met Ala Ser Val Pro Gly Met Ala Ile Ser Pro Ser Arg Met
            755                 760                 765

Pro Gln Pro Pro Asn Met Met Gly Thr His Ala Asn Asn Ile Met Ala
            770                 775                 780

Gln Ala Pro Thr Gln Asn Gln Phe Leu Pro Gln Asn Gln Phe Pro Ser
785                 790                 795                 800

Ser Ser Gly Ala Met Ser Val Asn Ser Val Gly Met Gly Gln Pro Ala
                805                 810                 815

Ala Gln Ala Gly Val Ser Gln Gly Gln Val Pro Gly Ala Ala Leu Pro
            820                 825                 830

Asn Pro Leu Asn Met Leu Ala Pro Gln Ala Ser Gln Leu Pro Cys Pro
            835                 840                 845

Pro Val Thr Gln Ser Pro Leu His Pro Thr Pro Pro Ala Ser Thr
            850                 855                 860

Ala Ala Gly Met Pro Ser Leu Gln His Pro Thr Ala Pro Gly Met Thr
865                 870                 875                 880
```

-continued

```
Pro Pro Gln Pro Ala Ala Pro Thr Gln Pro Ser Thr Pro Val Ser Ser
            885                 890                 895

Gly Gln Thr Pro Thr Pro Thr Pro Gly Ser Val Pro Ser Ala Ala Gln
            900                 905                 910

Thr Gln Ser Thr Pro Thr Val Gln Ala Ala Gln Ala Gln Val Thr
            915                 920                 925

Pro Gln Pro Gln Thr Pro Val Gln Pro Pro Ser Val Ala Thr Pro Gln
            930                 935                 940

Ser Ser Gln Gln Gln Pro Thr Pro Val His Thr Gln Pro Pro Gly Thr
945                 950                 955                 960

Pro Leu Ser Gln Ala Ala Ala Ser Ile Asp Asn Arg Val Pro Thr Pro
            965                 970                 975

Ser Ser Val Thr Ser Ala Glu Thr Ser Ser Gln Gln Pro Gly Pro Asp
            980                 985                 990

Val Pro Met Leu Glu Met Lys Thr Glu Val Gln Thr Asp Asp Ala Glu
            995                 1000                1005

Pro Glu Pro Thr Glu Ser Lys Gly Glu Pro Arg Ser Glu Met Met
    1010                1015                1020

Glu Glu Asp Leu Gln Gly Ser Ser Gln Val Lys Glu Glu Thr Asp
    1025                1030                1035

Thr Thr Glu Gln Lys Ser Glu Pro Met Glu Val Glu Glu Lys Lys
    1040                1045                1050

Pro Glu Val Lys Val Glu Ala Lys Glu Glu Glu Asn Ser Ser
    1055                1060                1065

Asn Asp Thr Ala Ser Gln Ser Thr Ser Pro Ser Gln Pro Arg Lys
    1070                1075                1080

Lys Ile Phe Lys Pro Glu Glu Leu Arg Gln Ala Leu Met Pro Thr
    1085                1090                1095

Leu Glu Ala Leu Tyr Arg Gln Asp Pro Glu Ser Leu Pro Phe Arg
    1100                1105                1110

Gln Pro Val Asp Pro Gln Leu Leu Gly Ile Pro Asp Tyr Phe Asp
    1115                1120                1125

Ile Val Lys Asn Pro Met Asp Leu Ser Thr Ile Lys Arg Lys Leu
    1130                1135                1140

Asp Thr Gly Gln Tyr Gln Glu Pro Trp Gln Tyr Val Asp Asp Val
    1145                1150                1155

Trp Leu Met Phe Asn Asn Ala Trp Leu Tyr Asn Arg Lys Thr Ser
    1160                1165                1170

Arg Val Tyr Lys Phe Cys Ser Lys Leu Ala Glu Val Phe Glu Gln
    1175                1180                1185

Glu Ile Asp Pro Val Met Gln Ser Leu Gly Tyr Cys Cys Gly Arg
    1190                1195                1200

Lys Tyr Glu Phe Ser Pro Gln Thr Leu Cys Cys Tyr Gly Lys Gln
    1205                1210                1215

Leu Cys Thr Ile Pro Arg Asp Ala Ala Tyr Tyr Ser Tyr Gln Asn
    1220                1225                1230

Arg Tyr His Phe Cys Glu Lys Cys Phe Thr Glu Ile Gln Gly Glu
    1235                1240                1245

Asn Val Thr Leu Gly Asp Asp Pro Ser Gln Pro Gln Thr Thr Ile
    1250                1255                1260

Ser Lys Asp Gln Phe Glu Lys Lys Lys Asn Asp Thr Leu Asp Pro
    1265                1270                1275
```

-continued

```
Glu Pro Phe Val Asp Cys Lys Glu Cys Gly Arg Lys Met His Gln
1280                1285                1290

Ile Cys Val Leu His Tyr Asp Ile Ile Trp Pro Ser Gly Phe Val
1295                1300                1305

Cys Asp Asn Cys Leu Lys Lys Thr Gly Arg Pro Arg Lys Glu Asn
1310                1315                1320

Lys Phe Ser Ala Lys Arg Leu Gln Thr Thr Arg Leu Gly Asn His
1325                1330                1335

Leu Glu Asp Arg Val Asn Lys Phe Leu Arg Arg Gln Asn His Pro
1340                1345                1350

Glu Ala Gly Glu Val Phe Val Arg Val Val Ala Ser Ser Asp Lys
1355                1360                1365

Thr Val Glu Val Lys Pro Gly Met Lys Ser Arg Phe Val Asp Ser
1370                1375                1380

Gly Glu Met Ser Glu Ser Phe Pro Tyr Arg Thr Lys Ala Leu Phe
1385                1390                1395

Ala Phe Glu Glu Ile Asp Gly Val Asp Val Cys Phe Phe Gly Met
1400                1405                1410

His Val Gln Glu Tyr Gly Ser Asp Cys Pro Pro Pro Asn Thr Arg
1415                1420                1425

Arg Val Tyr Ile Ser Tyr Leu Asp Ser Ile His Phe Phe Arg Pro
1430                1435                1440

Arg Cys Leu Arg Thr Ala Val Tyr His Glu Ile Leu Ile Gly Tyr
1445                1450                1455

Leu Glu Tyr Val Lys Lys Leu Gly Tyr Val Thr Gly His Ile Trp
1460                1465                1470

Ala Cys Pro Pro Ser Glu Gly Asp Asp Tyr Ile Phe His Cys His
1475                1480                1485

Pro Pro Asp Gln Lys Ile Pro Lys Pro Lys Arg Leu Gln Glu Trp
1490                1495                1500

Tyr Lys Lys Met Leu Asp Lys Ala Phe Ala Glu Arg Ile Ile Asn
1505                1510                1515

Asp Tyr Lys Asp Ile Phe Lys Gln Ala Asn Glu Asp Arg Leu Thr
1520                1525                1530

Ser Ala Lys Glu Leu Pro Tyr Phe Glu Gly Asp Phe Trp Pro Asn
1535                1540                1545

Val Leu Glu Glu Ser Ile Lys Glu Leu Glu Gln Glu Glu Glu Glu
1550                1555                1560

Arg Lys Lys Glu Glu Ser Thr Ala Ala Ser Glu Thr Pro Glu Gly
1565                1570                1575

Ser Gln Gly Asp Ser Lys Asn Ala Lys Lys Lys Asn Asn Lys Lys
1580                1585                1590

Thr Asn Lys Asn Lys Ser Ser Ile Ser Arg Ala Asn Lys Lys Lys
1595                1600                1605

Pro Ser Met Pro Asn Val Ser Asn Asp Leu Ser Gln Lys Leu Tyr
1610                1615                1620

Ala Thr Met Glu Lys His Lys Glu Val Phe Phe Val Ile His Leu
1625                1630                1635

His Ala Gly Pro Val Ile Ser Thr Gln Pro Pro Ile Val Asp Pro
1640                1645                1650

Asp Pro Leu Leu Ser Cys Asp Leu Met Asp Gly Arg Asp Ala Phe
1655                1660                1665

Leu Thr Leu Ala Arg Asp Lys His Trp Glu Phe Ser Ser Leu Arg
```

-continued

```
         1670                1675                1680
Arg Ser Lys Trp Ser Thr Leu Cys Met Leu Val Glu Leu His Thr
         1685                1690                1695
Gln Gly Gln Asp Arg Phe Val Tyr Thr Cys Asn Glu Cys Lys His
         1700                1705                1710
His Val Glu Thr Arg Trp His Cys Thr Val Cys Glu Asp Tyr Asp
         1715                1720                1725
Leu Cys Ile Asn Cys Tyr Asn Thr Lys Ser His Thr His Lys Met
         1730                1735                1740
Val Lys Trp Gly Leu Gly Leu Asp Asp Glu Gly Ser Ser Gln Gly
         1745                1750                1755
Glu Pro Gln Ser Lys Ser Pro Gln Glu Ser Arg Arg Leu Ser Ile
         1760                1765                1770
Gln Arg Cys Ile Gln Ser Leu Val His Ala Cys Gln Cys Arg Asn
         1775                1780                1785
Ala Asn Cys Ser Leu Pro Ser Cys Gln Lys Met Lys Arg Val Val
         1790                1795                1800
Gln His Thr Lys Gly Cys Lys Arg Lys Thr Asn Gly Gly Cys Pro
         1805                1810                1815
Val Cys Lys Gln Leu Ile Ala Leu Cys Cys Tyr His Ala Lys His
         1820                1825                1830
Cys Gln Glu Asn Lys Cys Pro Val Pro Phe Cys Leu Asn Ile Lys
         1835                1840                1845
His Lys Leu Arg Gln Gln Ile Gln His Arg Leu Gln Gln Ala
         1850                1855                1860
Gln Leu Met Arg Arg Met Ala Thr Met Asn Thr Arg Asn Val
         1865                1870                1875
Pro Gln Gln Ser Leu Pro Ser Pro Thr Ser Ala Pro Pro Gly Thr
         1880                1885                1890
Pro Thr Gln Gln Pro Ser Thr Pro Gln Thr Pro Gln Pro Pro Ala
         1895                1900                1905
Gln Pro Gln Pro Ser Pro Val Asn Met Ser Pro Ala Gly Phe Pro
         1910                1915                1920
Asn Val Ala Arg Thr Gln Pro Pro Thr Ile Val Ser Ala Gly Lys
         1925                1930                1935
Pro Thr Asn Gln Val Pro Ala Pro Pro Pro Ala Gln Pro Pro
         1940                1945                1950
Pro Ala Ala Val Glu Ala Ala Arg Gln Ile Glu Arg Glu Ala Gln
         1955                1960                1965
Gln Gln Gln His Leu Tyr Arg Ala Asn Ile Asn Asn Gly Met Pro
         1970                1975                1980
Pro Gly Arg Ala Gly Met Gly Thr Pro Gly Ser Gln Met Thr Pro
         1985                1990                1995
Val Gly Leu Asn Val Pro Arg Pro Asn Gln Val Ser Gly Pro Val
         2000                2005                2010
Met Ser Ser Met Pro Pro Gly Gln Trp Gln Gln Ala Pro Ile Pro
         2015                2020                2025
Gln Gln Gln Pro Met Pro Gly Met Pro Arg Pro Val Met Ser Met
         2030                2035                2040
Gln Ala Gln Ala Ala Val Ala Gly Pro Arg Met Pro Asn Val Gln
         2045                2050                2055
Pro Pro Arg Ser Ile Ser Pro Ser Ala Leu Gln Asp Leu Leu Arg
         2060                2065                2070
```

```
Thr Leu Lys Ser Pro Ser Pro Gln Gln Gln Gln Val Leu
    2075            2080            2085

Asn Ile Leu Lys Ser Asn Pro Gln Leu Met Ala Ala Phe Ile Lys
    2090            2095            2100

Gln Arg Thr Ala Lys Tyr Val Ala Asn Gln Pro Gly Met Gln Pro
    2105            2110            2115

Gln Pro Gly Leu Gln Ser Gln Pro Gly Met Gln Pro Gln Pro Gly
    2120            2125            2130

Met His Gln Gln Pro Ser Leu Gln Asn Leu Asn Ala Met Gln Ala
    2135            2140            2145

Gly Val Pro Arg Pro Gly Val Pro Pro Pro Gln Pro Ala Met Gly
    2150            2155            2160

Gly Leu Asn Pro Gln Gly Gln Ala Leu Asn Ile Met Asn Pro Gly
    2165            2170            2175

His Asn Pro Asn Met Thr Asn Met Asn Pro Gln Tyr Arg Glu Met
    2180            2185            2190

Val Arg Arg Gln Leu Leu Gln His Gln Gln Gln Gln Gln Gln Gln
    2195            2200            2205

Gln Gln Gln Gln Gln Gln Gln Asn Ser Ala Ser Leu Ala Gly
    2210            2215            2220

Gly Met Ala Gly His Ser Gln Phe Gln Gln Pro Gln Gly Pro Gly
    2225            2230            2235

Gly Tyr Ala Pro Ala Met Gln Gln Gln Arg Met Gln Gln His Leu
    2240            2245            2250

Pro Ile Gln Gly Ser Ser Met Gly Gln Met Ala Ala Pro Met Gly
    2255            2260            2265

Gln Leu Gly Gln Met Gly Gln Pro Gly Leu Gly Ala Asp Ser Thr
    2270            2275            2280

Pro Asn Ile Gln Gln Ala Leu Gln Gln Arg Ile Leu Gln Gln Gln
    2285            2290            2295

Gln Met Lys Gln Gln Ile Gly Ser Pro Gly Gln Pro Asn Pro Met
    2300            2305            2310

Ser Pro Gln Gln His Met Leu Ser Gly Gln Pro Gln Ala Ser His
    2315            2320            2325

Leu Pro Gly Gln Gln Ile Ala Thr Ser Leu Ser Asn Gln Val Arg
    2330            2335            2340

Ser Pro Ala Pro Val Gln Ser Pro Arg Pro Gln Ser Gln Pro Pro
    2345            2350            2355

His Ser Ser Pro Ser Pro Arg Ile Gln Pro Gln Pro Ser Pro His
    2360            2365            2370

His Val Ser Pro Gln Thr Gly Ser Pro His Pro Gly Leu Ala Val
    2375            2380            2385

Thr Met Ala Ser Ser Met Asp Gln Gly His Leu Gly Asn Pro Glu
    2390            2395            2400

Gln Ser Ala Met Leu Pro Gln Leu Asn Thr Pro Asn Arg Ser Ala
    2405            2410            2415

Leu Ser Ser Glu Leu Ser Leu Val Gly Asp Thr Thr Gly Asp Thr
    2420            2425            2430

Leu Glu Lys Phe Val Glu Gly Leu
    2435            2440

<210> SEQ ID NO 3
<211> LENGTH: 7329
```

<212> TYPE: DNA
<213> ORGANISM: Homo sapiens

<400> SEQUENCE: 3

```
atggctgaga acttgctgga cggaccgccc aaccccaaaa gagccaaact cagctcgccc      60
ggtttctcgg cgaatgacag cacagatttt ggatcattgt ttgacttgga aaatgatctt     120
cctgatgagc tgatacccaa tggaggagaa ttaggccttt aaacagtgg gaaccttgtt     180
ccagatgctg cttccaaaca taaacaactg tcggagcttc tacgaggagg cagcggctct     240
agtatcaacc caggaatagg aaatgtgagc gccagcagcc ccgtgcagca gggcctgggt     300
ggccaggctc aagggcagcc gaacagtgct aacatggcca gcctcagtgc catgggcaag     360
agccctctga ccagggagtt attcttcagcc ccagcctgc ctaaacaggc agccagcacc     420
tctgggccca ccccgctgc ctcccaagca ctgaatccgc aagcacaaaa gcaagtgggg     480
ctggcgacta gcagccctgc cacgtcacag actggacctg gtatctgcat gaatgctaac     540
tttaaccaga cccacccagg cctcctcaat agtaactctg ccatagctt aattaatcag     600
gcttcacaag ggcaggcgca agtcatgaat ggatctcttg gggctgctgg cagaggaagg     660
ggagctggaa tgccgtaccc tactccagcc atgcagggcg cctcgagcag cgtgctggct     720
gagaccctaa cgcaggtttc cccgcaaatg actggtcacg cgggactgaa caccgcacag     780
gcaggaggca tggccaagat gggaataact gggaacacaa gtccatttgg acagcccttt     840
agtcaagctg gagggcagcc aatgggagcc actggagtga ccccccagtt agccagcaaa     900
cagagcatgg tcaacagttt gcccaccttc cctacagata tcaagaatac ttcagtcacc     960
aacgtgccaa atatgtctca gatgcaaaca tcagtgggaa ttgtacccac acaagcaatt    1020
gcaacaggcc ccactgcaga tcctgaaaaa cgcaaactga tacagcagca gctggttcta    1080
ctgcttcatg ctcataagtg tcagagacga gagcaagcaa acggagaggt tcgggcctgc    1140
tcgctcccgc attgtcgaac catgaaaaac gtttttgaatc acatgacgca ttgtcaggct    1200
gggaaagcct gccaagttgc ccattgtgca tcttcacgac aaatcatctc tcattggaag    1260
aactgcacac gacatgactg tcctgttttgc ctccctttga aaaatgccag tgacaagcga    1320
aaccaacaaa ccatcctggg gtctccagct agtggaattc aaaacacaat tggttctgtt    1380
ggcacagggc aacagaatgc cacttctttta gtaacccaa atcccataga ccccagctcc    1440
atgcagcgag cctatgctgc tctcggactc ccctacatga accagcccca gacgcagctg    1500
cagcctcagg ttcctggcca gcaaccagca cagcctcaaa cccaccagca gatgaggact    1560
ctcaaccccc tgggaaataa tccaatgaac attccagcag gaggaataac aacagatcag    1620
cagccccaa acttgatttc agaatcagct cttccgactt ccctgggggc cacaaaccca    1680
ctgatgaacg atggctccaa ctctggtaac attggaaccc tcagcactat accaacagca    1740
gctcctcctt ctagcaccgg tgtaaggaaa ggctggcacg aacatgtcac tcaggacctg    1800
cggagccatc tagtgcataa actcgtccaa gccatcttcc caacacctga tcccgcagct    1860
ctaaaggatc gccgcatgga aaacctggta gcctatgcta agaaagtgga aggggacatg    1920
tacgagtctg ccaacagcag ggatgaatat tatcacttat tagcagagaa aatctacaag    1980
atacaaaaag aactagaaga aaaacggagg tcgcgtttac ataaacaagg catcttgggg    2040
aaccagccag ccttaccagc cccgggggct cagccccctg tgattccaca ggcacaacct    2100
gtgagacctc caaatggacc cctgtccctg ccagtgaatc gcatgcaagt ttctcaaggg    2160
atgaattcat ttaaccccat gtccttgggg aacgtccagt gccacaagc acccatggga    2220
```

```
cctcgtgcag cctccccaat gaaccactct gtccagatga acagcatggg ctcagtgcca    2280
gggatggcca tttctccttc ccgaatgcct cagcctccga acatgatggg tgcacacacc    2340
aacaacatga tggcccaggc gcccgctcag agccagtttc tgccacagaa ccagttcccg    2400
tcatccagcg gggcgatgag tgtgggcatg gggcagccgc cagcccaaac aggcgtgtca    2460
cagggacagg tgcctggtgc tgctcttcct aaccctctca acatgctggg gcctcaggcc    2520
agccagctac cttgccctcc agtgacacag tcaccactgc acccaacacc gcctcctgct    2580
tccacggctg ctggcatgcc atctctccag cacacgacac cacctgggat gactcctccc    2640
cagccagcag ctcccactca gccatcaact cctgtgtcgt cttccgggca gactcccacc    2700
ccgactcctg gctcagtgcc cagtgctacc caaacccaga gcaccctac agtccaggca    2760 gcagcccagg cccaggtgac cccgcagcct caaaccccag ttcagccccc gtctgtggct    2820 accctcagt catcgcagca acagccgacg cctgtgcacg cccagcctcc tggcacaccg    2880 cttcccagg cagcagccag cattgataac agagtcccta ccccctcctc ggtggccagc    2940
gcagaaacca attcccagca gccaggacct gacgtacctg tgctggaaat gaagacggag    3000
acccaagcag aggacactga gcccgatcct ggtgaatcca aggggagcc caggtctgag    3060 atgatggagg aggatttgca aggagcttcc caagttaaag aagaaacaga catagcagag    3120
cagaaatcag aaccaatgga agtggatgaa aagaaacctg aagtgaaagt agaagttaaa    3180
gaggaagaag agagtagcag taacggcaca gcctctcagt caacatctcc ttcgcagccg    3240
cgcaaaaaaa tctttaaacc agaggagtta cgccaggccc tcatgccaac cctagaagca    3300
ctgtatcgac aggacccaga gtcattacct ttccggcagc tgtagatcc ccagctcctc    3360 ggaattccag actattttga catcgtaaag aatcccatgg acctctccac catcaagcgg    3420
aagctggaca cagggcaata ccaagagccc tggcagtacg tggacgacgt ctggctcatg    3480
ttcaacaatg cctggctcta taatcgcaag acatcccgag tctataagtt ttgcagtaag    3540
cttgcagagg tctttgagca ggaaattgac cctgtcatgc agtcccttgg atattgctgt    3600
ggacgcaagt atgagttttc cccacagact ttgtgctgct atgggaagca gctgtgtacc    3660
attcctcgcg atgctgccta ctacagctat cagaataggt atcatttctg tgagaagtgt    3720
ttcacagaga tccagggcga gaatgtgacc ctgggtgacg acccttcaca gccccagacg    3780
acaatttcaa aggatcagtt tgaaaagaag aaaaatgata ccttagaccc cgaacctttc    3840
gttgattgca aggagtgtgg ccggaagatg catcagattt gcgttctgca ctatgacatc    3900
atttggcctt caggttttgt gtgcgacaac tgcttgaaga aactggcag acctcgaaaa    3960 gaaaacaaat tcagtgctaa gaggctgcag accacaagac tgggaaacca cttggaagac    4020
cgagtgaaca aattttgcg gcgccagaat cacccctgaag ccggggaggt ttttgtccga    4080
gtggtggcca gctcagacaa gacggtggag gtcaagcccg ggatgaagtc acggtttgtg    4140
gattctgggg aaatgtctga atcttttccca tatcgaacca agctctgtt tgcttttgag    4200 gaaattgacg gcgtggatgt ctgcttttt ggaatgcacg tccaagaata cggctctgat    4260 tgccccccctc caaacacgag gcgtgtgtac atttcttatc tggatagtat tcatttcttc    4320
cggccacgtt gcctccgcac agccgtttac catgagatcc ttattggata tttagagtat    4380
gtgaagaaat tagggtatgt gacagggcac atctgggcct gtcctccaag tgaaggagat    4440
gattacatct tccattgcca cccacctgat caaaaaatac ccaagccaaa acgactgcag    4500
gagtggtaca aaaagatgct ggacaaggcg tttcagagc ggatcatcca tgactacaag    4560
gatattttca acaagcaac tgaagacagg ctcaccagtg ccaaggaact gcctatttt    4620
```

```
gaaggtgatt tctggcccaa tgtgttagaa gagagcatta aggaactaga acaagaagaa    4680
gaggagagga aaaaggaaga gagcactgca gccagtgaaa ccactgaggg cagtcagggc    4740
gacagcaaga atgccaagaa gaagaacaac aagaaaacca acaagaacaa agcagcatc    4800 agccgcgcca acaagaagaa gcccagcatg cccaacgtgt ccaatgacct gtcccagaag    4860
ctgtatgcca ccatggagaa gcacaaggag gtcttcttcg tgatccacct gcacgctggg    4920
cctgtcatca acaccctgcc ccccatcgtc gaccccgacc cctgctcag ctgtgacctc    4980 atggatgggc gcgacgcctt cctcaccctc gccagagaca agcactggga gttctcctcc    5040
ttgcgccgct ccaagtggtc cacgctctgc atgctggtgg agctgcacac ccagggccag    5100
gaccgctttg tctacacctg caacgagtgc aagcaccacg tggagacgcg ctggcactgc    5160
actgtgtgcg aggactacga cctctgcatc aactgctata acacgaagag ccatgcccat    5220
aagatggtga agtgggggct gggcctggat gacgagggca gcagccaggg cgagccacag    5280
tcaaagagcc cccaggagtc acgccggctg agcatccagc gctgcatcca gtcgctggtg    5340
cacgcgtgcc agtgccgcaa cgccaactgc tcgctgccat cctgccagaa gatgaagcgg    5400
gtggtgcaga acaccaaggg ctgcaaacgc aagaccaacg ggggctgccc ggtgtgcaag    5460
cagctcatcg ccctctgctg ctaccacgcc aagcactgcc aagaaaacaa atgccccgtg    5520
cccttctgcc tcaacatcaa acacaagctc cgccagcagc agatccagca ccgcctgcag    5580
caggcccagc tcatgcgccg gcggatggcc accatgaaca cccgcaacgt gcctcagcag    5640
agtctgcctt ctcctacctc agcaccgccc gggaccccca cacagcagcc cagcacaccc    5700
cagacgccgc agcccctgc ccagccccaa ccctcacccg tgagcatgtc accagctggc    5760
ttccccagcg tggcccggac tcagcccccc accacggtgt ccacagggaa gcctaccagc    5820
caggtgccgg cccccccacc cccggcccag cccctcctg cagcggtgga agcggctcgg    5880
cagatcgagc gtgaggccca gcagcagcag cacctgtacc gggtgaacat caacaacagc    5940
atgcccccag gacgcacggg catggggacc ccggggagcc agatggcccc cgtgagcctg    6000
aatgtgcccc gacccaacca ggtgagcggg cccgtcatgc ccagcatgcc tcccgggcag    6060
tggcagcagg cgccccttcc ccagcagcag cccatgccag gcttgcccag gcctgtgata    6120
tccatgcagg cccaggcggc cgtggctggg ccccggatgc cagcgtgca gccacccagg    6180 agcatctcac ccagcgctct gcaagacctg ctgcggaccc tgaagtcgcc cagctccct    6240 cagcagcaac agcaggtgct gaacattctc aaatcaaacc cgcagctaat ggcagctttc    6300
atcaaacagc gcacagccaa gtacgtggcc aatcagcccg gcatgcagcc ccagcctggc    6360
ctccagtccc agcccggcat gcaaccccag cctggcatgc accagcagcc cagcctgcag    6420
aacctgaatg ccatgcaggc tggcgtgccg cggccggtg tgcctccaca gcagcaggcg    6480
atgggaggcc tgaaccccca gggccaggcc ttgaacatca tgaacccagg acacaacccc    6540
aacatggcga gtatgaatcc acagtaccga gaaatgttac ggaggcagct gctgcagcag    6600
cagcagcaac agcagcagca acaacagcag caacagcagc agcagcaagg gagtgccggc    6660
atggctgggg gcatggcggg gcacggccag ttccagcagc ctcaaggacc cggaggctac    6720
ccaccggcca tgcagcagca gcagcgcatg cagcagcatc tccccctcca gggcagctcc    6780
atgggccaga tggcggctca gatgggacag cttggccaga tggggcagcc ggggctgggg    6840
gcagacagca cccccaacat ccagcaagcc ctgcagcagc ggattctgca gcaacagcag    6900
atgaagcagc agattgggtc cccaggccag ccgaacccca tgagccccca gcaacacatg    6960
```

-continued

```
ctctcaggac agccacaggc ctcgcatctc cctggccagc agatcgccac gtcccttagt    7020
aaccaggtgc ggtctccagc ccctgtccag tctccacggc cccagtccca gcctccacat    7080
tccagcccgt caccacggat acagcccag ccttcgccac accacgtctc accccagact     7140
ggttcccccc accccggact cgcagtcacc atggccagct ccatagatca gggacacttg    7200
gggaaccccg aacagagtgc aatgctcccc cagctgaaca cccccagcag gagtgcgctg    7260
tccagcgaac tgtccctggt cggggacacc acggggggaca cgctagagaa gtttgtggag   7320
ggcttgtag                                                            7329
```

<210> SEQ ID NO 4
<211> LENGTH: 2442
<212> TYPE: PRT
<213> ORGANISM: Homo sapiens

<400> SEQUENCE: 4

```
Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
    130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220

Pro Tyr Pro Thr Pro Ala Met Gln Gly Ala Ser Ser Ser Val Leu Ala
225                 230                 235                 240

Glu Thr Leu Thr Gln Val Ser Pro Gln Met Thr Gly His Ala Gly Leu
                245                 250                 255

Asn Thr Ala Gln Ala Gly Gly Met Ala Lys Met Gly Ile Thr Gly Asn
            260                 265                 270

Thr Ser Pro Phe Gly Gln Pro Phe Ser Gln Ala Gly Gly Gln Pro Met
        275                 280                 285

Gly Ala Thr Gly Val Asn Pro Gln Leu Ala Ser Lys Gln Ser Met Val
    290                 295                 300
```

```
Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
            325                 330                 335

Thr Gln Ala Ile Ala Thr Gly Pro Thr Ala Asp Pro Glu Lys Arg Lys
        340                 345                 350

Leu Ile Gln Gln Gln Leu Val Leu Leu His Ala His Lys Cys Gln
    355                 360                 365

Arg Arg Glu Gln Ala Asn Gly Glu Val Arg Ala Cys Ser Leu Pro His
    370                 375                 380

Cys Arg Thr Met Lys Asn Val Leu Asn His Met Thr His Cys Gln Ala
385                 390                 395                 400

Gly Lys Ala Cys Gln Val Ala His Cys Ala Ser Ser Arg Gln Ile Ile
                405                 410                 415

Ser His Trp Lys Asn Cys Thr Arg His Asp Cys Pro Val Cys Leu Pro
            420                 425                 430

Leu Lys Asn Ala Ser Asp Lys Arg Asn Gln Gln Thr Ile Leu Gly Ser
    435                 440                 445

Pro Ala Ser Gly Ile Gln Asn Thr Ile Gly Ser Val Gly Thr Gly Gln
450                 455                 460

Gln Asn Ala Thr Ser Leu Ser Asn Pro Asn Pro Ile Asp Pro Ser Ser
465                 470                 475                 480

Met Gln Arg Ala Tyr Ala Ala Leu Gly Leu Pro Tyr Met Asn Gln Pro
                485                 490                 495

Gln Thr Gln Leu Gln Pro Gln Val Pro Gly Gln Gln Pro Ala Gln Pro
            500                 505                 510

Gln Thr His Gln Gln Met Arg Thr Leu Asn Pro Leu Gly Asn Asn Pro
        515                 520                 525

Met Asn Ile Pro Ala Gly Gly Ile Thr Thr Asp Gln Gln Pro Pro Asn
530                 535                 540

Leu Ile Ser Glu Ser Ala Leu Pro Thr Ser Leu Gly Ala Thr Asn Pro
545                 550                 555                 560

Leu Met Asn Asp Gly Ser Asn Ser Gly Asn Ile Gly Thr Leu Ser Thr
                565                 570                 575

Ile Pro Thr Ala Ala Pro Pro Ser Ser Thr Gly Val Arg Lys Gly Trp
            580                 585                 590

His Glu His Val Thr Gln Asp Leu Arg Ser His Leu Val His Lys Leu
        595                 600                 605

Val Gln Ala Ile Phe Pro Thr Pro Asp Pro Ala Ala Leu Lys Asp Arg
    610                 615                 620

Arg Met Glu Asn Leu Val Ala Tyr Ala Lys Lys Val Glu Gly Asp Met
625                 630                 635                 640

Tyr Glu Ser Ala Asn Ser Arg Asp Glu Tyr Tyr His Leu Leu Ala Glu
                645                 650                 655

Lys Ile Tyr Lys Ile Gln Lys Glu Leu Glu Glu Lys Arg Arg Ser Arg
            660                 665                 670

Leu His Lys Gln Gly Ile Leu Gly Asn Gln Pro Ala Leu Pro Ala Pro
        675                 680                 685

Gly Ala Gln Pro Pro Val Ile Pro Gln Ala Gln Pro Val Arg Pro Pro
    690                 695                 700

Asn Gly Pro Leu Ser Leu Pro Val Asn Arg Met Gln Val Ser Gln Gly
705                 710                 715                 720

Met Asn Ser Phe Asn Pro Met Ser Leu Gly Asn Val Gln Leu Pro Gln
```

```
                   725                 730                 735
Ala Pro Met Gly Pro Arg Ala Ala Ser Pro Met Asn His Ser Val Gln
                740                 745                 750
Met Asn Ser Met Gly Ser Val Pro Gly Met Ala Ile Ser Pro Ser Arg
                755                 760                 765
Met Pro Gln Pro Pro Asn Met Met Gly Ala His Thr Asn Asn Met Met
                770                 775                 780
Ala Gln Ala Pro Ala Gln Ser Gln Phe Leu Pro Gln Asn Gln Phe Pro
785                 790                 795                 800
Ser Ser Ser Gly Ala Met Ser Val Gly Met Gly Gln Pro Pro Ala Gln
                805                 810                 815
Thr Gly Val Ser Gln Gly Gln Val Pro Gly Ala Ala Leu Pro Asn Pro
                820                 825                 830
Leu Asn Met Leu Gly Pro Gln Ala Ser Gln Leu Pro Cys Pro Pro Val
                835                 840                 845
Thr Gln Ser Pro Leu His Pro Thr Pro Pro Ala Ser Thr Ala Ala
                850                 855                 860
Gly Met Pro Ser Leu Gln His Thr Thr Pro Pro Gly Met Thr Pro Pro
865                 870                 875                 880
Gln Pro Ala Ala Pro Thr Gln Pro Ser Thr Pro Val Ser Ser Gly
                885                 890                 895
Gln Thr Pro Thr Pro Thr Pro Gly Ser Val Pro Ser Ala Thr Gln Thr
                900                 905                 910
Gln Ser Thr Pro Thr Val Gln Ala Ala Ala Gln Ala Gln Val Thr Pro
                915                 920                 925
Gln Pro Gln Thr Pro Val Gln Pro Pro Ser Val Ala Thr Pro Gln Ser
                930                 935                 940
Ser Gln Gln Gln Pro Thr Pro Val His Ala Gln Pro Pro Gly Thr Pro
945                 950                 955                 960
Leu Ser Gln Ala Ala Ala Ser Ile Asp Asn Arg Val Pro Thr Pro Ser
                965                 970                 975
Ser Val Ala Ser Ala Glu Thr Asn Ser Gln Gln Pro Gly Pro Asp Val
                980                 985                 990
Pro Val Leu Glu Met Lys Thr Glu Thr Gln Ala Glu Asp Thr Glu Pro
                995                 1000                1005
Asp Pro Gly Glu Ser Lys Gly Glu Pro Arg Ser Glu Met Met Glu
                1010                1015                1020
Glu Asp Leu Gln Gly Ala Ser Gln Val Lys Glu Glu Thr Asp Ile
                1025                1030                1035
Ala Glu Gln Lys Ser Glu Pro Met Glu Val Asp Glu Lys Lys Pro
                1040                1045                1050
Glu Val Lys Val Glu Val Lys Glu Glu Glu Glu Ser Ser Ser Asn
                1055                1060                1065
Gly Thr Ala Ser Gln Ser Thr Ser Pro Ser Gln Pro Arg Lys Lys
                1070                1075                1080
Ile Phe Lys Pro Glu Glu Leu Arg Gln Ala Leu Met Pro Thr Leu
                1085                1090                1095
Glu Ala Leu Tyr Arg Gln Asp Pro Glu Ser Leu Pro Phe Arg Gln
                1100                1105                1110
Pro Val Asp Pro Gln Leu Leu Gly Ile Pro Asp Tyr Phe Asp Ile
                1115                1120                1125
Val Lys Asn Pro Met Asp Leu Ser Thr Ile Lys Arg Lys Leu Asp
                1130                1135                1140
```

-continued

Thr Gly Gln Tyr Gln Glu Pro Trp Gln Tyr Val Asp Asp Val Trp
1145                1150                1155

Leu Met Phe Asn Asn Ala Trp Leu Tyr Asn Arg Lys Thr Ser Arg
1160                1165                1170

Val Tyr Lys Phe Cys Ser Lys Leu Ala Glu Val Phe Glu Gln Glu
1175                1180                1185

Ile Asp Pro Val Met Gln Ser Leu Gly Tyr Cys Cys Gly Arg Lys
1190                1195                1200

Tyr Glu Phe Ser Pro Gln Thr Leu Cys Cys Tyr Gly Lys Gln Leu
1205                1210                1215

Cys Thr Ile Pro Arg Asp Ala Ala Tyr Tyr Ser Tyr Gln Asn Arg
1220                1225                1230

Tyr His Phe Cys Glu Lys Cys Phe Thr Glu Ile Gln Gly Glu Asn
1235                1240                1245

Val Thr Leu Gly Asp Asp Pro Ser Gln Pro Gln Thr Thr Ile Ser
1250                1255                1260

Lys Asp Gln Phe Glu Lys Lys Asn Asp Thr Leu Asp Pro Glu
1265                1270                1275

Pro Phe Val Asp Cys Lys Glu Cys Gly Arg Lys Met His Gln Ile
1280                1285                1290

Cys Val Leu His Tyr Asp Ile Ile Trp Pro Ser Gly Phe Val Cys
1295                1300                1305

Asp Asn Cys Leu Lys Lys Thr Gly Arg Pro Arg Lys Glu Asn Lys
1310                1315                1320

Phe Ser Ala Lys Arg Leu Gln Thr Thr Arg Leu Gly Asn His Leu
1325                1330                1335

Glu Asp Arg Val Asn Lys Phe Leu Arg Arg Gln Asn His Pro Glu
1340                1345                1350

Ala Gly Glu Val Phe Val Arg Val Val Ala Ser Ser Asp Lys Thr
1355                1360                1365

Val Glu Val Lys Pro Gly Met Lys Ser Arg Phe Val Asp Ser Gly
1370                1375                1380

Glu Met Ser Glu Ser Phe Pro Tyr Arg Thr Lys Ala Leu Phe Ala
1385                1390                1395

Phe Glu Glu Ile Asp Gly Val Asp Val Cys Phe Phe Gly Met His
1400                1405                1410

Val Gln Glu Tyr Gly Ser Asp Cys Pro Pro Pro Asn Thr Arg Arg
1415                1420                1425

Val Tyr Ile Ser Tyr Leu Asp Ser Ile His Phe Phe Arg Pro Arg
1430                1435                1440

Cys Leu Arg Thr Ala Val Tyr His Glu Ile Leu Ile Gly Tyr Leu
1445                1450                1455

Glu Tyr Val Lys Lys Leu Gly Tyr Val Thr Gly His Ile Trp Ala
1460                1465                1470

Cys Pro Pro Ser Glu Gly Asp Asp Tyr Ile Phe His Cys His Pro
1475                1480                1485

Pro Asp Gln Lys Ile Pro Lys Pro Lys Arg Leu Gln Glu Trp Tyr
1490                1495                1500

Lys Lys Met Leu Asp Lys Ala Phe Ala Glu Arg Ile Ile His Asp
1505                1510                1515

Tyr Lys Asp Ile Phe Lys Gln Ala Thr Glu Asp Arg Leu Thr Ser
1520                1525                1530

```
Ala Lys Glu Leu Pro Tyr Phe Glu Gly Asp Phe Trp Pro Asn Val
1535                1540                1545

Leu Glu Glu Ser Ile Lys Glu Leu Glu Gln Glu Glu Glu Glu Arg
1550                1555                1560

Lys Lys Glu Glu Ser Thr Ala Ala Ser Glu Thr Thr Glu Gly Ser
1565                1570                1575

Gln Gly Asp Ser Lys Asn Ala Lys Lys Lys Asn Asn Lys Lys Thr
1580                1585                1590

Asn Lys Asn Lys Ser Ser Ile Ser Arg Ala Asn Lys Lys Lys Pro
1595                1600                1605

Ser Met Pro Asn Val Ser Asn Asp Leu Ser Gln Lys Leu Tyr Ala
1610                1615                1620

Thr Met Glu Lys His Lys Glu Val Phe Phe Val Ile His Leu His
1625                1630                1635

Ala Gly Pro Val Ile Asn Thr Leu Pro Pro Ile Val Asp Pro Asp
1640                1645                1650

Pro Leu Leu Ser Cys Asp Leu Met Asp Gly Arg Asp Ala Phe Leu
1655                1660                1665

Thr Leu Ala Arg Asp Lys His Trp Glu Phe Ser Ser Leu Arg Arg
1670                1675                1680

Ser Lys Trp Ser Thr Leu Cys Met Leu Val Glu Leu His Thr Gln
1685                1690                1695

Gly Gln Asp Arg Phe Val Tyr Thr Cys Asn Glu Cys Lys His His
1700                1705                1710

Val Glu Thr Arg Trp His Cys Thr Val Cys Glu Asp Tyr Asp Leu
1715                1720                1725

Cys Ile Asn Cys Tyr Asn Thr Lys Ser His Ala His Lys Met Val
1730                1735                1740

Lys Trp Gly Leu Gly Leu Asp Asp Glu Gly Ser Ser Gln Gly Glu
1745                1750                1755

Pro Gln Ser Lys Ser Pro Gln Glu Ser Arg Arg Leu Ser Ile Gln
1760                1765                1770

Arg Cys Ile Gln Ser Leu Val His Ala Cys Gln Cys Arg Asn Ala
1775                1780                1785

Asn Cys Ser Leu Pro Ser Cys Gln Lys Met Lys Arg Val Val Gln
1790                1795                1800

His Thr Lys Gly Cys Lys Arg Lys Thr Asn Gly Gly Cys Pro Val
1805                1810                1815

Cys Lys Gln Leu Ile Ala Leu Cys Cys Tyr His Ala Lys His Cys
1820                1825                1830

Gln Glu Asn Lys Cys Pro Val Pro Phe Cys Leu Asn Ile Lys His
1835                1840                1845

Lys Leu Arg Gln Gln Gln Ile Gln His Arg Leu Gln Gln Ala Gln
1850                1855                1860

Leu Met Arg Arg Arg Met Ala Thr Met Asn Thr Arg Asn Val Pro
1865                1870                1875

Gln Gln Ser Leu Pro Ser Pro Thr Ser Ala Pro Pro Gly Thr Pro
1880                1885                1890

Thr Gln Gln Pro Ser Thr Pro Gln Thr Pro Gln Pro Pro Ala Gln
1895                1900                1905

Pro Gln Pro Ser Pro Val Ser Met Ser Pro Ala Gly Phe Pro Ser
1910                1915                1920

Val Ala Arg Thr Gln Pro Pro Thr Thr Val Ser Thr Gly Lys Pro
```

```
                1925                1930                1935

Thr Ser  Gln Val Pro Ala Pro  Pro Pro Ala Gln  Pro Pro Pro
    1940             1945                 1950

Ala Ala  Val Glu Ala Ala Arg  Gln Ile Glu Arg  Glu Ala Gln Gln
    1955             1960                 1965

Gln Gln  His Leu Tyr Arg Val  Asn Ile Asn Asn  Ser Met Pro Pro
    1970             1975                 1980

Gly Arg  Thr Gly Met Gly Thr  Pro Gly Ser Gln  Met Ala Pro Val
    1985             1990                 1995

Ser Leu  Asn Val Pro Arg Pro  Asn Gln Val Ser  Gly Pro Val Met
    2000             2005                 2010

Pro Ser  Met Pro Pro Gly Gln  Trp Gln Gln Ala  Pro Leu Pro Gln
    2015             2020                 2025

Gln Gln  Pro Met Pro Gly Leu  Pro Arg Pro Val  Ile Ser Met Gln
    2030             2035                 2040

Ala Gln  Ala Ala Val Ala Gly  Pro Arg Met Pro  Ser Val Gln Pro
    2045             2050                 2055

Pro Arg  Ser Ile Ser Pro Ser  Ala Leu Gln Asp  Leu Leu Arg Thr
    2060             2065                 2070

Leu Lys  Ser Pro Ser Ser Pro  Gln Gln Gln Gln  Val Leu Asn
    2075             2080                 2085

Ile Leu  Lys Ser Asn Pro Gln  Leu Met Ala Ala  Phe Ile Lys Gln
    2090             2095                 2100

Arg Thr  Ala Lys Tyr Val Ala  Asn Gln Pro Gly  Met Gln Pro Gln
    2105             2110                 2115

Pro Gly  Leu Gln Ser Gln Pro  Gly Met Gln Pro  Gln Pro Gly Met
    2120             2125                 2130

His Gln  Gln Pro Ser Leu Gln  Asn Leu Asn Ala  Met Gln Ala Gly
    2135             2140                 2145

Val Pro  Arg Pro Gly Val Pro  Pro Gln Gln Ala  Met Gly Gly
    2150             2155                 2160

Leu Asn  Pro Gln Gly Gln Ala  Leu Asn Ile Met  Asn Pro Gly His
    2165             2170                 2175

Asn Pro  Asn Met Ala Ser Met  Asn Pro Gln Tyr  Arg Glu Met Leu
    2180             2185                 2190

Arg Arg  Gln Leu Leu Gln Gln  Gln Gln Gln Gln  Gln Gln Gln
    2195             2200                 2205

Gln Gln  Gln Gln Gln Gln Gln  Gln Gly Ser Ala  Gly Met Ala Gly
    2210             2215                 2220

Gly Met  Ala Gly His Gly Gln  Phe Gln Gln Pro  Gln Gly Pro Gly
    2225             2230                 2235

Gly Tyr  Pro Pro Ala Met Gln  Gln Gln Gln Arg  Met Gln Gln His
    2240             2245                 2250

Leu Pro  Leu Gln Gly Ser Ser  Met Gly Gln Met  Ala Ala Gln Met
    2255             2260                 2265

Gly Gln  Leu Gly Gln Met Gly  Gln Pro Gly Leu  Gly Ala Asp Ser
    2270             2275                 2280

Thr Pro  Asn Ile Gln Gln Ala  Leu Gln Gln Arg  Ile Leu Gln Gln
    2285             2290                 2295

Gln Gln  Met Lys Gln Gln Ile  Gly Ser Pro Gly  Gln Pro Asn Pro
    2300             2305                 2310

Met Ser  Pro Gln Gln His Met  Leu Ser Gly Gln  Pro Gln Ala Ser
    2315             2320                 2325
```

His Leu Pro Gly Gln Gln Ile Ala Thr Ser Leu Ser Asn Gln Val
    2330                2335                2340

Arg Ser Pro Ala Pro Val Gln Ser Pro Arg Pro Gln Ser Gln Pro
    2345                2350                2355

Pro His Ser Pro Ser Pro Arg Ile Gln Pro Gln Pro Ser Pro
    2360                2365                2370

His His Val Ser Pro Gln Thr Gly Ser Pro His Pro Gly Leu Ala
    2375                2380                2385

Val Thr Met Ala Ser Ser Ile Asp Gln Gly His Leu Gly Asn Pro
    2390                2395                2400

Glu Gln Ser Ala Met Leu Pro Gln Leu Asn Thr Pro Ser Arg Ser
    2405                2410                2415

Ala Leu Ser Ser Glu Leu Ser Leu Val Gly Asp Thr Thr Gly Asp
    2420                2425                2430

Thr Leu Glu Lys Phe Val Glu Gly Leu
    2435                2440

<210> SEQ ID NO 5
<211> LENGTH: 386
<212> TYPE: PRT
<213> ORGANISM: Mus musculus

<400> SEQUENCE: 5

Met Ala Glu Asn Leu Leu Asp Gly Pro Pro Asn Pro Lys Arg Ala Lys
1               5                   10                  15

Leu Ser Ser Pro Gly Phe Ser Ala Asn Asp Asn Thr Asp Phe Gly Ser
            20                  25                  30

Leu Phe Asp Leu Glu Asn Asp Leu Pro Asp Glu Leu Ile Pro Asn Gly
        35                  40                  45

Glu Leu Ser Leu Leu Asn Ser Gly Asn Leu Val Pro Asp Ala Ala Ser
    50                  55                  60

Lys His Lys Gln Leu Ser Glu Leu Leu Arg Gly Gly Ser Gly Ser Ser
65                  70                  75                  80

Ile Asn Pro Gly Ile Gly Asn Val Ser Ala Ser Ser Pro Val Gln Gln
                85                  90                  95

Gly Leu Gly Gly Gln Ala Gln Gly Gln Pro Asn Ser Thr Asn Met Ala
            100                 105                 110

Ser Leu Gly Ala Met Gly Lys Ser Pro Leu Asn Gln Gly Asp Ser Ser
        115                 120                 125

Thr Pro Asn Leu Pro Lys Gln Ala Ala Ser Thr Ser Gly Pro Thr Pro
    130                 135                 140

Pro Ala Ser Gln Ala Leu Asn Pro Gln Ala Gln Lys Gln Val Gly Leu
145                 150                 155                 160

Val Thr Ser Ser Pro Ala Thr Ser Gln Thr Gly Pro Gly Ile Cys Met
                165                 170                 175

Asn Ala Asn Phe Asn Gln Thr His Pro Gly Leu Leu Asn Ser Asn Ser
            180                 185                 190

Gly His Ser Leu Met Asn Gln Ala Gln Gln Gly Gln Ala Gln Val Met
        195                 200                 205

Asn Gly Ser Leu Gly Ala Ala Gly Arg Gly Arg Gly Ala Gly Met Pro
    210                 215                 220

Tyr Pro Ala Pro Ala Met Gln Gly Ala Thr Ser Ser Val Leu Ala Glu
225                 230                 235                 240

Thr Leu Thr Gln Val Ser Pro Gln Met Ala Gly His Ala Gly Leu Asn

-continued

```
                        245                 250                 255
Thr Ala Gln Ala Gly Gly Met Thr Lys Met Gly Met Thr Gly Thr Thr
            260                 265                 270

Ser Pro Phe Gly Gln Pro Phe Ser Gln Thr Gly Gly Gln Gln Met Gly
        275                 280                 285

Ala Thr Gly Val Asn Pro Gln Leu Ala Ser Lys Gln Ser Met Val Asn
    290                 295                 300

Ser Leu Pro Ala Phe Pro Thr Asp Ile Lys Asn Thr Ser Val Thr Thr
305                 310                 315                 320

Val Pro Asn Met Ser Gln Leu Gln Thr Ser Val Gly Ile Val Pro Thr
                325                 330                 335

Gln Ala Ile Ala Thr Gly Pro Thr Ala Asp Pro Glu Lys Arg Lys Leu
            340                 345                 350

Ile Gln Gln Gln Leu Val Leu Leu Leu His Ala His Lys Cys Gln Arg
        355                 360                 365

Arg Glu Gln Ala Asn Gly Arg Phe Glu Pro Val Leu Ser His Thr Val
    370                 375                 380

Glu Pro
385

<210> SEQ ID NO 6
<211> LENGTH: 387
<212> TYPE: PRT
<213> ORGANISM: Homo sapiens

<400> SEQUENCE: 6

Met Ala Glu Asn Leu Leu Asp Gly Pro Pro Asn Pro Lys Arg Ala Lys
1               5                   10                  15

Leu Ser Ser Pro Gly Phe Ser Ala Asn Asp Ser Thr Asp Phe Gly Ser
            20                  25                  30

Leu Phe Asp Leu Glu Asn Asp Leu Pro Asp Glu Leu Ile Pro Asn Gly
        35                  40                  45

Gly Glu Leu Gly Leu Leu Asn Ser Gly Asn Leu Val Pro Asp Ala Ala
    50                  55                  60

Ser Lys His Lys Gln Leu Ser Glu Leu Leu Arg Gly Gly Ser Gly Ser
65                  70                  75                  80

Ser Ile Asn Pro Gly Ile Gly Asn Val Ser Ala Ser Ser Pro Val Gln
                85                  90                  95

Gln Gly Leu Gly Gly Gln Ala Gln Gly Gln Pro Asn Ser Ala Asn Met
            100                 105                 110

Ala Ser Leu Ser Ala Met Gly Lys Ser Pro Leu Ser Gln Gly Asp Ser
        115                 120                 125

Ser Ala Pro Ser Leu Pro Lys Gln Ala Ala Ser Thr Ser Gly Pro Thr
    130                 135                 140

Pro Ala Ala Ser Gln Ala Leu Asn Pro Gln Ala Gln Lys Gln Val Gly
145                 150                 155                 160

Leu Ala Thr Ser Ser Pro Ala Thr Ser Gln Thr Gly Pro Gly Ile Cys
                165                 170                 175

Met Asn Ala Asn Phe Asn Gln Thr His Pro Gly Leu Leu Asn Ser Asn
            180                 185                 190

Ser Gly His Ser Leu Ile Asn Gln Ala Ser Gln Gly Gln Ala Gln Val
        195                 200                 205

Met Asn Gly Ser Leu Gly Ala Ala Gly Arg Gly Arg Gly Ala Gly Met
    210                 215                 220
```

```
Pro Tyr Pro Thr Pro Ala Met Gln Gly Ala Ser Ser Val Leu Ala
225                 230                 235                 240

Glu Thr Leu Thr Gln Val Ser Pro Gln Met Thr Gly His Ala Gly Leu
            245                 250                 255

Asn Thr Ala Gln Ala Gly Gly Met Ala Lys Met Gly Ile Thr Gly Asn
        260                 265                 270

Thr Ser Pro Phe Gly Gln Pro Phe Ser Gln Ala Gly Gly Gln Pro Met
    275                 280                 285

Gly Ala Thr Gly Val Asn Pro Gln Leu Ala Ser Lys Gln Ser Met Val
290                 295                 300

Asn Ser Leu Pro Thr Phe Pro Thr Asp Ile Lys Asn Thr Ser Val Thr
305                 310                 315                 320

Asn Val Pro Asn Met Ser Gln Met Gln Thr Ser Val Gly Ile Val Pro
                325                 330                 335

Thr Gln Ala Ile Ala Thr Gly Pro Thr Ala Asp Pro Glu Lys Arg Lys
            340                 345                 350

Leu Ile Gln Gln Gln Leu Val Leu Leu Leu His Ala His Lys Cys Gln
        355                 360                 365

Arg Arg Glu Gln Ala Asn Gly Arg Phe Gly Pro Ala Arg Ser Arg Ile
370                 375                 380

Val Glu Pro
385

<210> SEQ ID NO 7
<211> LENGTH: 7325
<212> TYPE: DNA
<213> ORGANISM: Mus musculus

<400> SEQUENCE: 7
atggccgaga acttgctgga cggaccgccc aaccccaaac gagccaaact cagctcgccc      60
ggcttctccg cgaatgacaa cacagatttt ggatcattgt ttgacttgga aaatgacctt     120
cctgatgagc tgatccccaa tggagaatta agccttttaa acagtgggaa ccttgttcca     180
gatgctgcgt ccaaacataa acaactgtca gagcttctta gaggaggcag cggctctagc     240
atcaacccag ggataggcaa tgtgagtgcc agcagccctg tgcaacaggg ccttggtggc     300
caggctcagg ggcagccgaa cagtacaaac atggccagct taggtgccat gggcaagagc     360
cctctgaacc aaggagactc atcaacaccc aacctgccca acaggcagc cagcacctct     420 gggcccactc cccctgcctc ccaagcactg aatccacaag cacaaaagca agtagggctg     480
gtgaccagta gtcctgccac atcacagact ggacctggga tctgcatgaa tgctaacttc     540
aaccagaccc acccaggcct tctcaatagt aactctggcc atagcttaat gaatcaggct     600
caacaagggc aagctcaagt catgaatgga tctcttgggg ctgctggaag aggaaggggg     660
gctggaatgc cctaccctgc tccagccatg caggggcca caagcagtgt gctggcggag     720
accttgacac aggtttcccc acaaatggct ggccatgctg gactaaatac agcacaggca     780
ggaggcatga ccaagatggg aatgactggt accacaagtc catttggaca acccttagt     840 caaactggag gcagcagat gggagccact ggagtgaacc cccagttagc cagcaaacag     900
agcatggtca atagtttacc tgcttttcct acagatatca gaatacttc agtcaccact     960 gtgccaaata tgtcccagtt gcaaacatca gtgggaattg tacccacaca agcaattgca    1020
acaggcccca cagcagaccc tgaaaaacgc aaactgatac agcagcagct ggttctactg    1080
cttcatgccc acaaatgtca gagacgagag caagcaaatg gaaggttcga gcctgttctc    1140
```

```
tcccacactg tcgaaccatg aaaaacgttt tgaatcacat gacacattgt caggctggga    1200
aagcctgcca agttgcccat tgtgcatctt cacgacaaat catctctcat tggaagaact    1260
gcacacgaca tgactgtcct gtttgcctcc ctttgaaaaa tgccagtgac aagcgaaacc    1320
aacaaaccat cctgggatct ccagctagtg gaattcaaaa cacaattggt tctgttggtg    1380
cagggcaaca gaatgccact tccttaagta acccaaatcc catagacccc agttccatgc    1440
agcgggccta tgctgctcta ggactcccct acatgaacca gcctcagacg cagctgcagc    1500
ctcaggttcc tggccagcaa ccagcacagc ctccagccca ccagcagatg aggactctca    1560
atgccctagg aaacaaccCC atgagtatcc cagcaggagg aataacaaca gatcaacagc    1620
caccaaactt gatttcagaa tcagctcttc caacttcctt gggggctacc aatccactga    1680
tgaatgatgg ttcaaaactct ggtaacattg gaagcctcag cacgatacct acagcagcgc    1740
ctccttccag cactggtgtt cgaaaaggct ggcatgaaca tgtgactcag gacctacgga    1800
gtcatctagt ccataaactc gttcaagcca tcttcccaac tccagaccct gcagctctga    1860
aagatcgccg catggagaac ctggttgcct atgctaagaa agtggaggga gacatgtatg    1920
agtctgctaa tagcagggat gaatactatc atttattagc agagaaaatc tataaaatac    1980
aaaaagaact agaagaaaag cggaggtcac gtttacataa gcaaggcatc ctgggtaacc    2040
agccagcttt accagcttct ggggctcagc ccctgtgat ccaccagcc cagtctgtaa    2100 gacctccaaa tgggcccctg cctttgccag tgaatcgcat gcaggtttct caagggatga    2160
attcatttaa cccaatgtcc ctgggaaacg tccagttgcc acaggcaccc atgggacctc    2220
gtgcagcctc ccctatgaac cactctgtgc agatgaacag catggcctca gttccgggta    2280
tggccatttc tccttcacgg atgcctcagc ctccaaatat gatgggcact catgccaaca    2340
acattatggc ccaggcacct actcagaacc agtttctgcc acagaaccag tttccatcat    2400
ccagtggggc aatgagtgtg aacagtgtgg gcatgggca accagcagcc caggcaggtg    2460
tttcacaggg tcaggtacct ggagctgctc tccctaaccc tctgaacatg ctggcacccc    2520
aggccagcca gctgccttgc ccaccagtga cacagtcacc attgcacccg actccacctc    2580
ctgcttccac agctgctggc atgccctctc tccaacatcc aacggcacca ggaatgaccc    2640
ctcctcagcc agcagctccc actcagccat ctactcctgt gtcatctggg cagactccta    2700
ccccaactcc tggctcagtg cccagcgctg cccaaacaca gagtacccct acagtccagg    2760
cagcagcaca ggctcaggtg actccacagc ctcagacccc agtgcagcca ccatctgtgg    2820
ctactcctca gtcatcacag cagcaaccaa cgcctgtgca tactcagcct cctggcacac    2880
cgctttctca ggcagcagcc agcattgata atagagtccc tactccctcc tctgtgacca    2940
gtgctgaaac cagttcccag cagccaggac ccgatgtgcc catgctggaa atgaagacag    3000
aggtgcagac agatgatgct gagcctgaac ctactgaatc caaggggggaa cctcggtctg    3060 agatgatgga agaggattta caaggttctt cccaagtaaa agaagagaca gatacgacag    3120
agcagaagtc agagccaatg gaagtagaag aaaagaaacc tgaagtaaaa gtggaagcta    3180
aagaggaaga agagaacagt tcgaacgaca cagcctcaca atcaacatct ccttcccagc    3240
cacgcaaaaa aatctttaaa cccgaggagc tacgccaggc acttatgcca actctagaag    3300
cactctatcg acaggaccca gagtctttgc ctttcgtca gcctgtagat cctcagctcc    3360
taggaatccc agattatttt gatatagtga agaatcctat ggacctttct accatcaaac    3420
gaaagctgga cacagggcaa tatcaagaac cctggcagta tgtggatgat gtctggctta    3480
tgttcaacaa tgcgtggcta tataatcgta aaacgtcccg tgtatataaa ttttgcagta    3540
```

```
aacttgcaga ggtctttgaa caagaaattg accctgtcat gcagtctctt ggatattgct   3600
gtggacgaaa gtatgagttc tccccacaga ctttgtgctg ttacggaaag cagctgtgta   3660
caattcctcg tgatgcagcc tactacagct atcagaatag gtatcatttc tgtgagaagt   3720
gtttcacaga gatccagggc gagaatgtga ccctgggtga cgaccttcc caacctcaga   3780
cgacaatttc caaggatcaa tttgaaaaga agaaaaatga taccttagat cctgaacctt   3840
ttgttgactg caaagagtgt ggccggaaga tgcatcagat ttgtgttcta cactatgaca   3900
tcatttggcc ttcaggtttt gtgtgtgaca actgtttgaa gaaactggc agacctcgga    3960
aagaaaacaa attcagtgct aagaggctgc agaccacacg attgggaaac acttagaag    4020
acagagtgaa taagtttttg cggcgccaga atcaccctga agctggggag ttttttgtca   4080
gagtggtggc cagctcagac aagactgtgg aggtcaagcc gggaatgaag tcaaggtttg   4140
tggattctgg agagatgtcg gaatctttcc catatcgtac caaagcactc tttgcttttg   4200
aggagatcga tggagtcgat gtgtgctttt tgggatgca tgtgcaagaa tacggctctg    4260
attgccccc accaaataca aggcgtgtat acatatctta tctggacagt attcatttct    4320
tccggccccg ctgcctccgg acagctgttt accatgagat cctcatcgga tatctcgagt   4380
atgtgaagaa attggggtat gtgacaggac atatttgggc ctgtccccca agtgaaggag   4440
atgactatat ctttcattgc cacccccctg accagaaaat ccccaaacca aaacgactac   4500
aggagtggta caagaagatg ctggacaagg cgtttgcaga gaggatcatt aacgactata   4560
aggacatctt caaacaagcg aacgaagaca ggctcacgag tgccaaggag ttgccctatt   4620
ttgaaggaga tttctggcct aatgtgttgg aagaaagcat taaggaacta gaacaagaag   4680
aagaagaaag gaaaaaagaa gagagtactg cagcgagtga gactcctgag ggcagtcagg   4740
gtgacagcaa aaatgcgaag aaaaagaaca acaagaagac caacaaaaac aaaagcagca   4800
ttagccgcgc caacaagaag aagcccagca tgcccaatgt ttccaacgac ctgtcgcaga   4860
agctgtatgc caccatggag aagcacaagg aggtattctt tgtgattcat ctgcatgctg   4920
ggcctgttat cagcactcag cccccccatcg tggaccctga tcctctgctt agctgtgacc   4980
tcatggatgg gcgagatgcc ttcctcaccc tggccagaga caagcactgg gaattctctt   5040
ccttacgccg ctccaaatgg tccactctgt gcatgctggt ggagctgcac acacagggcc   5100
aggaccgctt tgtttatacc tgcaatgagt gcaaacacca tgtggaaaca cgctggcact   5160
gcactgtgtg tgaggactat gacctttgta tcaattgcta caacacaaag agccacaccc   5220
ataagatggt gaagtggggg ctaggcctag atgatgaggg cagcagtcag ggtgagccac   5280
agtccaagag cccccaggaa tcccggcgtc tcagcatcca gcgctgcatc cagtccctgg   5340
tgcatgcctg ccagtgtcgc aatgccaact gctcactgcc gtcttgccag aagatgaagc   5400
gagtcgtgca gcacaccaag ggctgcaagc gcaagactaa tggaggatgc ccagtgtgca   5460
agcagctcat tgctctttgc tgctaccacg ccaaacactg ccaagaaaat aaatgccctg   5520
tgcccttctg cctcaacatc aaacataagc tccgccagca gcagatccag catcgcctgc   5580
agcaggctca gctcatgcgc cggcgaatgg caaccatgaa caccgcaat gtgcctcagc    5640
agagtttgcc ttctcctacc tcagcaccac ccgggactcc tacacagcag cccagcacac   5700
cccaaacacc acagccccca gcccagcctc agccttcacc tgttaacatg tcaccagctg   5760
gcttccctaa tgtagcccgg actcagcccc caacaatagt gtctgctggg aagcctacca   5820
accaggtgcc agctcccca ccccctgccc agccccacc tgcagcagta gaagcagccc     5880
```

| | |
|---|---|
| ggcaaattga acgtgaggcc cagcagcagc agcacctata ccgagcaaac atcaacaatg | 5940 |
| gcatgccccc aggacgtgca ggtatgggga ccccaggaag ccaaatgact cctgtgggcc | 6000 |
| tgaatgtgcc ccgtcccaac caagtcagtg ggcctgtcat gtctagtatg ccacctgggc | 6060 |
| agtggcagca ggcacccatc cctcagcagc agccgatgcc aggcatgccc aggcctgtaa | 6120 |
| tgtccatgca ggcccaggca gcagtggctg ggccacggat gcccaatgtg cagccaccaa | 6180 |
| ggagcatctc gccaagtgcc ctgcaagacc tgctacggac cctaaagtca cccagctctc | 6240 |
| ctcagcagca gcagcaggtg ctgaacatcc ttaaatcaaa cccacagcta atggcagctt | 6300 |
| tcatcaaaca gcgcacagcc aagtatgtgg ccaatcagcc tggcatgcag ccccagcccg | 6360 |
| gacttcaatc ccagcctggt atgcagcccc agcctggcat gcaccagcag cctagtttgc | 6420 |
| aaaacctgaa cgcaatgcaa gctggtgtgc acggcctggt gtgcctcca ccacaaccag | 6480 |
| caatgggagg cctgaatccc cagggacaag ctctgaacat catgaaccca ggacacaacc | 6540 |
| ccaacatgac aaacatgaat ccacagtacc gagaaatggt gaggagacag ctgctacagc | 6600 |
| accagcagca gcagcagcaa cagcagcagc agcagcagca caacaaaat agtgccagct | 6660 |
| tggccggggg catggcggga cacagccagt ccagcagcc acaaggacct ggaggttatg | 6720 |
| ccccagccat gcagcagcaa cgcatgcaac agcacctccc catccagggc agctccatgg | 6780 |
| gccagatggc tgctccaatg ggacaacttg gccagatggg gcagcctggg ctaggggcag | 6840 |
| acagcacccc taatatccag caggccctgc agcaacggat tctgcagcag cagcagatga | 6900 |
| agcaacaaat tgggtcacca ggccagccga accccatgag ccccagcag cacatgctct | 6960 |
| caggacagca acaggcctca catctccctg gccagcagat cgccacatcc cttagtaacc | 7020 |
| aggtgcgatc tccagcccct gtgcagtctc cacggcccca atcccaacct ccacattcca | 7080 |
| gcccgtcacc acgatacaa cccagccctt caccacacca tgtttcaccc cagactggtt | 7140 |
| cccctcaccc tggactcgca gtcaccatgg ccagctccat ggatcaggga cacctgggga | 7200 |
| accctgaaca gagtgcaatg ctccccccagc tgaataccc caacaggagc gcactgtcca | 7260 |
| gtgaactgtc cctggttggt gataccacgg agacacact agaaaagttt gtggagggtt | 7320 |
| tgtag | 7325 |

<210> SEQ ID NO 8
<211> LENGTH: 7328
<212> TYPE: DNA
<213> ORGANISM: Homo sapiens

<400> SEQUENCE: 8

| | |
|---|---|
| atggctgaga acttgctgga cggaccgccc aaccccaaaa gagccaaact cagctcgccc | 60 |
| ggtttctcgg cgaatgacag cacagatttt ggatcattgt ttgacttgga aaatgatctt | 120 |
| cctgatgagc tgatacccaa tggaggagaa ttaggccttt taaacagtgg gaaccttgtt | 180 |
| ccagatgctg cttccaaaca taacaactg tcggagcttc tcgaggagg cagcggctct | 240 |
| agtatcaacc caggaatagg aaatgtgagc gccagcagcc ccgtgcagca gggcctgggt | 300 |
| ggccaggctc aagggcagcc gaacagtgct aacatggcca gcctcagtgc catgggcaag | 360 |
| agccctctga ccagggagga ttcttcagcc cccagcctgc ctaaacaggc agccagcacc | 420 |
| tctgggccca ccccgctgc ctcccaagca ctgaatccgc aagcacaaaa gcaagtgggg | 480 |
| ctggcgacta gcagccctgc cacgtcacag actggacctg gtatctgcat gaatgctaac | 540 |
| tttaaccaga cccacccagg cctcctcaat agtaactctg gccatagctt aattaatcag | 600 |
| gcttcacaag ggcaggcgca agtcatgaat ggatctcttg gggctgctgg cagaggaagg | 660 |

```
ggagctggaa tgccgtaccc tactccagcc atgcagggcg cctcgagcag cgtgctggct    720
gagaccctaa cgcaggtttc cccgcaaatg actggtcacg cgggactgaa caccgcacag    780
gcaggaggca tggccaagat gggaataact gggaacacaa gtccatttgg acagcccttt    840
agtcaagctg gagggcagcc aatgggagcc actggagtga accccagtt agccagcaaa    900 cagagcatgg tcaacagttt gcccaccttc cctacagata tcaagaatac ttcagtcacc    960
aacgtgccaa atatgtctca gatgcaaaca tcagtgggaa ttgtacccac acaagcaatt   1020
gcaacaggcc ccactgcaga tcctgaaaaa cgcaaactga tacagcagca gctggttcta   1080
ctgcttcatg ctcataagtg tcagagacga gagcaagcaa acggaaggtt cgggcctgct   1140
cgctcccgca ttgtcgaacc atgaaaaacg tttgaatca catgacgcat tgtcaggctg    1200
ggaaagcctg ccaagttgcc cattgtgcat cttcacgaca aatcatctct cattggaaga   1260
actgcacacg acatgactgt cctgtttgcc tcccttgaa aaatgccagt gacaagcgaa    1320
accaacaaac catcctgggg tctccagcta gtggaattca aaacacaatt ggttctgttg   1380
gcacagggca acagaatgcc acttcttaa gtaacccaaa tcccatagac cccagctcca    1440
tgcagcgagc ctatgctgct ctcggactcc cctacatgaa ccagcccag acgcagctgc    1500 agcctcaggt tcctggccag caaccagcac agcctcaaac ccaccagcag atgaggactc   1560
tcaaccccct gggaaataat ccaatgaaca ttccagcagg aggaataaca acagatcagc   1620 agccccaaa cttgatttca gaatcagctc ttccgacttc cctgggggcc acaaacccac    1680
tgatgaacga tggctccaac tctggtaaca ttggaacccct cagcactata ccaacagcag   1740
ctcctccttc tagcaccggt gtaaggaaag gctggcacga acatgtcact caggacctgc   1800
ggagccatct agtgcataaa ctcgtccaag ccatcttccc aacacctgat cccgcagctc   1860
taaaggatcg ccgcatggaa aacctggtag cctatgctaa gaaagtggaa ggggacatgt   1920
acgagtctgc caacagcagg gatgaatatt atcacttatt agcagagaaa atctacaaga   1980
tacaaaaaga actagaagaa aaacggaggt cgcgtttaca taaacaaggc atcttgggga   2040
accagccagc cttaccagcc ccgggggctc agccccctgt gattccacag gcacaacctg   2100
tgagacctcc aaatggaccc ctgtccctgc cagtgaatcg catgcaagtt tctcaaggga   2160
tgaattcatt taaccccatg tccttgggga acgtccagtt gccacaagca cccatgggac   2220
ctcgtgcagc ctccccaatg aaccactctg tccagatgaa cagcatgggc tcagtgccag   2280
ggatggccat ttctccttcc cgaatgcctc agcctccgaa catgatgggt gcacacacca   2340
acaacatgat ggcccaggcg cccgctcaga gccagtttct gccacagaac cagttcccgt   2400
catccagcgg ggcgatgagt gtgggcatgg ggcagccgcc agcccaaaca ggcgtgtcac   2460
agggacaggt gcctggtgct gctcttccta accctctcaa catgctgggg cctcaggcca   2520
gccagctacc ttgccctcca gtgacacagt caccactgca cccaacaccg cctcctgctt   2580
ccacggctgc tggcatgcca tctctccagc acacgacacc acctgggatg actcctcccc   2640
agccagcagc tcccactcag ccatcaactc ctgtgtcgtc ttccgggcag actcccaccc   2700
cgactcctgg ctcagtgccc agtgctaccc aaacccagag caccccctaca gtccaggcag   2760 cagcccaggc ccaggtgacc ccgcagcctc aaacccagt tcagccccg tctgtggcta    2820 cccctcagtc atcgcagcaa cagccgacgc ctgtgcacgc ccagcctcct ggcacaccgc   2880
tttcccagcg agcagccagc attgataaca gagtccctac cccctcctcg gtggccagcg   2940
cagaaaccaa ttcccagcag ccaggacctg acgtacctgt gctggaaatg aagacggaga   3000
```

```
cccaagcaga ggacactgag cccgatcctg gtgaatccaa aggggagccc aggtctgaga    3060
tgatggagga ggatttgcaa ggagcttccc aagttaaaga agaaacagac atagcagagc    3120
agaaatcaga accaatggaa gtggatgaaa agaaacctga agtgaaagta gaagttaaag    3180
aggaagaaga gagtagcagt aacggcacag cctctcagtc aacatctcct tcgcagccgc    3240
gcaaaaaaat ctttaaacca gaggagttac gccaggccct catgccaacc ctagaagcac    3300
tgtatcgaca ggacccagag tcattacctt tccggcagcc tgtagatccc cagctcctcg    3360
gaattccaga ctattttgac atcgtaaaga atcccatgga cctctccacc atcaagcgga    3420
agctggacac agggcaatac caagagccct ggcagtacgt ggacgacgtc tggctcatgt    3480
tcaacaatgc ctggctctat aatcgcaaga catcccgagt ctataagttt tgcagtaagc    3540
ttgcagaggt ctttgagcag gaaattgacc ctgtcatgca gtcccttgga tattgctgtg    3600
gacgcaagta tgagttttcc ccacagactt tgtgctgcta tgggaagcag ctgtgtacca    3660
ttcctcgcga tgctgcctac tacagctatc agaataggta tcatttctgt gagaagtgtt    3720
tcacagagat ccagggcgag aatgtgaccc tgggtgacga cccttcacag ccccagacga    3780
caatttcaaa ggatcagttt gaaaagaaga aaaatgatac cttagacccc gaaccttt cg    3840
ttgattgcaa ggagtgtggc cggaagatgc atcagatttg cgttctgcac tatgacatca    3900
tttggccttc aggttttgtg tgcgacaact gcttgaagaa aactggcaga cctcgaaaag    3960
aaaacaaatt cagtgctaag aggctgcaga ccacaagact gggaaaccac ttggaagacc    4020
gagtgaacaa attttt gcgg cgccagaatc accctgaagc cggggaggtt tttgtccgag    4080
tggtggccag ctcagacaag acggtggagg tcaagcccgg gatgaagtca cggtttgtgg    4140
attctgggga aatgtctgaa tctttcccat atcgaaccaa agctctgttt gcttttgagg    4200
aaattgacgc cgtggatgtc tgcttttttg gaatgcacgt ccaagaatac ggctctgatt    4260
gcccccctcc aaacacgagg cgtgtgtaca tttcttatct ggatagtatt catttcttcc    4320
ggccacgttg cctccgcaca gccgtttacc atgagatcct tattggatat ttagagtatg    4380
tgaagaaatt agggtatgtg acagggcaca tctgggcctg tcctccaagt gaaggagatg    4440
attacatctt ccattgccac ccacctgatc aaaaaatacc caagccaaaa cgactgcagg    4500
agtggtacaa aaagatgctg gacaaggcgt ttgcagagcg gatcatccat gactacaagg    4560
atattttcaa acaagcaact gaagacaggc tcaccagtgc caaggaactg ccctatttg    4620
aaggtgattt ctggcccaat gtgttagaag agagcattaa ggaactagaa caagaagaag    4680
aggagaggaa aaaggaagag agcactgcag ccagtgaaac cactgagggc agtcagggcg    4740
acagcaagaa tgccaagaag aagaacaaca agaaaaccaa caagaacaaa agcagcatca    4800
gccgcgccaa caagaagaag cccagcatgc caacgtgtc caatgacctg tcccagaagc    4860
tgtatgccac catggagaag cacaaggagg tcttcttcgt gatccacctg cacgctgggc    4920
ctgtcatcaa caccctgccc cccatcgtcg accccgaccc cctgctcagc tgtgacctca    4980
tggatgggcg cgacgccttc ctcaccctcg ccagagacaa gcactgggag ttctcctcct    5040
tgcgccgctc caagtggtcc acgctctgca tgctggtgga gctgcacacc cagggccagg    5100
accgctttgt ctacacctgc aacgagtgca agcaccacgt ggagacgcgc tggcactgca    5160
ctgtgtgcga ggactacgac ctctgcatca actgctataa cacgaagagc catgcccata    5220
agatggtgaa gtgggggctg ggcctggatg acgagggcag cagccagggc gagccacagt    5280
caaagagccc ccaggagtca cgccggctga gcatccagcg ctgcatccag tcgctggtgc    5340
acgcgtgcca gtgccgcaac gccaactgct cgctgccatc ctgccagaag atgaagcggg    5400
```

```
tggtgcagca caccaagggc tgcaaacgca agaccaacgg gggctgcccg gtgtgcaagc    5460
agctcatcgc cctctgctgc taccacgcca agcactgcca agaaaacaaa tgccccgtgc    5520
ccttctgcct caacatcaaa cacaagctcc gccagcagca gatccagcac cgcctgcagc    5580
aggcccagct catgcgccgg cggatggcca ccatgaacac ccgcaacgtg cctcagcaga    5640
gtctgccttc tcctacctca gcaccgcccg ggaccccccac acagcagccc agcacacccc    5700
agacgccgca gcccctgcc cagccccaac cctcacccgt gagcatgtca ccagctggct    5760
tccccagcgt ggcccggact cagcccccca ccacggtgtc cacaggaaag cctaccagcc    5820
aggtgccggc cccccaccc ccggcccagc cccctcctgc agcggtggaa gcggctcggc    5880
agatcgagcg tgaggcccag cagcagcagc acctgtaccg ggtgaacatc aacaacagca    5940 tgccccagg acgcacgggc atggggaccc cggggagcca gatggccccc gtgagcctga    6000
atgtgccccg acccaaccag gtgagcgggc ccgtcatgcc cagcatgcct cccgggcagt    6060
ggcagcaggc gccccttccc cagcagcagc ccatgccagg cttgcccagg cctgtgatat    6120
ccatgcaggc ccaggcggcc gtggctgggc cccggatgcc cagcgtgcag ccacccagga    6180
gcatctcacc cagcgctctg caagacctgc tgcggaccct gaagtcgccc agctcccctc    6240
agcagcaaca gcaggtgctg aacattctca aatcaaaccc gcagctaatg cagctttca    6300 tcaaacagcg cacagccaag tacgtggcca atcagcccgg catgcagccc agcctggcc    6360 tccagtccca gcccggcatg caaccccagc ctggcatgca ccagcagccc agcctgcaga    6420
acctgaatgc catgcaggct ggcgtgccgc ggcccggtgt gcctccacag cagcaggcga    6480
tgggaggcct gaaccccag ggccaggcct tgaacatcat gaacccagga cacaaccca    6540 acatggcgag tatgaatcca cagtaccgag aaatgttacg gaggcagctg ctgcagcagc    6600
agcagcaaca gcagcagcaa caacagcagc aacagcagca gcagcaaggg agtgccggca    6660
tggctggggg catggcgggg cacggccagt tccagcagcc tcaaggaccc ggaggctacc    6720
caccggccat gcagcagcag cagcgcatgc agcagcatct ccccctccag ggcagctcca    6780
tgggccagat ggcggctcag atgggacagc ttggccagat ggggcagccg gggctggggg    6840
cagacagcac cccaacatc cagcaagccc tgcagcagc gattctgcag caacagcaga    6900
tgaagcagca gattgggtcc ccaggccagc cgaaccccat gagccccag caacacatgc    6960 tctcaggaca gccacaggcc tcgcatctcc ctggccagca gatcgccacg tcccttagta    7020
accaggtgcg gtctccagcc cctgtccagt ctccacggcc ccagtcccag cctccacatt    7080
ccagcccgtc accacggata cagccccagc cttcgccaca ccacgtctca ccccagactg    7140
gttcccccca ccccggactc gcagtcacca tggccagctc catagatcag ggacacttgg    7200
ggaaccccga acagagtgca atgctccccc agctgaacac cccagcagg agtgcgctgt    7260 ccagcgaact gtccctggtc ggggacacca cggggggacac gctagagaag tttgtggagg    7320
gcttgtag                                                            7328
```

<210> SEQ ID NO 9
<211> LENGTH: 20
<212> TYPE: DNA
<213> ORGANISM: Mus musculus

<400> SEQUENCE: 9

```
acgagagcaa gcaaatggag                                                 20
```

<210> SEQ ID NO 10

```
<211> LENGTH: 241
<212> TYPE: DNA
<213> ORGANISM: Mus musculus

<400> SEQUENCE: 10
tcccagttgc aaacatcagt gggaattgta cccacacaag caattgcaac aggccccaca    60
gcagaccctg aaaaacgcaa actgatacag cagcagctgg ttctactgct tcatgcccac   120
aaatgtcaga gacgagagca agcaaatgga gaggttcgag cctgttctct cccacactgt   180
cgaaccatga aaaacgtttt gaatcacatg acacattgtc aggctgggaa agcctgccaa   240
g                                                                  241

<210> SEQ ID NO 11
<211> LENGTH: 161
<212> TYPE: DNA
<213> ORGANISM: Mus musculus

<400> SEQUENCE: 11
tgaaaaacgc aaactgatac agcagcagct ggttctactg cttcatgccc acaaatgtca    60
gagacgagag caagcaaatg ggaggttcga gcctgttctc tcccacactg tcgaaccatg   120
aaaaacgttt tgaatcacat gacacattgt caggctggga a                       161

<210> SEQ ID NO 12
<211> LENGTH: 162
<212> TYPE: DNA
<213> ORGANISM: Mus musculus

<400> SEQUENCE: 12
tgaaaaacgc aaactgatac agcagcagct ggttctactg cttcatgccc acaaatgtca    60
gagacgagag caagcaaacg gcgaagttcg agcctgttct ctcccacact gtcgaaccat   120
gaaaaacgtt ttgaatcaca tgacacattg tcaggctggg aa                      162

<210> SEQ ID NO 13
<211> LENGTH: 20
<212> TYPE: DNA
<213> ORGANISM: Mus musculus

<400> SEQUENCE: 13
gacgagagca agcaaatcgg                                                20

<210> SEQ ID NO 14
<211> LENGTH: 20
<212> TYPE: DNA
<213> ORGANISM: Mus musculus

<400> SEQUENCE: 14
taggcagtgc aggattccaa                                                20
```